United States Patent
Lin et al.

(10) Patent No.: US 9,550,005 B2
(45) Date of Patent: Jan. 24, 2017

(54) SYSTEMS AND METHODS FOR STERILIZATION USING UV LIGHT

(71) Applicant: Ultraviolet Interventions, Inc., Baltimore, MD (US)

(72) Inventors: Roger C Lin, Gaithersburg, MD (US); Laurence M Sandell, Washington, DC (US)

(73) Assignee: Ultraviolet Interventions, Inc., Baltimore, MD (US)

( * ) Notice: Subject to any disclaimer, the term of this patent is extended or adjusted under 35 U.S.C. 154(b) by 0 days.

(21) Appl. No.: 14/698,778

(22) Filed: Apr. 28, 2015

(65) Prior Publication Data
US 2015/0231287 A1    Aug. 20, 2015

Related U.S. Application Data

(63) Continuation-in-part of application No. PCT/US2014/063005, filed on Oct. 29, 2014.
(Continued)

(51) Int. Cl.
| | |
|---|---|
| *A61L 2/10* | (2006.01) |
| *A61M 25/01* | (2006.01) |
| *A61M 25/00* | (2006.01) |

(52) U.S. Cl.
CPC .............. *A61L 2/10* (2013.01); *A61M 25/01* (2013.01); *A61M 2025/0019* (2013.01); *A61M 2209/10* (2013.01)

(58) Field of Classification Search
CPC ............... A61L 2/08; A61L 2/10; A61L 2/14; A61N 5/062
(Continued)

(56) References Cited

U.S. PATENT DOCUMENTS

| | | | |
|---|---|---|---|
| 4,575,181 | A | 3/1986 | Ishikawa |
| 5,260,020 | A | 11/1993 | Wilk |

(Continued)

FOREIGN PATENT DOCUMENTS

| | | |
|---|---|---|
| EP | 2 161 040 A1 | 3/2010 |
| WO | WO 89/12479 | 12/1989 |

(Continued)

OTHER PUBLICATIONS

International Searching Authority, International Search Report; Written Opinion of the International Searching Authority; and PCT Recordation of Search History for PCT/US14/63005. May 18, 2015.
(Continued)

*Primary Examiner* — William Thomson
*Assistant Examiner* — Jeffrey Lipitz
(74) *Attorney, Agent, or Firm* — Laurence M. Sandell

(57) ABSTRACT

Embodiments of this disclosure include systems, methods, and kits for sterilizing in vivo catheters using an optical fiber to deliver UV light. In an embodiment, a method for sterilizing a catheter with at least a first lumen, includes inserting a distal end of a fiber optic cable into a fiber insertion port of a catheter connector attached to a hub of the first lumen, flushing the first lumen with fluid from a fluid source, inserting the fiber optic cable into the first lumen until a stopper of the fiber optic cable is adjacent to the fiber insertion port, providing light to the fiber optic cable from a light source after the fiber optic cable is inserted into the first lumen, withdrawing the fiber optic cable from the first lumen while the light is provided, and ceasing to provide light to the fiber optic cable after the fiber optic cable is withdrawn from the first lumen. The disclosure is also applicable to catheters with multiple lumens and to catheters accessed through subcutaneous ports.

30 Claims, 24 Drawing Sheets

Related U.S. Application Data

(60) Provisional application No. 61/896,661, filed on Oct. 29, 2013.

(58) Field of Classification Search
USPC .................................................. 422/22, 24
See application file for complete search history.

(56) References Cited

U.S. PATENT DOCUMENTS

| | | | |
|---|---|---|---|
| 5,632,767 A | | 5/1997 | Sinofsky |
| 5,637,877 A | * | 6/1997 | Sinofsky .................. A61L 2/10 250/492.1 |
| 5,695,482 A | | 12/1997 | Kaldany |
| 5,908,415 A | | 6/1999 | Sinofsky |
| 5,947,959 A | | 9/1999 | Sinofsky |
| 6,443,147 B1 | | 9/2002 | Matter |
| 6,461,569 B1 | | 10/2002 | Boudreaux |
| 6,764,501 B2 | | 7/2004 | Ganz |
| 6,954,665 B2 | | 10/2005 | Pfeiffer |
| 7,175,806 B2 | | 2/2007 | Deal |
| 7,201,767 B2 | | 4/2007 | Bhullar |
| 7,553,456 B2 | | 6/2009 | Gaska |
| 7,634,996 B2 | | 12/2009 | Gaska |
| 7,829,016 B2 | | 11/2010 | Deal |
| 8,109,981 B2 | | 2/2012 | Gertner |
| 8,197,087 B2 | | 6/2012 | Sobue |
| 8,496,610 B2 | | 7/2013 | Levenson |
| 8,556,950 B2 | | 10/2013 | Rioux |
| 8,574,490 B2 | | 11/2013 | Haytman |
| 8,585,627 B2 | | 11/2013 | Dacey, Jr. |
| 8,779,386 B2 | | 7/2014 | Bak |
| 8,838,228 B2 | | 9/2014 | Beisang, III |
| 2003/0017073 A1 | * | 1/2003 | Eckhardt .................. A61L 2/10 422/24 |
| 2005/0090722 A1 | | 4/2005 | Perez |
| 2007/0176117 A1 | | 8/2007 | Redmond |
| 2008/0051736 A1 | | 2/2008 | Rioux |
| 2008/0159908 A1 | | 7/2008 | Redmond |
| 2008/0292255 A1 | * | 11/2008 | Stevens .................. A61B 18/24 385/117 |
| 2008/0306454 A1 | | 12/2008 | Sikora |
| 2009/0062871 A1 | | 3/2009 | Chin |
| 2009/0182225 A1 | * | 7/2009 | Foley .................... A61B 18/24 600/424 |
| 2009/0257910 A1 | | 10/2009 | Segal |
| 2009/0299351 A1 | | 12/2009 | Dadisman |
| 2012/0053512 A1 | | 3/2012 | Muse |
| 2012/0161032 A1 | | 6/2012 | Arcand |
| 2013/0060188 A1 | | 3/2013 | Bedwell |
| 2013/0270445 A1 | | 10/2013 | Gaska |
| 2013/0303996 A1 | | 11/2013 | Rasooly |
| 2013/0323119 A1 | | 12/2013 | Alwan |
| 2014/0039418 A1 | | 2/2014 | Rioux |
| 2014/0205498 A1 | | 7/2014 | Bak |
| 2014/0264074 A1 | | 9/2014 | Victor |
| 2014/0334974 A1 | | 11/2014 | Rasooly |

FOREIGN PATENT DOCUMENTS

| | | |
|---|---|---|
| WO | WO 02/102421 | 12/2002 |
| WO | WO 2006/133958 A1 | 12/2006 |
| WO | WO 2010/091309 A1 | 8/2010 |
| WO | WO 2012/017783 A1 | 12/2012 |
| WO | WO 2013/112944 A1 | 8/2013 |
| WO | WO 2014/159855 A1 | 10/2014 |
| WO | WO 2014/165854 A1 | 10/2014 |

OTHER PUBLICATIONS

Fiber Optics for Sale, Co., Fiber Optic Glossary. Website [online]. Publication date of Jun. 6, 2013 (Per International Search Report) URL: https://web.archive.org/web/20130421095032/http://www.fiberoptics4sale.com/Merchant2/fiber-optic-glossary.php; pp. 33, 49.

Bak, J et al. A UVC Device for Intra-luminal Disinfection of Catheters. Photochemistry and Photobiology. 2011; 87:1123-28.

Bak, J et al. Disinfection of Pseudomona aeruginosa biofilm contaminated tube lumens . Biofouling. Jan. 2010; 26(1):31-38.

Bak, J et al. UVC fluencies for preventative treatment of Pseudomonas aeruginosa contaminated polymer tubes. Biofouling. 2010;26(7):821-28.

Faber, DJ et al. Oxygen saturation-dependent absorption and scattering of blood. Physical Review Letters. 2004;93(2):028102.

Dai, T et al. Ultraviolet-C Irradiation for Prevention ot CVC-related Infections: Photochemistry and Photobiology. 2011; 87(1):250-255.

* cited by examiner

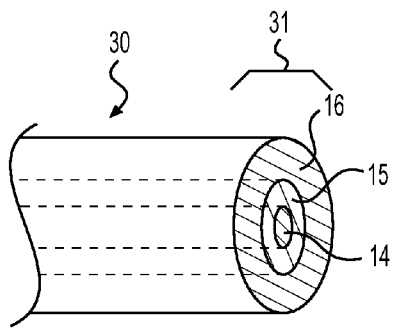
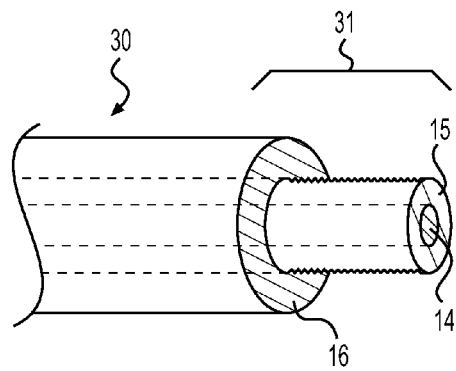
*FIG. 4A*  *FIG. 4B*
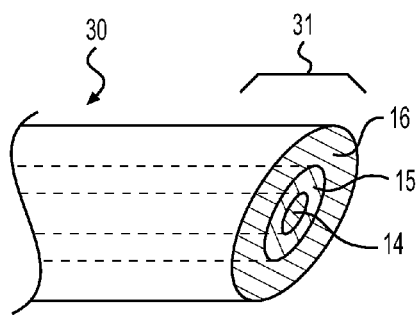
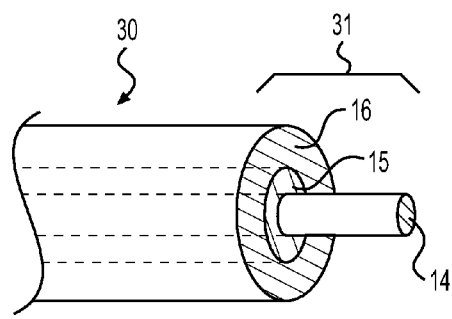
*FIG. 4C*  *FIG. 4D*
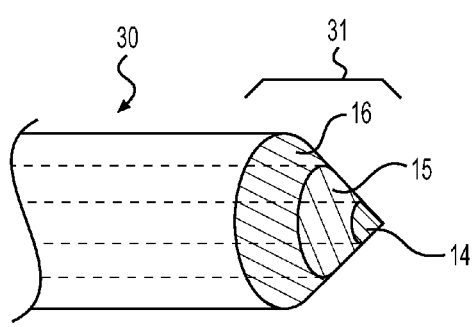
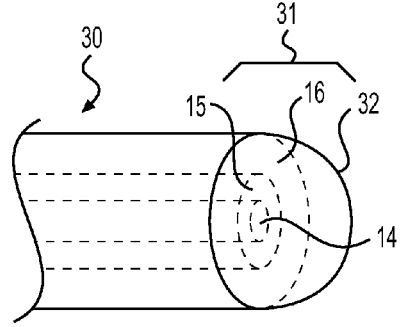
*FIG. 4E*  *FIG. 4F*

FIG. 20

| MANUFACTURER | CATHETER LENGTH DESIGNED BY MANUFACTURER (cm) | CUFF TO FORK MIN (cm) | CUFF TO FORK MAX (cm) | FORK TO HUB MID (cm) | FORK TO HUB MIN (cm) | FORK TO HUB MAX (cm) | CONNECTOR LENGTH MID (cm) | CONNECTOR LENGTH MIN (cm) | CONNECTOR LENGTH MAX (cm) | OVERLAP MID (cm) | OVERLAP MIN (cm) | OVERLAP MAX (cm) | THRESHOLD MID (cm) | THRESHOLD MIN (cm) | THRESHOLD MAX (cm) | LUMEN LENGTH DIFFERENCE MID (cm) | LUMEN LENGTH DIFFERENCE MAX (cm) | LONGER LUMEN INSERTION LENGTH MIN (cm) | LONGER LUMEN INSERTION LENGTH MAX (cm) | LONGER LUMEN INSERTION LENGTH MID (cm) | SHORTER LUMEN INSERTION LENGTH MIN (cm) | SHORTER LUMEN INSERTION LENGTH MAX (cm) | SHORTER LUMEN INSERTION LENGTH MID (cm) |
|---|---|---|---|---|---|---|---|---|---|---|---|---|---|---|---|---|---|---|---|---|---|---|---|
| MEDCOMP | 24 | | | 9 | 13 | 11 | 5 | 9 | 7 | 0.1 | 0.5 | 0.25 | 0.5 | 6 | 2 | 4 | 2 | 3 | 31.5 | 45.4 | 39.75 | 27.5 | 43.4 | 36.75 |
| MEDCOMP | 28 | | | 9 | 13 | 11 | 5 | 9 | 7 | 0.1 | 0.5 | 0.25 | 0.5 | 6 | 2 | 4 | 2 | 3 | 35.5 | 49.4 | 43.75 | 31.5 | 47.4 | 40.75 |
| MEDCOMP | 32 | | | 9 | 13 | 11 | 5 | 9 | 7 | 0.1 | 0.5 | 0.25 | 0.5 | 6 | 2 | 4 | 2 | 3 | 39.5 | 53.4 | 47.75 | 35.5 | 51.4 | 44.75 |
| MEDCOMP | 36 | | | 9 | 13 | 11 | 5 | 9 | 7 | 0.1 | 0.5 | 0.25 | 0.5 | 6 | 2 | 4 | 2 | 3 | 43.5 | 57.4 | 51.75 | 39.5 | 55.4 | 48.75 |
| MEDCOMP | 40 | | | 9 | 13 | 11 | 5 | 9 | 7 | 0.1 | 0.5 | 0.25 | 0.5 | 6 | 2 | 4 | 2 | 3 | 47.5 | 61.4 | 55.75 | 43.5 | 59.4 | 52.75 |
| MEDCOMP | 55 | | | 9 | 13 | 11 | 5 | 9 | 7 | 0.1 | 0.5 | 0.25 | 0.5 | 6 | 2 | 4 | 2 | 3 | 62.5 | 76.4 | 70.75 | 58.5 | 74.4 | 67.75 |
| TELEFLEX | 19 | 3 | 7 | 9 | 13 | 11 | 5 | 9 | 7 | 0.1 | 0.5 | 0.25 | 0.5 | 6 | 2 | 4 | 2 | 3 | 29.5 | 47.4 | 39.75 | 25.5 | 45.4 | 36.75 |
| TELEFLEX | 23 | 3 | 7 | 9 | 13 | 11 | 5 | 9 | 7 | 0.1 | 0.5 | 0.25 | 0.5 | 6 | 2 | 4 | 2 | 3 | 33.5 | 51.4 | 43.75 | 29.5 | 49.4 | 40.75 |
| TELEFLEX | 24 | 3 | 7 | 9 | 13 | 11 | 5 | 9 | 7 | 0.1 | 0.5 | 0.25 | 0.5 | 6 | 2 | 4 | 2 | 3 | 34.5 | 52.4 | 44.75 | 30.5 | 50.4 | 41.75 |
| TELEFLEX | 27 | 3 | 7 | 9 | 13 | 11 | 5 | 9 | 7 | 0.1 | 0.5 | 0.25 | 0.5 | 6 | 2 | 4 | 2 | 3 | 37.5 | 55.4 | 47.75 | 33.5 | 53.4 | 44.75 |
| TELEFLEX | 28 | 3 | 7 | 9 | 13 | 11 | 5 | 9 | 7 | 0.1 | 0.5 | 0.25 | 0.5 | 6 | 2 | 4 | 2 | 3 | 38.5 | 56.4 | 48.75 | 34.5 | 54.4 | 45.75 |
| TELEFLEX | 31 | 3 | 7 | 9 | 13 | 11 | 5 | 9 | 7 | 0.1 | 0.5 | 0.25 | 0.5 | 6 | 2 | 4 | 2 | 3 | 41.5 | 59.4 | 51.75 | 37.5 | 57.4 | 48.75 |
| TELEFLEX | 32 | 3 | 7 | 9 | 13 | 11 | 5 | 9 | 7 | 0.1 | 0.5 | 0.25 | 0.5 | 6 | 2 | 4 | 2 | 3 | 42.5 | 60.4 | 52.75 | 38.5 | 58.4 | 49.75 |
| TELEFLEX | 36 | 3 | 7 | 9 | 13 | 11 | 5 | 9 | 7 | 0.1 | 0.5 | 0.25 | 0.5 | 6 | 2 | 4 | 2 | 3 | 46.5 | 64.4 | 56.75 | 42.5 | 62.4 | 53.75 |
| TELEFLEX | 42 | 3 | 7 | 9 | 13 | 11 | 5 | 9 | 7 | 0.1 | 0.5 | 0.25 | 0.5 | 6 | 2 | 4 | 2 | 3 | 52.5 | 70.4 | 62.75 | 48.5 | 68.4 | 59.75 |
| TELEFLEX | 50 | 3 | 7 | 9 | 13 | 11 | 5 | 9 | 7 | 0.1 | 0.5 | 0.25 | 0.5 | 6 | 2 | 4 | 2 | 3 | 60.5 | 78.4 | 70.75 | 56.5 | 76.4 | 67.75 |

SYSTEMS AND METHODS FOR STERILIZATION USING UV LIGHT

CROSS-REFERENCE TO RELATED APPLICATIONS

This application is a continuation-in-part of co-pending International Patent Application PCT/US14/63005, with an international filing date of Oct. 29, 2014, the disclosure of which is incorporated by reference. This application also claims the benefit of U.S. Provisional Application No. 61/896,661, filed on Oct. 29, 2013 and relied upon by PCT/US14/63005, the disclosure of which is incorporated by reference.

FIELD

The present disclosure relates generally to systems and methods for sterilizing medical devices, and more particularly to systems and methods for sterilizing in vivo catheters using a fiber optic cable to deliver ultraviolet (UV) light.

BACKGROUND

Catheter infections are one of the biggest problems in health care today. An improved method for treating catheter infections would be useful to the medical community. Catheter infections often lead to catheter-related bloodstream infections (CRBSI's). This is a dreaded complication with an attributable mortality of 12-25% for each infection. The annual incidence of catheter related bloodstream infections is estimated to be 250,000 events per year in the US, leading to approximately 28,000 deaths per year. The median rate of catheter-related bloodstream infections in ICUs ranges between 1.8 to 5.2 per 1000 catheter days, with average costs between $23,508 and $56,000 according to some estimates. The annual cost of caring for patients with central venous catheter related bloodstream infections ranges from $296 million to $2.3 billion.

Catheter infections are associated with bacteria that form a polysaccharide matrix called a biofilm. Bacteria can colonize the external surface of a catheter or can colonize the internal lumen of a catheter. For short-term catheters, infections are primarily extraluminal. Long-term catheters are primarily associated with intraluminal bacterial colonization. The biofilm on the internal lumen has been shown as the primary infection source in short-term central venous catheters (CVCs) as early as 4 to 6 days after insertion. With catheters indwelling longer than 10 days, intraluminal biofilm is almost always associated. In intraluminal catheter infections, biofilm may establish itself along the entire length of the catheter, as well as at the catheter opening.

Additionally, catheter-associated urinary tract infections (CAUTI's) are also a large problem within the medical system. An estimated 15-25% of hospitalized patients receive urinary catheters, and if a urinary tract infection (UTI) is diagnosed in a hospitalized patient, 75% of the time it is associated with a urinary catheter. These infections are among the most common type of health-care associated infection, result in increased hospital stays, and cost the healthcare system $400 to $500 million per year. UTI's are associated with more than 13,000 deaths per year. Like central catheters, urinary catheters can harbor bacterial colonies that can produce a luminal biofilm that may be resistant to conventional antibiotics.

Currently, there is no established, effective method for treating catheter infections. The currently available methods of treating CRBSI's and CAUTI's typically comprise removing the infected catheter, introducing a new catheter into the patient, and treating the patient with a course of antibiotics. These methods are problematic because of increasing antibiotic resistance, especially in the hospital environment; patient discomfort associated with removing and replacing catheters; possible disfiguration associated with catheter insertion; expense associated with the additional medical care; costs associated with replacing catheters with suspected infections; and increased risk venous stenosis and thrombosis.

Ultraviolet (UV) light is a non-molecular based antimicrobial agent that has been investigated for catheter infection treatment. UV light has a particular band of wavelengths, 250-280 nm (UVC band), that is considered germicidal. The germicidal action occurs by the production of thymine dimers in microbial DNA. The use of UV light for disinfection is well established in water treatment. Although biofilm may attenuate microbial response to UV light, UVC light can induce DNA damage in microbes through a biofilm matrix. However, attempts to date to treat (or prevent) catheter infections using UV light have not solved the problem.

As described above, there exists a need for new technologies to both treat and prevent intraluminal catheter infections. The disclosed UV light-based sterilization systems, devices, and methods are generally directed toward addressing one or more of the problems set forth above.

SUMMARY

In accordance with an embodiment, a method for sterilizing a catheter with at least a first lumen, includes: inserting a distal end of a fiber optic cable into a fiber insertion port of a catheter connector attached to a hub of the first lumen; flushing the first lumen with fluid from a fluid source; inserting the fiber optic cable into the first lumen until a stopper of the fiber optic cable is adjacent to the fiber insertion port; providing light to the fiber optic cable from a light source after the fiber optic cable is inserted into the first lumen; withdrawing the fiber optic cable from the first lumen while the light is provided; and ceasing to provide light to the fiber optic cable after the fiber optic cable is withdrawn from the first lumen.

In accordance with another embodiment, the method further includes attaching the hub to a hub adapter of the catheter connector and attaching the fluid source to a fluid port of the catheter connector, prior to flushing the first lumen; and disengaging the hub from the hub adapter, after ceasing to provide light to the fiber optic cable. In a further embodiment, the method can also include unlocking the first lumen by disengaging a tubing clamp configured to block fluid flow through the first lumen, prior to flushing the first lumen; and locking the first lumen by engaging the tubing clamp, after withdrawing the fiber optic cable from the catheter and prior to disengaging the hub from the hub adapter.

In accordance with yet other embodiments, the step of inserting the fiber optic cable into a fiber insertion port occurs prior to the step of flushing the first lumen in certain embodiments.

In accordance with yet other embodiments, when the stopper is adjacent to the fiber insertion port, the distal end of the fiber optic cable is within 6 cm or within 3 cm from a distal end of the first lumen and does not extend beyond a distal end of the first lumen.

In accordance with yet other embodiments, the step of withdrawing the fiber optic cable from the catheter ends when the distal end of a fiber optic cable is positioned within the catheter connector, and the step of ceasing to provide light to the fiber optic cable occurs while the distal end of a fiber optic cable is positioned within the catheter connector.

In accordance with yet other embodiments, the stopper is at least one of at torque device, a hinged device, a clamping apparatus, and a bead comprising at least one of silica, plastic, resin, or epoxy.

In accordance with yet other embodiments, the catheter connector is a hemostasis valve and the fiber insertion port comprises a one-way valve.

In accordance with yet other embodiments, the method further includes aligning the stopper on a first stopper marker of the fiber optic cable and securing the stopper to the fiber optic cable. The method can also include selecting the first stopper marker from a plurality of stopper markings, such that first stopper marker corresponds to a combined length of the first lumen and the catheter connector.

In accordance with yet other embodiments, the method further includes treating a second lumen of the catheter with light from the light source.

In accordance with yet other embodiments, the method further includes confirming a match in color between at least one of the hub and at least a portion of the catheter connector, and at least one of the fiber optic connector, the stopper, and a marking on the fiber optic cable.

In accordance with yet other embodiments, the light source is a laser that provides light in the UVC band.

In accordance with yet other embodiments, the step of withdrawing the fiber optic cable is performed by hand using a time-keeping device to maintain a steady withdrawal rate. The step of withdrawing the fiber optic cable can further be performed by using equally spaced readable marks on the fiber optic cable to maintain a withdrawal rate.

In accordance with yet other embodiments, the method further includes withdrawing fluid from the first lumen, wherein the step of withdrawing fluid from the first lumen occurs prior to the step of flushing the first lumen.

In accordance with an embodiment, a kit for sterilizing a catheter of at least one designated catheter type with at least a first lumen includes: a first fiber optic cable with a first fiber optic connector; a first catheter connector; a first stopper; and packaging containing the first fiber optic cable, the first catheter connector, and the first stopper. The first catheter connector includes a first fiber insertion port configured to receive the first fiber optic cable and a first hub adapter configured to connect with a first hub of the first lumen of the catheter at a proximal end of the first lumen. The first stopper is attached to or integrally formed with the first fiber optic cable at a first fiber length from a first distal end of the first fiber optic cable. The first fiber length corresponds to a combined length of a first lumen length of the first lumen from the first hub to a first lumen distal end of the first lumen and a first catheter connector length of the first catheter connector from the first fiber insertion port to the first hub adapter.

In accordance with another embodiment, the first fiber length corresponds to the combined length by being shorter than, but within 6 cm of, a sum of the first lumen length and the first catheter connector length less an overlap connection length of the first hub adapter and the first hub.

In accordance with yet another embodiment, the kit further includes a label including information about the at least one designated catheter type.

In accordance with yet another embodiment, the packaging is sterile packaging and its contents are sterile.

In accordance with yet another embodiment, the first catheter connector is a hemostasis valve and the first fiber insertion port includes a one-way valve.

In accordance with yet another embodiment, the kit further includes a syringe filled with a flushing fluid.

In accordance with yet another embodiment, the first stopper is at least one of a torque device, a hinged device, a clamping apparatus, and a bead comprising at least one of silica, plastic, resin, or epoxy.

In accordance with yet another embodiment, the first fiber length is between 25 cm and 80 cm.

In accordance with yet another embodiment, the kit further includes an empty syringe or other suction device.

In accordance with yet another embodiment, the first fiber optic cable includes a plurality of equally spaced readable marks on the first fiber optic cable between the first stopper and the first distal end.

In accordance with yet another embodiment, the kit further includes a second fiber optic cable with a second fiber optic connector, a second catheter connector, and a second stopper. The second catheter connector includes a second fiber insertion port configured to receive the second fiber optic cable, and a second hub adapter configured to connect with a second hub of a second lumen of the catheter at a proximal end of the second lumen. The packaging contains the second fiber optic cable, the second catheter connector, and the second stopper. The second stopper is attached to or integrally formed with the second fiber optic cable at a second fiber length from a second distal end of the second fiber optic cable. The first fiber length can be longer than the second fiber length. At least one of the first fiber optic connector, the first stopper, and a marking or flag on the first fiber optic cable can be colored blue, and at least one of the second fiber optic connector, the second stopper, and a marking or flag on the second fiber optic cable can be colored red.

In accordance with an embodiment, a kit for sterilizing a catheter of at least one designated catheter type with at least a first lumen includes a first fiber optic cable with a first fiber optic connector; a first catheter connector, a first stopper; and packaging containing the first fiber optic cable, the first catheter connector, and the first stopper. The first catheter connector includes a first fiber insertion port configured to receive the first fiber optic cable, and a first hub adapter configured to connect with a first hub of the first lumen of the catheter at a proximal end of the first lumen. The first fiber optic cable includes at least a first stopper marking at a first fiber length from a first distal end of the first fiber optic cable, and the first fiber length corresponds to a combined length of a first lumen length of the first lumen from the first hub to a first lumen distal end of the first lumen and a first catheter connector length of the first catheter connector from the first fiber insertion port to the first hub adapter.

In accordance with another embodiment, the first fiber length is between 25 cm and 80 cm.

In accordance with an embodiment, an apparatus for sterilizing a catheter with at least a first lumen includes a first fiber optic cable, a first catheter connector, and a stopper affixed to the first fiber optic cable. The first catheter connector includes a first fiber insertion port configured to receive the first fiber optic cable, and a first hub adapter configured to connect with a hub of the first lumen of the catheter at a proximal end of the first lumen. The stopper cannot pass through the first fiber insertion port, and it is positioned along the first fiber optic cable such that when the first fiber optic cable is fully inserted into the first fiber insertion port, a distal end of the first fiber optic cable is positioned near a distal end of the first lumen.

In accordance with another embodiment, the apparatus also includes a second fiber optic cable and a second catheter connector. The second catheter connector includes a second fiber insertion port configured to receive the second fiber optic cable, and a second hub adapter configured to connect with a hub of a second lumen of the catheter at the proximal end of the catheter.

In accordance with yet other embodiments, the stopper is a torque device; a bead of glue, plastic, or epoxy; or a clamp.

In accordance with yet another embodiment, the first fiber optic cable includes a fiber jacket and the stopper is the distal-most edge of the fiber jacket.

In accordance with yet other embodiments, the first fiber optic cable is configured to scatter light radially along a portion of its length. The portion may substantially be the section of the first fiber optical cable that is distal to the stopper.

In accordance with yet other embodiments, the first fiber optic cable the first fiber optic cable is configured to scatter light radially by incorporating discontinuities. The discontinuities may be formed by bending the first fiber optic cable beyond its minimum momentary bending radius in a controlled manner, crushing the first fiber optic cable in a controlled manner, providing the first fiber optic cable with a cladding with a roughened surface, or by scoring or cutting a layer of the first optical fiber with a laser.

In accordance with yet other embodiments, the first fiber optic cable is configured to scatter light radially by incorporating scattering centers. The scattering centers may be particles that alter the local refractive index of the cladding and/or core of the first fiber optic cable.

In accordance with yet other embodiments, the first fiber optic cable includes a tip configured to scatter radially substantially all light received by the first fiber optic cable. The tip may include a lens, a light diffusor, bristles, and/or a radiopaque element.

In accordance with yet another embodiment, the first catheter connector includes a first fluid port.

In accordance with an embodiment, an apparatus for sterilizing a catheter with at least a first lumen includes a first fiber optic cable, a first catheter connector, and at least one stopper marking on the first fiber optic cable. The first catheter connector includes a first fiber insertion port configured to receive the first fiber optic cable and a first hub adapter configured to connect with a hub of the first lumen of the catheter at a proximal end of the first lumen. When a stopper is affixed to the first fiber optic cable at the at least one stopper marking, the stopper cannot pass through the first fiber insertion port such that, when the first fiber optic cable is fully inserted into the first fiber insertion port, a distal end of the first fiber optic cable is positioned near a distal end of the first lumen.

In accordance with other embodiments, the first fiber optic cable is configured to scatter light radially along a portion of its length. The portion may substantially be the section of the first fiber optical cable that is distal to the at least one stopper marking.

In accordance with yet another embodiment, the at least one stopper marking includes a plurality of stopper markings. Each of the plurality of stopper markings corresponds to a different potential length of the first lumen.

In accordance with an embodiment, an apparatus for sterilizing a catheter with at least a first lumen using at least a first fiber optic cable includes a controller, a UV light source, a first fiber optic port configured to optically couple with the first fiber optic cable, and a first transmitting cable configured to propagate UV light from the UV light source to the first fiber optic port. The UV light source is controlled by the controller and includes a first UV laser.

In accordance with another embodiment, the UV light source is further configured to emit light in the visible spectrum.

In accordance with yet another embodiment, the controller is configured to modulate the intensity of UV light emitted from the UV light source.

In accordance with yet another embodiment, the first UV laser is a laser-diode pumped solid state UV laser.

In accordance with yet other embodiments, the apparatus further includes a fiber splitter positioned along the first transmitting cable and a light detector. The light detector is coupled to the controller and optically coupled to the fiber splitter. The fiber splitter may be configured to provide a fraction of light provided by the UV light source to the light detector and/or be configured to provide a fraction of light backreflected from the first fiber optic cable to the light detector.

In accordance with yet another embodiment, the apparatus further includes an automatic movement mechanism, a cable position sensor coupled to the controller, and an attachment for securing a catheter connector. The catheter connector is configured to engage a proximal end of the first lumen and to receive the first optic cable. The automatic movement mechanism is controlled by the controller.

In accordance with yet another embodiment, the apparatus further includes at least one motor controlled by the controller. The apparatus is configured to engage with a first cartridge, which includes the first fiber optic cable, a first fiber optic cable position sensor, and a mechanism for moving the first fiber optic cable. When the apparatus engages with the first cartridge, the first fiber optic port optically couples with the first fiber optic cable, the first fiber optic cable position sensor couples with the controller, and the at least one motor mechanically couples to the mechanism for moving the first fiber optic cable.

In accordance with yet another embodiment, the apparatus further includes a second fiber optic port configured to optically couple with a second fiber optic cable and a second transmitting cable configured to propagate UV light from the UV light source to the second fiber optic port.

In accordance with an embodiment, a cartridge for sterilizing a catheter with at least a first lumen includes a first fiber optic cable, a first set of rollers engaged with and configured to move the first fiber optic cable, a first hub adapter configured to engage with a proximal end of the first lumen, a first fiber optic connector optically coupled to the first fiber optic cable, and a first sensor configured to generate first feedback on a position of the first fiber optic cable or the first set of rollers. The cartridge is configured to engage with a base unit configured to provide light to the first fiber optic cable through the first fiber optic connector, drive the first set of rollers via a first mechanical coupling, and receive the first feedback from the first sensor.

In accordance with another embodiment, the cartridge also includes a data storage device. The data storage device contains data relating to the cartridge and is configured to provide the data to a controller of the base unit when the cartridge is engaged with the base unit.

In accordance with yet another embodiment, the first fiber optic cable is stored within the cartridge as a coil assembled using an over/under cable coiling technique.

In accordance with yet another embodiment, the cartridge also includes a second fiber optic cable, a second set of rollers engaged with and configured to move the second fiber optic cable, a second hub adapter configured to engage with a proximal end of a second lumen of the catheter, a second fiber optic connector optically coupled to the second fiber optic cable, and a second sensor configured to generate second feedback on a position of the second fiber optic cable or the second set of rollers.

In accordance with an embodiment, an adapter for introducing a fiber optic cable into a subcutaneous port with a catheter lumen opening and a septum, includes a handle with a proximal end and a distal end, a curved needle, and a fiber receiving opening. The curved needle extends from the distal end of the handle, shares a conduit with the handle, includes a tip, is configured to pass through the septum and lodge the tip in a catheter opening of the subcutaneous port, and is dimensioned such that the fiber optic cable may pass through it without surpassing a minimum momentary bending radius of the fiber optic cable. The fiber receiving opening is positioned at the proximal end of the handle. The tip is configured to pierce the septum.

In accordance with another embodiment, the fiber receiving opening includes a one-way valve.

Additional objects and advantages of embodiments consistent with the disclosure will be set forth in part in the following description, and in part will be obvious from the description, or may be learned by practice of the embodiments disclosed herein. It is to be understood that both the foregoing general description and the following detailed description are exemplary and explanatory only and are not restrictive of the disclosure, as claimed.

The accompanying drawings, which are incorporated in and constitute a part of this specification, illustrate several embodiments consistent with the written disclosure and together with the description, serve to explain the principles of the disclosure.

BRIEF DESCRIPTION OF THE DRAWINGS

FIGS. 4A-I are illustrations of UV light-scattering tips of dynamic fiber optic cables, according to at least one aspect of the disclosure

FIG. 20 is a table illustrating exemplary calculations of cable insertion lengths, according to at least one aspect of the disclosure.

DETAILED DESCRIPTION

This disclosure is generally directed towards the use of UV light delivered through fiber optic cables to prevent and treat intraluminal catheter infections. While many of the embodiments discussed herein are directed to treating CRB-SI's in hematological catheters, the person of skill in the art would understand the disclosed teachings to be applicable as prophylactic measures to prevent intraluminal catheter infection; to treat and prevent extra-luminal catheter infections; to treat and prevent infections in urinary catheters and/or other catheter types; and to reduce bacterial colonies, in vivo, in other lumen-containing medical devices, such as feeding tubes and breathing tubes.

Reference will now be made in detail to the exemplary embodiments of the disclosure, examples of which are illustrated in the accompanying drawings. Wherever possible, the same reference numbers will be used throughout the drawings to refer to the same or like parts. Also, any aspect set forth in any embodiment may be used with any other embodiment set forth herein. It may also be noted that the elements depicted in the accompanying drawing may not be to scale with respect to one another.

Figure 1:
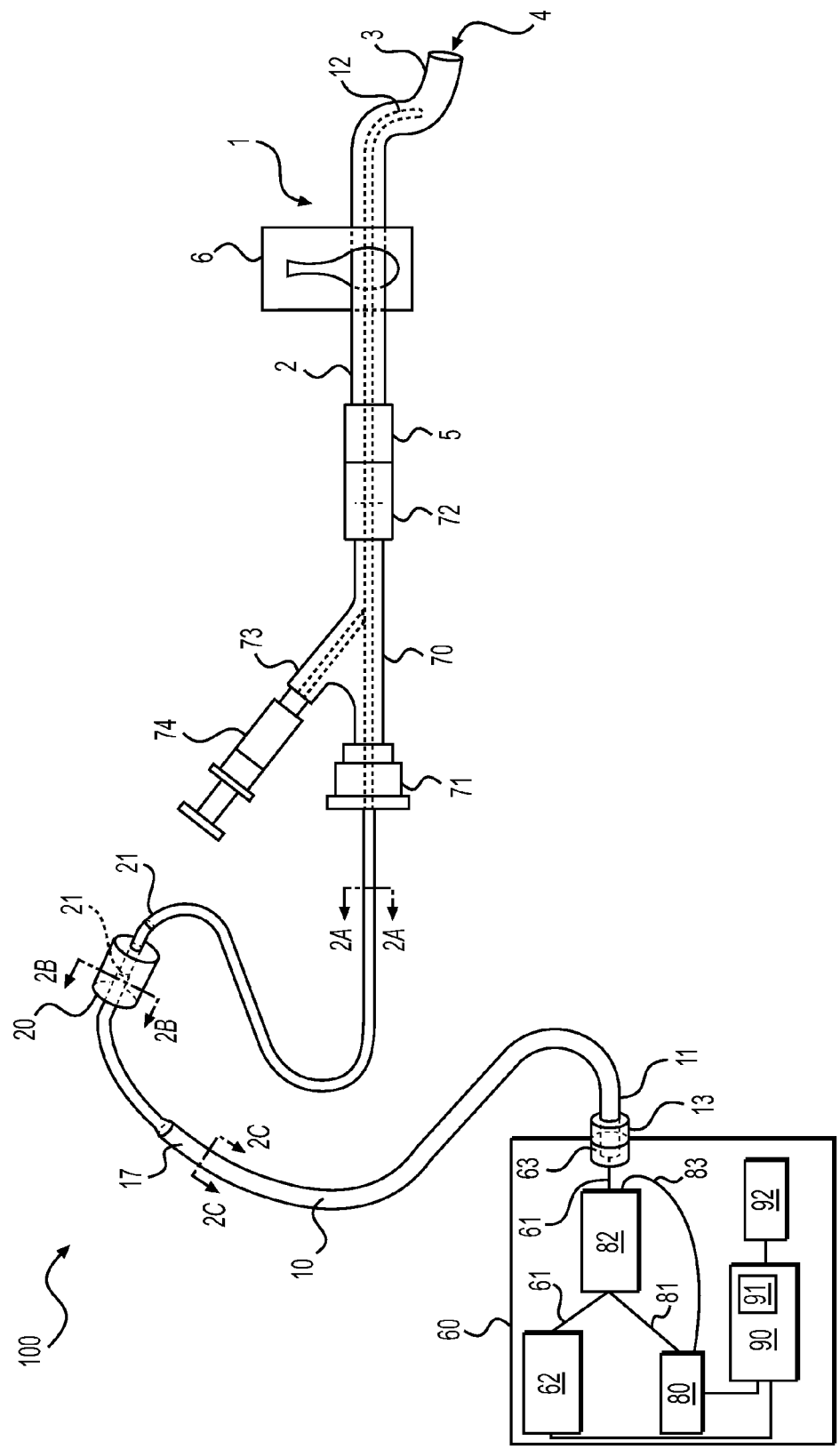
FIG. 1 is an illustration of a UV light-based sterilization system, according to at least one aspect of the disclosure.

FIG. 1 illustrates an exemplary UV light-based sterilization system 100, which may sterilize catheter 1, having lumen 4, proximal catheter end 2, and distal catheter end 3. Whereas distal end 3 (along with most of catheter 1) may be positioned inside a patient's body, catheter hub 5 may be affixed to proximal catheter end 2. Additionally, catheter 1 may include (outside the patient's body) tubing clamp 6, which may be used to seal the catheter.

As used herein, the term sterilize (and other forms thereof) broadly includes disinfecting, reducing the number of viable microbes or microbe colonies, and/or otherwise killing microbes, as well as other meanings known in the art.

Figure 18:
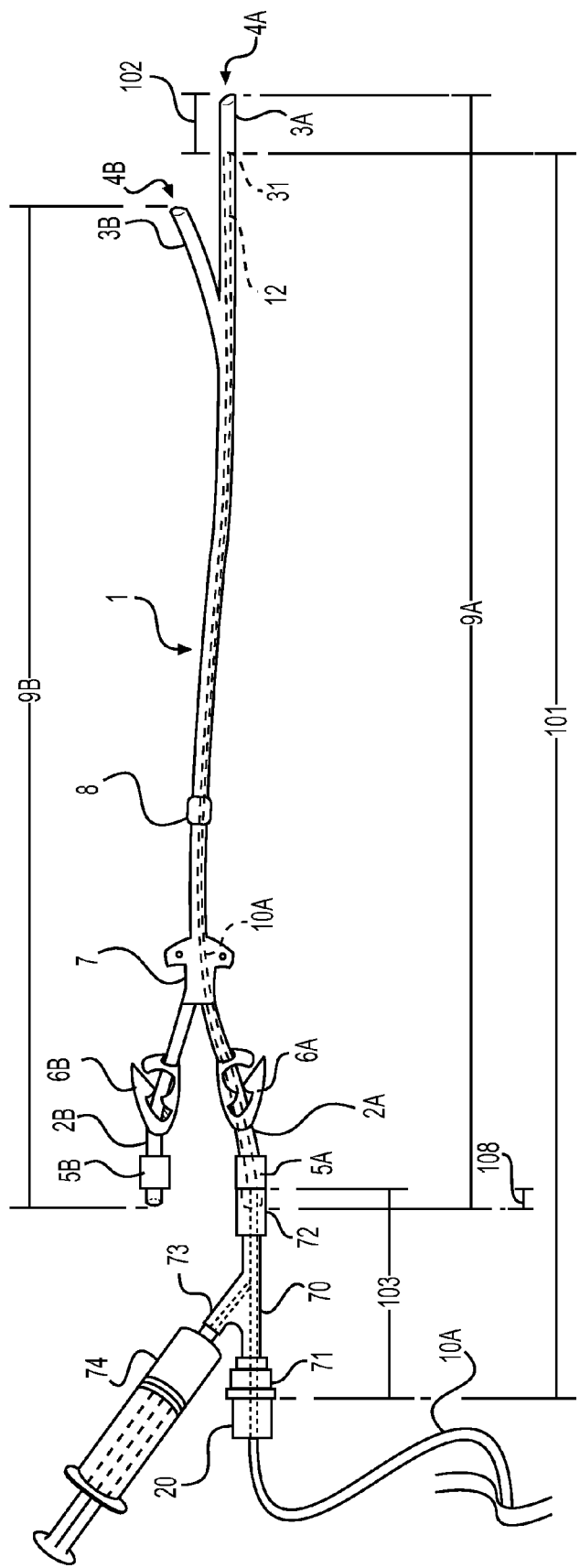
FIG. 18 is an illustration of a multi-lumen catheter with an inserted fiber optic cable, according to at least one aspect of the disclosure.

Additionally, a catheter 1 comprising multiple lumens 4, discussed herein, may have multiple catheter hubs 5, each catheter hub 5 corresponding to and providing engagement with one of the multiple lumens 4. As such, each lumen 4 of a multi-lumen catheter can have its own catheter hub 5. For example, FIG. 18 illustrates a chronic hemodialysis catheter with two lumens 4A and 4B. First lumen 4A has a distal end 3A and a proximal end 2A, which terminates in hub 5A. Lumen 4A has a first lumen length 9A, from the proximal-most portion of hub 5A to the distal-most portion of distal lumen end 3A. Similarly, second lumen 4B has a distal end 3B and a proximal end 2B, which terminates in hub 5B. Lumen 4B has a second lumen length 9B, from the proximal-most portion of hub 5B to the distal-most portion of distal lumen end 3B. It should be noted that while elements within FIG. 18 (for example, lumens 4A and 4B) are depicted with curved portions, it should be understood that lengths (for example 9A and 9B) can reflect length measurements of these elements when they are straightened. Catheter 1 may also include tubing clamps 6A and 6B, cuff 8, and fork 7. Tubing clamp 6A stops fluid flow through lumen 4A when locked or engaged, and tubing claim 6B stops fluid flow though lumen 6B when locked or engaged. Fork 7 splits lumens 4A and 4B into separate structures in the proximal direction and combines the exteriors of lumens 4A and 4B so that they share an exterior surface in the distal direction. However, as depicted in FIG. 18, the distal ends 3A and 3B of the respective lumens 4A and 4B may also be split. When catheter 1 is implanted, cuff 8 may be implanted near the patient's skin. Cuff 8 can serve to reduce extraluminal infection and further secure the catheter because bodily tissues can grow into the cuff 8 material.

In order to protect human tissue from being exposed to UV light from UV light-based sterilization system 100, catheter 1 may be made of material opaque to ultraviolet light. In such a circumstance, UV radiation emitted inside the catheter lumen 4 is absorbed by the catheter walls before reaching extra-luminal catheter surfaces or human tissue. For example, catheters are commonly made from polyurethane and/or silicone, which are both UV opaque materials. Alternatively, catheter 1 may be made of UV transparent material, which would allow for the delivery of light on the outside of the catheter and thereby permit extra-luminal catheter sterilization. UV transparent materials suitable for catheter 1 construction may include the class of polytetrafluoroethylenes and copolymers based on cyclic olefins and ethylene.

Exemplary UV light-based sterilization system 100 may include catheter connector 70, which in preferred embodiments may be a hemostasis valve, for example a Tuohy borst. Catheter connector 70 is preferably opaque to UV light in order to prevent unnecessary UV radiation exposure outside of UV light-based sterilization system 100, but transparent as to visible light. At its distal end, catheter connector 70 may include hub adapter 72 to engage with catheter hub 5, which in preferred embodiments may be a Luer lock connection. At its proximal end, catheter connector 70 may include fiber insertion port 71, which in preferred embodiments may be a one-way valve. As depicted in FIG. 18, catheter connector 70 has a length of catheter connector length 103, from the proximal-most portion of fiber insertion port 71 to the distal-most portion of hub adapter 72. Additionally, catheter connector 70 may include fluid port 73 to engage with fluid source 74; in preferred embodiments fluid source 74 may be a saline syringe containing a saline solution. In some embodiments, fluid port 73 includes a one-way valve. In alternative embodiments, fluid port 73 may be omitted such that any flushing of catheter 1 with a fluid (discussed below) may occur either before hub adapter 72 engages with catheter hub 5 or after hub adapter 72 is disengaged from catheter hub 5.

As depicted in FIG. 1, exemplary UV light-based sterilization system 100 also includes fiber optic cable 10 that may be inserted—distal end 12 first—into fiber insertion port 71, through catheter connector 70, and into lumen 4 of catheter 1. Fiber insertion port 71 can, in some embodiments, accept diameters larger than that of the fiber optic cable 10. The proximal end 11 of fiber optic cable 10 may include fiber optic connector 13. In some embodiments fiber optic cable 10 may include one or more stopper markings 21, upon which stopper 20 may be aligned and attached. FIG. 1 illustrates alignment of stopper 20 centered on a stopper marking 21. However, in other embodiments, the distal-most edge of stopper 20 may be aligned with stopper marking 21. Other alignment configurations, including aligning the proximal-most edge of stopper 20 with stopper marking 21, are also contemplated. In other embodiments, stopper 20 may be affixed upon fiber optic cable 10 without stopper markings 21.

A proximal portion of fiber optic cable 10 may protected by fiber jacket 17.

Figure 2A:
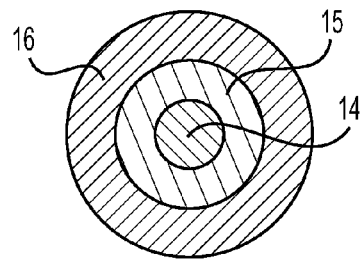
FIGS. 2A-C are illustrations of cross-sectional views of a fiber optic cable, according to at least one aspect of the disclosure.
Figure 2B:
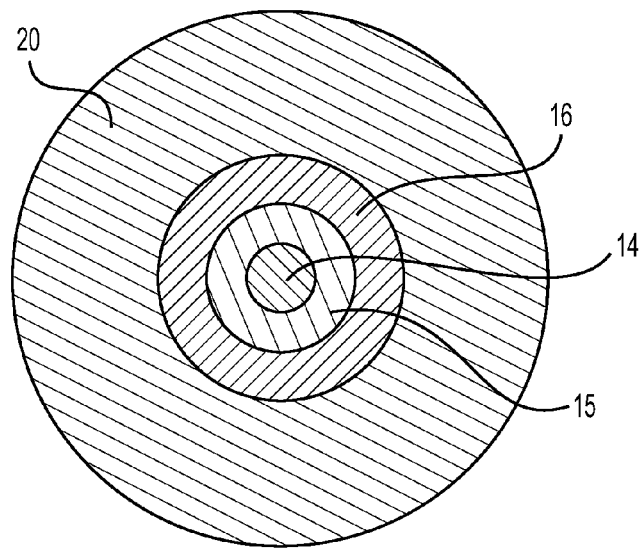
Figure 2C:
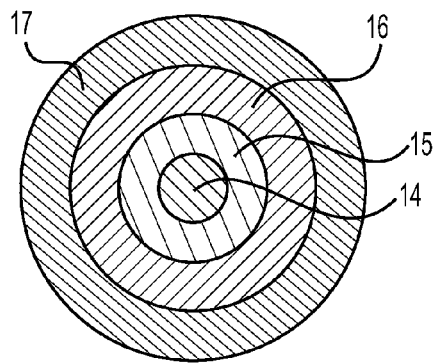

FIGS. 2A, 2B, and 2C depict exemplary cross sections of fiber optic cable 10. As depicted in FIG. 2A, fiber optic cable 10 includes core 14, cladding 15, and buffer 16. As is well known to persons of skill in the art, core 14 and cladding 15 propagate light, and buffer 16 serves to protect the fiber. Fiber optic cable 10 should have flexibility to adequately navigate the curvature present within lumen 4 of an indwelling catheter 4, have a core 14 size suitable to deliver sufficient UV power to kill microorganisms, and have a diameter small enough such that it may fit within a small lumen 4. These characteristics may be met by, for example, a fiber optic cable 10 with core 14 having a diameter of 400 micrometers, cladding 15 having an outer diameter of 430 micrometers, and buffer 16 having an outer diameter of 730 micrometers. In certain embodiments, fiber optic cable may have a large numerical aperture, such as, for example 0.48, such that a substantial portion of the light emitted at the distal cable end 12 may be scattered toward the catheter walls rather propagated than straight forward.

Additionally, as a method of protecting fiber optic cable 10, the fiber can be coated with an ultraviolet transparent polymer. For example, this can be a polymer that is related to the family of polytetrafluoroethylenes, or it can be made of a copolymer based on cyclic olefins and ethylene, which can transmit ultraviolet light. Further, fiber optic cable 10 may include an additional antimicrobial or antiseptic coating in order to improve microbial killing properties. The coating may include, but is not limited to, antibiotics, silver, alcohols, or even possibly chlorhexidine or iodine. The coating can be applied in a number of ways, such as impregnating within the optical fiber buffer or by dip coating, which are known in the state of the art. Additionally or alternatively, the coating may comprise a hydrophilic substance (for example, a polyolefin such as polyvinyl pyrolidone, a polysaccharide such as hyaluronic acid or chondroitin sulfate, or a polyethyl maleic anhydride), which can reduce friction of the optical fiber as it passes through the catheter. Or, as will be discussed below, the outside of fiber optic cable 10 may comprise a bristled or rough surface on buffer 16, which may be used to remove biofilm from lumen 4.

FIG. 2B illustrates a cross-section of fiber optic cable 10 where stopper 20 is attached. The diameter of stopper 20 may prevent it from passing through fiber insertion port 71. The purpose of stopper 20 is to limit the range of movement of fiber optic cable 10, such that distal end 12 of cable 10 does not protrude into a patient's body outside of (or much outside of) of distal catheter end 3. If distal end 12 extends outside (or much outside) of distal catheter end 3, distal cable end 12 might pierce, lacerate, irritate, or otherwise damage bodily tissues and organs, including, for example, the heart where central venous catheters are positioned and the bladder where urinary catheters are positioned. Stopper markings 21 may correspond to different catheter 1 lengths, and the stopper markings 21 may be used as a guide to attach stopper 20 at an appropriate position along fiber optic cable 10. And, in some embodiments, as discussed below, various stopper markings 21 may correspond to particular catheter 1 types.

FIG. 18 depicts a first fiber optic cable 10A inserted into first lumen 4A of a multi-lumen catheter through catheter connector 70 such that stopper 20 of fiber optic cable 10A is adjacent to fiber insertion port 71. In this fully inserted position, the distal-most portion of distal end 12 of fiber optic cable 10A is located within lumen 4A a threshold distance 102 away from the distal-most portion of distal cable end 3A. And, the portion of cable 10A inserted catheter connector 70 and into lumen 4A has insertable fiber length 101. Insertable fiber length 101 is length of cable 10 from the distal-most portion of attached stopper 20 to the cable's light-scattering tip 31 at the distal cable end 12. Insertable fiber length 101 corresponds to catheter connector length 103 and lumen length 9A, but can be shorter than the sum of those lengths because of threshold distance 102 and/or the overlap 108 in lengths 9A and 103 due to the engagement of hub 5A and hub adapter 72.

A threshold distance 102 can be included to reduce the likelihood that a fiber optic cable 10 will extend beyond the distal end 3 of a catheter lumen. Because, in some embodiments, a substantial portion of UV light emitted from light-scattering fiber tip 31 at the end of distal end 12 is emitted in the forward direct direction, the distal-most portions of the intraluminal walls can be exposed to sufficient UV light even if the fiber tip 31 is set back by the threshold amount 102 when it is fully inserted. At the same time, the inclusion of a threshold distance can reduce UV light exposure beyond distal catheter end 3, which may be desired. Additionally, in some catheters, lumen length 9 may be effectively reduced when the catheter is bent, which can occur during proper implantation of certain types of catheters, such as, for example, certain tunneled chronic dialysis catheters. Here, the provision of an adequate threshold length 102 reduces the likelihood that fiber 10 will project beyond the distal end of the catheter when catheter 1 is bent. Further, some catheters include side holes in luminal walls near distal ends 3, 3A, 3B to, e.g., improve fluid flow characteristics. It is contemplated that threshold distance 102 may be long enough to prevent the distal-most portion of distal fiber end 12 from being located adjacent to or distal to such holes, in order to, for example, reduce UV radiation projecting through the holes, and prevent the possibility of tip 31 protruding through, entering, or otherwise engaging with the holes. In exemplary embodiments threshold length 102 is at least 0.5 cm, or at least 1 cm. Additionally, in exemplary embodiments, the threshold distance 102 is less than 6 cm, less than 5 cm, less than 4 cm, less than 3 cm, less than 2 cm, less than 1.5 cm, or less than 1 cm.

As discussed above and depicted in FIG. 18, the threshold distance 102 is a function of lumen length 9, catheter connector length 103, overlap 108, and the insertable length 101 of cable 10. And, insertable length 101 is a function of the placement of stopper 10 along cable 30. Thus, given a particular lumen length 9, catheter connector length 103, and overlap 108, a fiber manufacturer or operator can achieve a desired threshold distance 102 based on placement of stopper 20.

Certain dialysis catheter manufacturers provide catheters with designated catheter lengths that describe the distance between the distal end of the longer lumen to the fork 7. For example, Medcomp sells dialysis catheters with distal end 3 to fork 7 measurements of 24 cm, 28 cm, 32 cm, 36 cm, 40 cm, and 55 cm. Other catheter manufacturers provide designated catheter lengths that describe the distance between the distal end 3 of the longer lumen to the cuff 8. For example, Teleflex sells dialysis catheters with distal end 3 to cuff 8 measurements of 19 cm, 23 cm, 24 cm, 27 cm, 28 cm, 31 cm, 32 cm, 36 cm, 42 cm, and 50 cm. Typical distances from cuff 8 to fork 7 can range approximately 3 cm to 7 cm, and are commonly around 5 cm. And typical distances from fork 7 to catheter hub 5 can range approximately 9 cm-13 cm, and are commonly around 11 cm. Catheter connector lengths typically range from 5 cm from 9 cm, and are commonly around 7 cm. Overlap is typically less that 0.5 cm, and are commonly around 0.25 cm. Based on the discussion above, the person of skill in the art can determine approximate ranges for lumen lengths 9A for certain types of catheters.

In preferred embodiments, insertable length 101 is equal to lumen length 9 plus catheter connector length 103, less overlap 108, and less desired threshold distance 102. Thus, with reference to the exemplary ranges of lengths 9A, 103, 102, and 108 discussed above, insertable lengths 101 for the longer lumen can range from 29.5 cm to 78.4 cm, based on the characteristics of the lumen. These and other calculations for exemplary insertable lengths 101 are shown in the table of FIG. 20. However, in other embodiments, for example for different catheter types, insertable lengths 101 can be shorter or longer.

Notably, first lumen length 9A and second lumen length 9B may be different. This may be advantageous in certain medical contexts where a first lumen expels fluid and a second lumen withdraws fluid, and co-location of distal lumen ends 3A and 3B could result in undesirable recirculation effect. For example, dialysis catheters typically have a shorter "arterial" lumen 4B that withdraws blood and a longer "venous" lumen that returns filtered blood back to the bloodstream. Because the distal end 3B shorter arterial lumen is upstream of the distal end 3A of the longer venous lumen when implanted, the likelihood of the arterial lumen withdrawing already-filtered blood expelled by the venous lumen is advantageously reduced. The length 9B of shorter arterial lumen typically is typically between 2 cm to 4 cm shorter than the length 9A of the longer venous lumen. Commonly, the difference between 9A and 9B is approximately 3 cm. Thus, with reference to the exemplary ranges of lengths 9B, 103, 102, and 108 above, and the table of FIG. 20, in some embodiments exemplary insertable lengths 101 for the shorter lumen may range from 25.5 cm to 76.4 cm. Thus, in embodiments pertaining to certain types of dialysis catheters, insertable lengths 101 can generally range from approximately 25 cm to 80 cm.

Stopper 20 can be manufactured from plastic, rubber, silicone, metal, other materials known to persons of skill in the art, and/or combinations thereof. It may resemble, for example, a bead, a cylinder (as depicted in FIG. 1), a cone, or any other shape or form known to persons of skill in the art, so long as stopper 20 (i) cannot be moved along cable 10 when it is attached, (ii) cannot pass through fiber insertion port 71, and (iii) does not compromise the ability of fiber optic cable 10 to propagate UV light. In certain embodiments, stopper 20 may be (or may be similar to) a torque device, which is a commercially available device commonly used for gripping and steering guide wires in the medical context. Certain commercially available torque devices may be threaded onto fiber optic cable 10 and may be affixed by screwing together torque device components. For example, stopper 20 may contain first and second components with hollow centers, both of which may threaded onto the fiber; the first component may comprise a compressing portion, and the second component, may be designed to screw onto the compression portion, such that when the second part is screwed tighter, the compressing portion securely grips fiber optic cable 10. Other commercially available torque devices may be threaded onto fiber optic cable 10 and may be affixed by snapping together torque device components (which may or may not be hinged). In other embodiments, stopper 20 can be a hinged device or a two-part apparatus without a threading component that may be securely clamped onto fiber optic cable 10, wherein the internal portion of stopper 20 may comprise rubber or another material to securely grip fiber optic cable 10. In yet other embodiments, stopper 20 may be glued onto fiber optic cable 10, or stopper 20 may, itself, be a bead of silica, plastic, resin, epoxy, or other material affixed to or integrally formed with fiber optic cable 10 during, for example, manufacture.

FIG. 2C illustrates a cross-section of fiber optic cable 10 including fiber jacket 17. In some embodiments, the diameter of fiber jacket 17 may preclude it from passing through fiber insertion port 71. This may serve as a failsafe for stopper 20. Or, in certain embodiments, the distal-most edge of fiber jacket 17 may act as (and replace) stopper 20, limiting the range of movement of fiber optic cable 10. In such embodiments, the length of fiber optic cable 10 beyond to the distal-most edge of fiber jacket 17 can be insertable length 101.

Referring back to FIG. 1, exemplary UV light-based sterilization system 100 includes UV light base unit 60, which may include UV light source 62, controlled by controller 90, which in turn may contain timer 91. The person of ordinary skill in the art that controller 90 is not limited to a single processor, single microchip, or any other particular hardware configuration; rather controller 90 contemplates any hardware and/or software configuration suitable to performing the functions of controller 90, whether or not the hardware and/or software configuration components additionally serve other functions. In some embodiments, some functions of controller 90 discussed herein may be performed by an electronic device, such as a computer, tablet, or smart phone, connected to UV light base unit 60. UV light source 62 may provide UVC radiation, which includes a wavelength range between 240 and 280 nm.

In preferred embodiments, UV light source 62 can be a UV laser (or a plurality of UV lasers) that work by, for example, frequency doubling laser light to UVC wavelengths using nonlinear optical processes. For example, UV light source 62 may be a laser-diode pumped solid state UV laser with output power between 1-50 mW and an output wavelength of approximately 266 nm. In other embodiments, the UV laser may have output power of up to 100 mW or more. The laser can be a Q-switched pulsed laser with pulse duration of 7 ns. UV lasers of this type may be sufficiently portable, powerful enough to sterilize catheters in relatively short periods of time (for example, on the order of minutes or tens of minutes), and may be relatively inexpensive.

In some circumstances, exposure to UV light with certain modulated intensities has been shown to achieve increased effectiveness in killing bacteria than unmodulated UV light. As such, UV light source 62 may also emit UV light with modulated intensity, such as, for example pulsing UV light or waveform UV light, as directed by controller 90. For example, the UV light may be modulated with waveforms provided to UV light source 62 via electronic signals from controller 90. Thus, in certain preferred embodiments, controller 90 may direct UV light source 62 to modulate UV light. UV light may be modulated in accordance with waveforms such as pulses, square waveforms, sinusoidal waves, combined waveforms, or other, more customized, waveforms. For example, these waveforms can be square waves with frequencies from 1 to 1000 Hz and duty cycles ranging from 25% to 75%, which have been shown to improve killing microbes in biofilm in Li et al. (2010), Enhanced Germicidal Effects of UV-LED Irradiation on Biofilms, *Journal of Applied Microbiology* 109, 2183-90. In one embodiment, the UVC intensity can be square wave-modulated at 100 Hz with a duty cycle of 75% to achieve improved bacterial killing over that of unmodulated UVC intensity.

In other embodiments, UV light source 62 may comprise one or more UV LEDs (e.g., LEDs comprising AlGaN), UV light-emitting mercury lamps, and/or UV eximer lasers. While UV LEDs may be relatively small and power efficient, they supply a limited amount of UV light per unit area when compared to a UV laser. Mercury lamps may beneficially provide UV light with a spectral line at 254 nm, but they are bulky and inefficient, and supply only a limited amount of UV light per unit area. While UV eximer lasers may be sufficiently powerful, their high cost may preclude their widespread use in the field of in vivo catheter sterilization. In other embodiments, UV light source 62 may comprise a high-powered UV radiation source that might not be commercially available at the time of this disclosure, such as, for example, UV laser diodes capable of emission in the UVC light band.

Despite that exemplary embodiments discussed herein refer to light source 61 as UV light source 62, this disclosure contemplates that light source 62 need not be limited to light sources in the UVC band or even the UV band, so long as light source 62 propagates radiation with antimicrobial properties. For example, blue light in the range of 405-470 nm has been found to have bactericidal effects. Thus, in certain embodiments of system 100, light source 62 can provide antimicrobial blue light or other antimicrobial light outside of UV wavelengths, either in conjunction with or exclusive to UV light. The person of ordinary skill in the art would understand that disclosed teachings pertaining to UV light can be applied to other types antimicrobial light.

UV light source 62 propagates UV light to fiber optic cable 10 via UV transmitting cable 61, which terminates at fiber optic port 63. Where UV light source 62 is a laser, the laser output beam is preferably aligned with the optical fiber core of UV transmitting cable 61 to allow the maximum UV power to be coupled into the fiber. Fiber optic port 63 engages with and optically couples to fiber optic connector 13 of fiber optic cable 10. In certain embodiments, fiber splitter 82 may be included along UV transmitting cable 61 such that detector 80 may detect and measure levels of light (i) transmitted by UV light source 62 via light source detection cable 83 and/or (ii) reflected back from the distal end of fiber optic cable 10 via reflection detection cable 81. Controller 90 may receive and process both transmission and reflection data from detector 80. Further, controller 90 may provide information and receive instructions from an operator (typically, a doctor, nurse, or other medical professional) via user interface 92. User interface 92 may include some or all of a display, lights, a speaker, buttons, a keyboard, a microphone, and a touch screen. User interface 92 may also include wired and wireless technologies (e.g., Bluetooth and/or Wifi) sufficient to connect with other electronic devices, such as computers, tablets, smart phones, and smart watches, so that the electronic devices may perform some functions of user interface 92 and/or download data from UV light base unit 60.

Dynamic UV Light-Based Sterilization

In preferred embodiments of UV light-based sterilization system 100, fiber optic cable 10 may be either dynamic fiber optic cable 30 to effectuate dynamic UV light-based sterilization techniques or static fiber optic cable 40 to effectuate static UV light-based sterilization techniques. In dynamic UV light-based sterilization techniques, UV light is largely radiated from light-scattering tip 31 at distal end 12 of dynamic fiber optic cable 30. UV light may be scattered from tip 31 radially and/or in the forward direction. (Some UV light may also be backreflected through dynamic fiber optic cable 30, which may, in turn be detected and measured by detector 80.) Thus, in order to effectively sterilize catheter 1, light-scattering tip 31 of dynamic fiber optic cable 30 may effectively be moved through the full length of catheter 1 as tip 31 scatters UV light. By contrast, in static UV light-based sterilization techniques, UV light is radially scattered toward the walls of catheter 1 along, for example, the portion of static fiber optic cable 40 that may fit within catheter 1, insertable length 101, and/or the portion of cable 40 distal to stopper markings 21.

In dynamic UV light-based sterilization techniques, dynamic fiber optic cable 30 may be moved manually, e.g., hand-drawn by an operator. In other embodiments, for example, as discussed later in this disclosure, dynamic fiber optic cable 30 movement may be automatically controlled in whole or part. Automatic dynamic UV light-based sterilization may be more accurate, may be more repeatable, may reduce likelihood of operator error, may reduce risk of localized over-radiation or heating of a portion of catheter 1 and surrounding tissue, and may provide for additional feedback and measurements when compared manual dynamic UV light-based sterilization. However, due to the additional complexity and instrumentalities of automatic dynamic UV light-based sterilization systems, manual dynamic UV light-based sterilization systems may be less expensive to manufacture, purchase, maintain, and operate; may be lighter and more portable; and, in some embodiments, may be simpler to operate.

Figure 3:
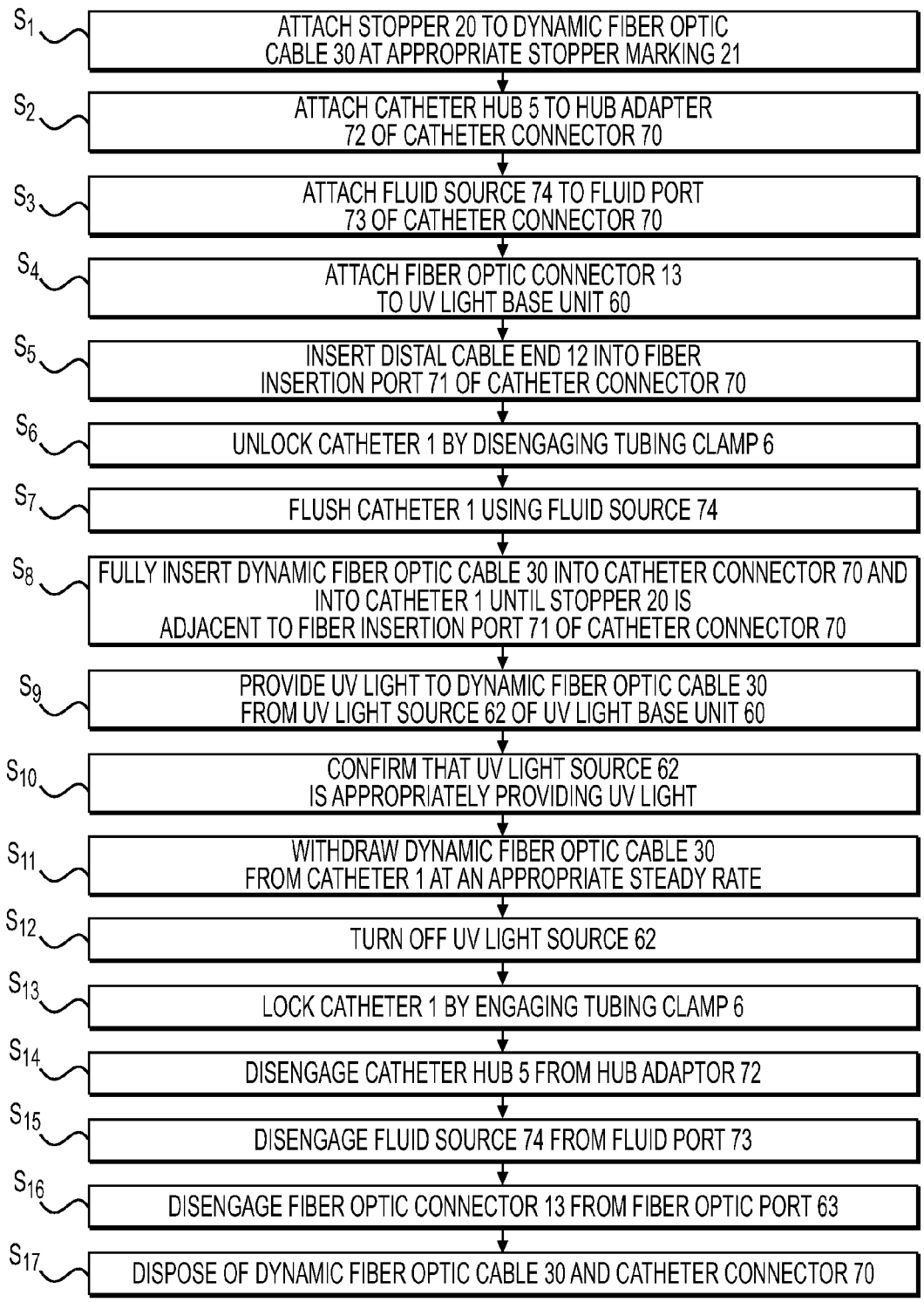
FIG. 3 is a flow chart illustrating a method of dynamic UV light-based sterilization, according to at least one aspect of the disclosure.

FIG. 3 is a flow chart illustrating an exemplary method of dynamic UV light-based sterilization. While some steps of FIG. 3 are discussed with reference to being directly performed by an operator, such steps may be performed by a device under the control of the operator.

As in step S1, the operator may attach stopper 20 to dynamic fiber optic cable 30 after aligning stopper 20 on an appropriate stopper marking 21. In other embodiments, step S1 may be omitted. For example, as referenced above, models of fiber optic cable 10 (including dynamic fiber optic cable 30 and static fiber optic cable 40) may be manufactured and sold such that fiber jacket 17 serves as stopper 20. As another example, models of fiber optic cable 10 may be manufactured and sold with stopper 20 already attached or integrally included at a position corresponding to particular catheter 1 lengths or models. As yet another example, step S1 may be omitted where the position of distal cable end 12 is to be tracked and controlled using other techniques, including monitoring the position of markings (including stopper markings 21) on fiber optic cable 10, monitoring light reflected back through fiber optic cable 10 to detector 80, monitoring the position of a radiopaque fiber tip 31 of fiber optic cable 10, and/or other techniques disclosed herein.

As in step S2, the operator may attach catheter hub 5 to hub adapter 72 of catheter connector 70.

As in step S3, the operator may attach fluid source 74 to fluid port 73 of catheter connector 70.

As in step S4, the operator may attach fiber optic connector 13 to fiber optic port 63 of UV light base unit 60.

As in step S5, the operator may insert distal cable end 12 into fiber insertion port 71 of catheter connector 70. It should be noted that dynamic catheter sterilization may proceed effectively even if the order of steps S1 through S5 is altered. It should also be noted that steps S4 and S5 can take place after steps S6 and/or S7 in alternative embodiments.

As in step S6, the operator may then unlock catheter 1 by disengaging tubing clamp 6.

As in step S7, the operator may then flush catheter 1 with a fluid, such as saline solution, from fluid source 74. One purpose of flushing catheter 1 is to clear lumen 4 of blood, debris, and other non-UV transparent material prior to the insertion of the fiber optic cable. Blood, debris, or other non-UV transparent material remaining in lumen 4 during the provision of UV light (e.g., step S9) may undermine the UV light-based sterilization techniques disclosed herein by absorbing UV light or otherwise preventing UV light from reaching some or all areas of catheter 1 at power levels sufficient for sterilization.

In certain embodiments, the saline solution may further contain antibiotics or antiseptics to aid in sterilization; materials that may aid in the loosening or deterioration of biofilm; or other materials that form a part of the patient's medical treatment. Alternatively, another biocompatible fluid that would allow UV light to sufficiently reach to the walls of catheter 1 may be used to flush catheter 1. For example, in certain embodiments, the flushing fluid may comprise material that dissolves blood and/or blood clots, such as heparin or a thrombolytic such as tPA, such that obstructive blood or adherent blood clots may removed from catheter lumen 4. Or, in other embodiments, the fluid may be hypotonic or hyperosmotic, such that red blood cells in catheter 1 may burst or shrink, respectively, in order to make red blood cells easier to flush out of catheter 1. Further, in other embodiments, flushing may be repeated, for example, with different flushing fluids.

In alternative embodiments, prior to flushing the catheter, an operator may use a syringe or other suction device to withdraw any fluid within catheter 1. Adding such a step can help avoid flushing of undesirable materials, including, for example loose biofilm, blood clots, antibiotic lock fluids, or anti-clotting fluids (for example, heparin or citrate) in to the blood stream. The withdrawn fluid can be disposed of. The suction device can be engaged with fluid port 73 in step S3, and then replaced with fluid source 74 after fluid is withdrawn, but before step S7. In such embodiments, tubing clamp 6 should be disengaged prior to fluid withdrawal and reengaged before removing the suction device from fluid port 73.

As in step S8, the operator may then push dynamic fiber optic cable 30 through catheter connector 70 and into catheter 1 until stopper 20 is adjacent to fiber insertion port 71 of catheter connector 70.

As in step S9, the operator may then direct UV light base unit 60 to provide UV light to dynamic fiber optic cable 30 from UV light source 62. In certain embodiments the UV light may be modulated to effectuate more effective microbial killing and/or can be an antimicrobial light that is not UV, as discussed above. Additionally, UV light base unit 60 may provide a visual cue (such as a light turning on) or auditory cue (such as a bell or buzzing sound) via user interface 92 indicating that UV light source 62 is on.

As in step S10, the operator may then confirm that UV light source 62 is appropriately providing UV light. As UV light is not visible to the naked eye, UV light base unit 60 may use detector 80 to confirm that UV light source 62 is appropriately emitting UV light. For example, fiber splitter 82 may direct a fraction of light received from UV light source 62 along UV transmitting cable 61 to detector 80 via light source detection cable 83. In turn, detector 80 may provide data regarding the received light to controller 90 to evaluate whether or not UV light source 62 is working properly. Controller 90 may inform the operator of that status via user interface 92. Additionally, based on the data from detector 80, controller 90 may adjust the power directed to UV light source 6 to adjust UV light to an appropriate power level in a feedback loop. This is a means for adjusting the power of the UV light as needed for dose control and for safety.

In another embodiment, detector 80 indirectly measures the output of UV light source 62 by using backreflectance of light transmitted bank and forth through optical fiber 10. For example, fiber splitter 82 may direct a of fraction of light received from optical fiber 10 along UV transmitting cable 61 to detector 80 via reflection detection cable 81. In turn, detector 80 may provide data regarding the received light to controller 90 to evaluate whether or not UV light source 62 is working properly. Controller 90 may inform the operator of that status via user interface 92. Additionally, based on the data from detector 80, controller 90 may adjust the power directed to UV light source 6 to adjust UV light to an appropriate power level in a feedback loop. This is another means for adjusting the power of the UV light as needed for dose control and for safety.

In yet another embodiment, UV light source 62 may emit visible optical wavelengths along with its emission of light at invisible, UVC wavelengths. Detector 80 may measure the power of these visible wavelengths indirectly through backreflectance measurements or directly via light source detection cable 83, controller 90 may inform the operator of the status via user interface 92, and/or controller 90 may effectuate a feedback loop based on the measurements, all in a fashion similar to the embodiments discussed above. However, the inclusion of visible optical wavelengths in the output of UV light source 62 may have the additional benefits of directly indicating to the operator—without relying on user interface 92—that the UV light is on. Further the inclusion of a visible optical wavelengths provides an additional measure of safety as it provides a means for determining the direction of optical output; the visible light can be used identify a dangerous scenario where the UV beam is directed towards a patient's or operator's eye.

In certain embodiments, fiber optic cable 10 may be selected such that it radially emits visible light as it propagates UV light provided by UV light source 62—even when UV light source 62 does not emit light (or substantial amounts of light) at a visible-spectrum wavelength. For example, cladding 15 and/or buffer 16 may be impregnated with fluorescent compounds, such as, for example commercially available quantum dots or florescent dyes or powders, like fluorescin. This is a safety mechanism.

As in step S11, the operator may withdraw dynamic fiber optic cable 30 from catheter 1 at an appropriate steady rate—by hand (i.e., manually) or with the aid of a device (e.g., automatically). An appropriately steady rate contemplates moving light-scattering tip 31 at a speed such that the entirety of lumen 4 of catheter 1 is exposed to sufficient UV light as to adequately sterilize catheter 1.

In exemplary embodiments, the withdrawal of fiber optic cable 10 should stop when light-scattering tip 31 is located within catheter connector 70. Stopping the withdrawal step after light-scattering tip 31 enters catheter connector 70 provides additional assurance that all of lumen 4, as well as inner surfaces of catheter hub 5, have been treated with UV light. Stopping the withdrawal step before light-scattering tip 31 leaves the catheter connector 70 improves safety because UV light emitted by light-scattering tip 31 can be prevented from escaping into the surrounding environment by a UV opaque catheter connector 70.

Assuming a steady withdrawal rate, that light-scattering tip 31 is perfectly parallel to the catheter axis, that light-scattering tip 31 is centrally positioned, and an even distribution of light from light-scattering tip 31, all portions of catheter 1 may be equally exposed to UV light emanating from light-scattering tip 31. Under this assumption, the maximum theoretical UV dose per unit surface area can calculated from the UV light exposure time, the area of lumen 4, and UV light power exiting the optical fiber. That is:

$$\text{Dose}(mJ/cm^2) = \text{Power}(mW) * \text{Time}(s) / \text{Area}(cm^2)$$

Further:

$$\text{Area}(cm^2) = \text{Length}(cm) * \text{Circumference}(cm) = \text{Length}(cm) * \text{Diameter}(cm) * \pi$$

Therefore:

$$\text{Dose}(mJ/cm^2) = \text{Power}(mW) * \text{Time}(s) / (\text{Length}(cm) * \text{Diameter}(cm) * \pi)$$

And the appropriate steady rate may be calculated as follows:

$$\text{Rate}(cm/s) = \text{Length}(cm)/\text{Time}(s) = \text{Power}(mW)/(\text{Dose}(mJ/cm^2) * \text{Diameter}(cm) * \pi)$$

The time it would take to withdraw dynamic fiber optic cable 30 at the appropriate steady rate may be calculated as follows:

$$\text{Time}(s) = \text{Dose}(mJ/cm^2) * \text{Length}(cm) * \text{Diameter}(cm) * \pi / \text{Power}(mW)$$

This may also be expressed at time per unit length:

$$\text{Time per unit length}(s/cm) = \text{Dose}(mJ/cm^2) * \text{Diameter}(cm) * \pi / \text{Power}(mW)$$

The required UV radiation dose for sterilization of an infected catheter 1 may be much higher than a UV radiation dose given as a prophylactic measure to prevent catheter 1 infections. And sufficient dose values for catheter sterilization may be determined experimentally based on a variety of factors, including whether and how UV light is modulated, the severity of the infection (or lack thereof), the type of catheter 1, and the UV light scattering properties of fiber optic cable 10. It may be noted that due to inherent inaccuracies in the assumptions, the actual delivered dose will be lower than the assumed (i.e., theoretical) dose. This, however, does not undermine the calculations where the assumed dose is used in both experimental calculations and in determining the appropriate steady rate (or time required for static UV light-based sterilization).

For example, an assumed dose of unmodulated UV light of 750 mJ/cm$^2$ may be sufficient to sterilize an infected, 20 cm hemodialysis catheter (a type of CVC catheter) lumen with an inner diameter of 1.7 mm. If dynamic fiber optic cable can be provided with 20 mW of UV light, the appropriate steady rate may be calculated as follows:

$$\text{Rate(cm/s)} = \text{Power(mW)}/\text{Dose(mJ/cm}^2)*\text{Diameter(cm)}*\pi$$

$$\text{Rate(cm/s)} = 20 \text{ mW}/750 \text{ mJ/cm}^2 * 0.17 \text{ cm} * \pi = 0.05 \text{ cm/s}$$

And the total time of sterilization may be calculated as follows:

$$\text{Time(s)} = \text{Dose(mJ/cm}^2)*\text{Length(cm)}*\text{Diameter(cm)}*\pi/\text{Power(mW)}$$

$$\text{Time(s)} = 750 \text{ mJ/cm}^2 * 20 \text{ cm} * 0.17 \text{ cm} * \pi/20 \text{ mW} = 400 \text{ seconds}$$

And the time per unit length may be calculated as follows:

$$\text{Time per unit length(s/cm)} = \text{Dose(mJ/cm}^2)*\text{Diameter(cm)}*\pi/\text{Power(mW)}$$

$$\text{Time per unit length(s/cm)} = 750 \text{ mJ/cm}^2 * 0.17 \text{ cm} * \pi/20 \text{ mW} = 20 \text{ seconds/cm}$$

An operator may manually achieve an appropriate steady rate by using a ruler, measuring tape, or the like; and a time-keeping device, such as a timer, clock, or stopwatch. In some embodiments, dynamic fiber optic cable 30 may include equally spaced readable marks that an operator can use in lieu of a ruler. The readable marks may comprise ink-based or laser-scored rings on the outermost surface of cable 30 along its length, at least between stopper 20 or stopper marker 21 and distal catheter end 4. For example, dynamic fiber optic cable 30 may include one readable mark every 1 cm, every 1 inch, or every half-inch along its insertable length 101. An operator can observe each readable mark as it passes out of catheter connector 70. In other embodiments, the distance between each equally spaced readable mark can correspond with the distance that the operator should withdraw cable 30 each second, each half-second, or another time period in order to achieve delivery of a particular dose.

In alternative embodiments, dynamic fiber optic cable 30 may include readable marks that are not evenly spaced, which can be used to provide non-uniform doses along the length of catheter 1 when an operator withdraws cable 30 the length of the distance between two sequential readable marks per second (or other time period). The provision of non-uniform doses along the length of catheter 1 may be acceptable or even desired in some embodiments because catheters may, in some circumstances, have a tendency to have greater biofilm infection toward their proximal ends as shown in Ramanathan, V. et al. (2012), Characteristics of Biofilm on Tunneled Cuffed Hemodialysis Catheters in the Presence and Absence of Clinical Infection. *American Journal of Kidney Disease* 60:6, 976-82.

Finally, it should be noted that if catheter 1 (and/or catheter connector 70) is not UV opaque, additional precautions must be taken during dynamic fiber optic cable withdrawal to avoid unnecessary UV radiation exposure outside of UV light-based sterilization system 100 once light-scattering tip 31 enters the proximal portion of catheter 1 that is not in the patient's body. For example, the entirety of the exposed portion of catheter 1 (and/or catheter connector 70) may be covered with a UV-opaque layer (preferably an easily-applicable tape, film, or wrap, such as acrylic tape) that is preferably transparent to visible light such that the operator may continue to observe dynamic fiber optic cable 30 within catheter 1.

As in step S12, the operator may then direct UV light base unit 60 to turn off UV light source 62. In order to avoid unnecessary UV radiation exposure outside of UV light-based sterilization system 100, the step of turning off UV light source 62 should occur before the removal of UV light-scattering tip 31 of dynamic fiber optic cable 30 from catheter connector 70 (which is an optional step, not shown in FIG. 3). In exemplary embodiments, UV light source 62 should be turned off while light-scattering tip is located within catheter connector 70.

As in step S13, the operator may then lock catheter 1 by engaging tubing clamp 6.

As in step S14, the operator may then disengage catheter hub 5 from hub adaptor 72.

As in step S15, the operator may then disengage fluid source 74 from fluid port 73.

As in step S16, the operator may then disengage fiber optic connector 13 from fiber optic port 63. It should be noted that dynamic catheter sterilization may proceed effectively even if the order of steps S14 through S16 is altered.

As in step S17, the operator may then dispose of dynamic fiber optic cable 30 and catheter connector 70. Generally, fiber optic cable 10 should not be reused for cleanliness and sterility reasons. However, in certain circumstances, it may be acceptable to reuse the same fiber optic cable 10 to immediately re-sterilize the same catheter 1, to serially sterilize each lumen 4 in a multi-lumen catheter in rapid sequence, to serially sterilize multiple catheters in the same patient in rapid sequence, or in similar circumstances.

In other, alternative embodiments of dynamic UV light-based sterilization techniques, dynamic fiber optic cable 30 may by slowly inserted into (rather than withdrawn from) catheter 1 at the appropriate steady rate as tip 31 scatters UV light. In such embodiments, the UV light source is preferably turned on after the light-scattering tip 31 has been inserted into, and still located within, the catheter connector 70.

Figure 4G:
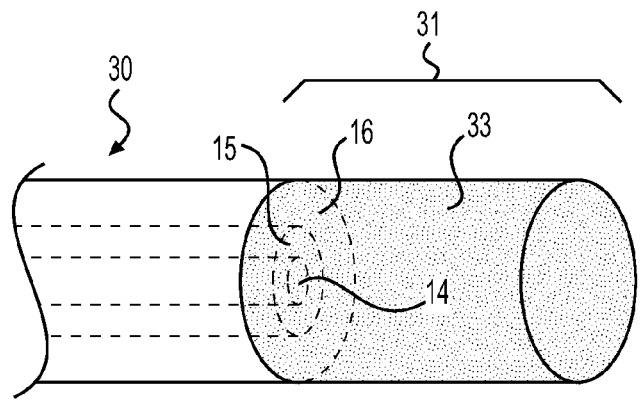

FIGS. 4A-4I illustrate different embodiments of light-scattering tips 31 of dynamic fiber optic cables 30. FIG. 4A depicts light-scattering tip 31 wherein core 14, cladding 15, and buffer 16 are cut off, forming a flat tip. In some embodiments the flat tip may be roughened to increase scattering.

FIG. 4B depicts an embodiment of light-scattering tip 31 wherein buffer 16 is stripped away, leaving cladding tip 31 surrounding core 14, and wherein cladding 14 is mechanically roughened. In certain embodiments buffer 16 may be stripped using a fiber stripper and/or cladding 14 may not be roughened.

FIG. 4C depicts an embodiment of light-scattering tip 31 wherein core 14, cladding 15, and buffer 16 are cut off at an angle with respect to fiber optic cable 30. In such an embodiment, light-scattering tip 31 may substantially direct UV light to a particular radial segment of catheter 1. In order to have 360-degree exposure of UV radiation of catheter 1, dynamic fiber optic cable 30 may be spun as it is withdrawn from lumen 4, thereby causing continuous and 360 degree exposure of lumen 4 of the catheter to UV light.

FIG. 4D depicts an embodiment of light-scattering tip 31 wherein cladding 15 and buffer 16 are stripped away, by chemical means and/or mechanical means, leaving only core 14.

FIG. 4E depicts an embodiment of light-scattering tip 31 in a cone shape, which may direct UV light radially, but may result in substantial backreflectance.

FIG. 4F depicts an embodiment of light-scattering tip 31 wherein dome-shaped lens 32 is affixed to the end of dynamic fiber optic cable 30. Dome-shaped lens 32 may scatter UV light radially towards the walls of lumen 4.

Figure 4H:
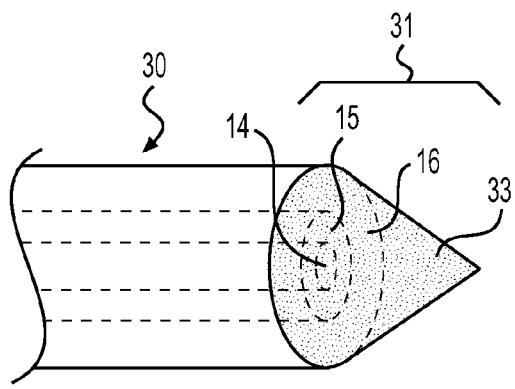

FIGS. 4G and 4H depict embodiments of light-scattering tip 31 wherein light diffusor 33 is affixed to the end of dynamic fiber optic cable 30. Light diffusor 33 may comprise, for example, ground glass or other inhomogeneous UV transparent materials, and may effectively scatter light transmitted by dynamic fiber optic cable 30.

Figure 4I:
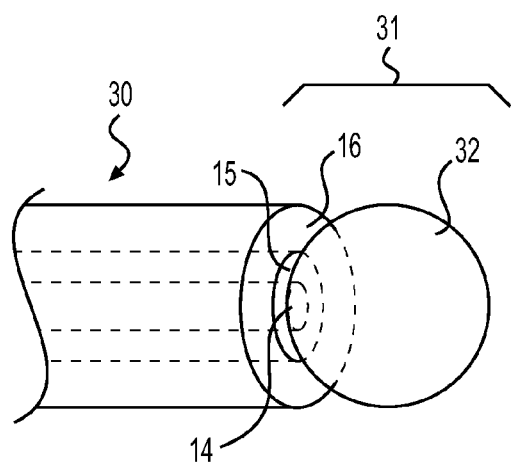

FIG. 4I depicts an embodiment of light-scattering tip 31 wherein spherical-shaped lens 32 (e.g., a ball lens) is affixed to the end of dynamic fiber optic cable 30. Spherical-shaped lens 32 may scatter UV light radially towards the walls of lumen 4. It may also be a light diffusor.

In other embodiments, light-scattering tip 31 may be polished. In yet other embodiments, light-scattering tip 31 may contain imperfections and non-uniformities, or may be scored by chemical, mechanical, and/or laser means.

In alternative embodiments, a thin cable sheath may be included around at least a portion of fiber optic cable 30 to protect light-scattering tip 31 during the insertion of cable 30 into catheter 1. Specifically, the cable sheath can further reduce any possibility that debris within the catheter might occlude, block, or otherwise adversely affect emissions of light-scattering tip 31 of the optical fiber. In practice, a sheathed cable 30 is inserted into the catheter with the sheath surrounding, and perhaps extending slightly beyond, distal cable end 12. When distal cable end 12 and the distal portion of the sheath assembly reach the desired distal position within the catheter 1, the sheath can be withdrawn back by a predetermined length, thereby exposing the light emitting tip 31 to the catheter lumen 4. Catheter sterilization can then proceed as disclosed in other embodiments discussed herein. The sheath can be made of various materials known the persons having ordinary skill in the art, including polyurethane, polyethylene, and ETFE.

Figure 5:
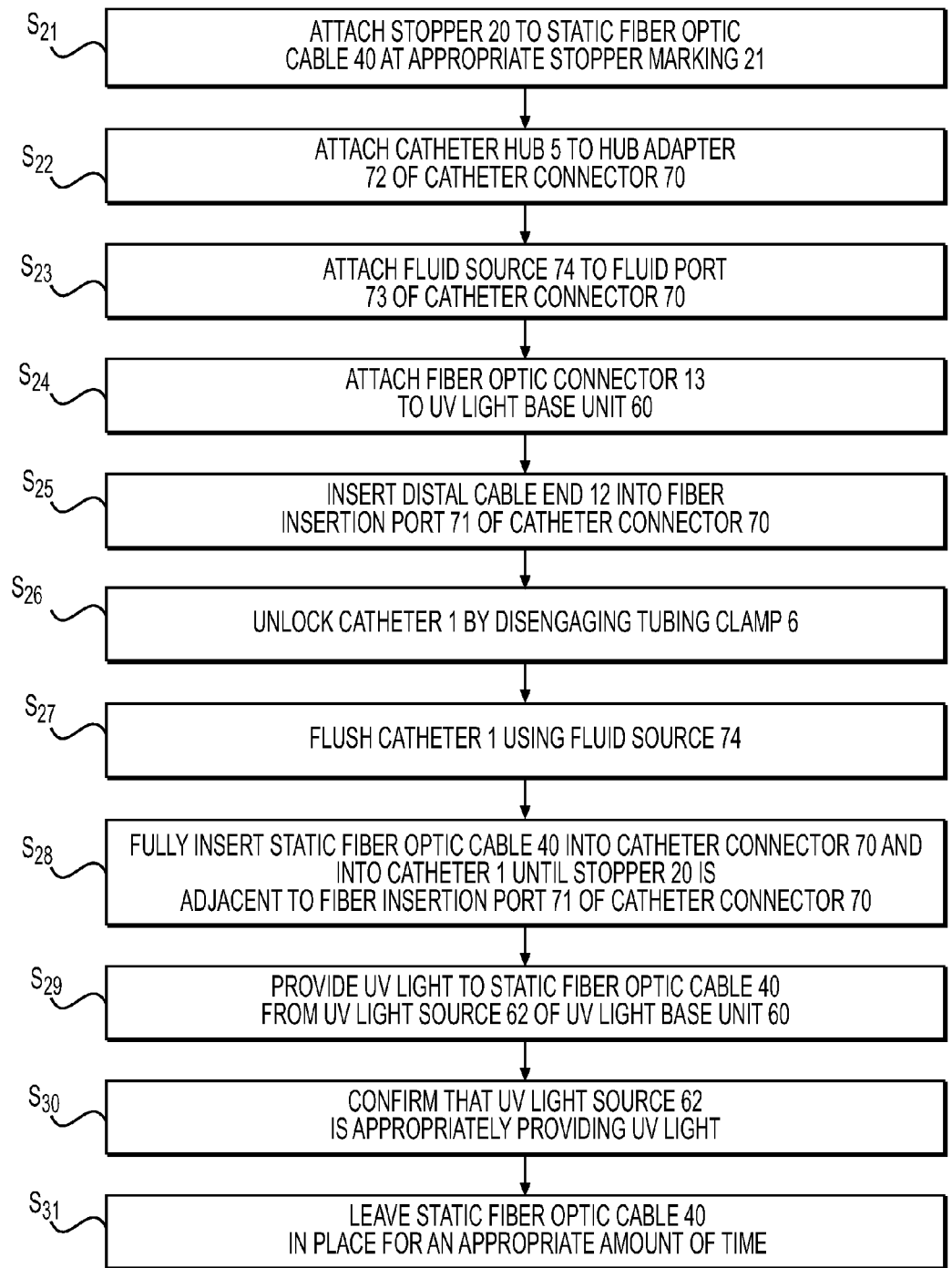
FIG. 5 is a flow chart illustrating a method of static UV light-based sterilization, according to at least one aspect of the disclosure.
Figure 5:
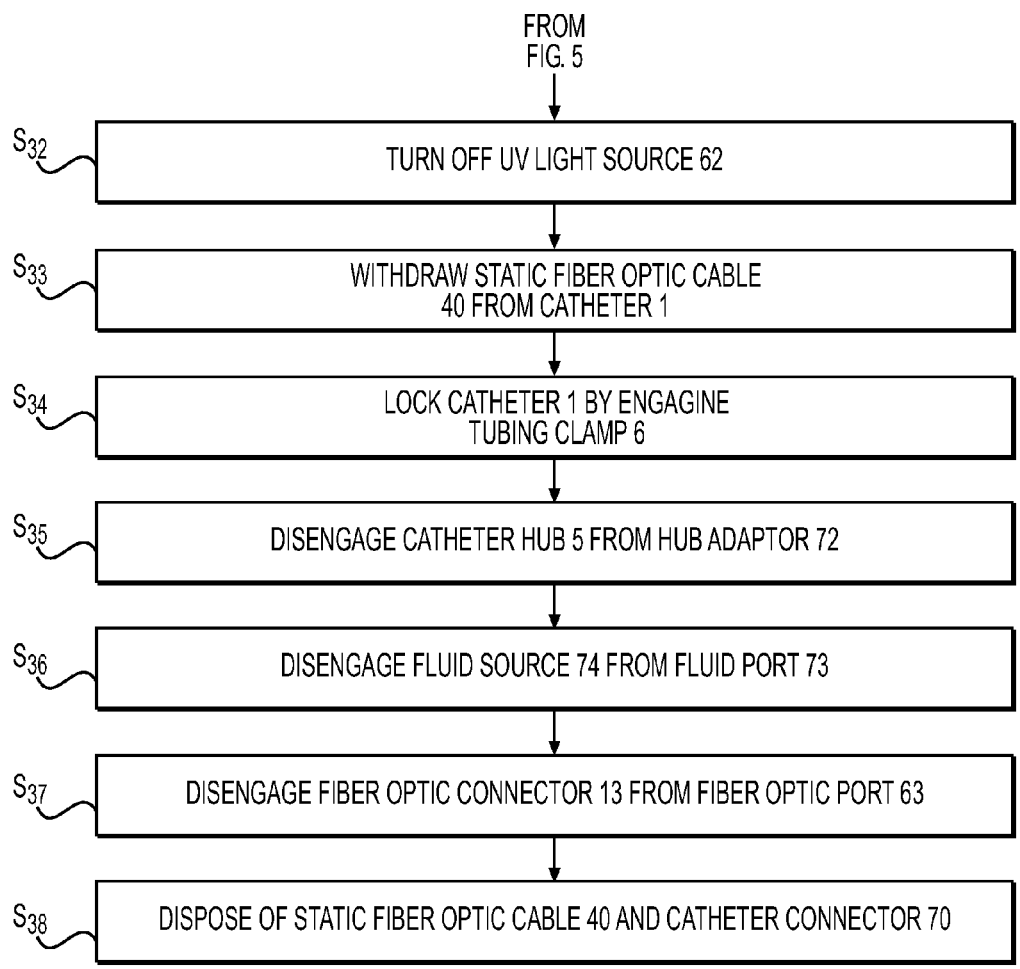

FIG. 5 is a flow chart illustrating an exemplary method of static UV light-based sterilization. While some steps of FIG. 5 are discussed with reference to being directly performed by an operator (e.g., a doctor, nurse or other medical professional), such steps may be performed by a device under the control of the operator.

As in step S21 (parallel to step S1), the operator may attach stopper 20 to static fiber optic cable 40 at appropriate stopper marking 21.

As in step S22 (parallel to step S2), the operator may attach catheter hub 5 to hub adapter 72 of catheter connector 70.

As in step S23, (parallel to step S3), the operator may attach fluid source 74 to fluid port 73 of catheter connector 70.

As in step S24 (parallel to step S4), the operator may attach fiber optic connector 13 to fiber optic port 63 of UV light base unit 60.

As in step S25 (parallel to step S5), the operator may insert distal cable end 12 into fiber insertion port 71 of catheter connector 70. It should be noted that static catheter sterilization may proceed effectively even if the order of steps S21 through S25 is altered. It should also be noted that steps S24 and S25 can take place after steps S26 and/or S27 in alternative embodiments.

As in step S26 (parallel to step S6), the operator may then unlock catheter 1 by disengaging tubing clamp 6.

As in step S27 (parallel to step S7), the operator may then flush catheter 1 with a fluid, such as saline solution, from fluid source 74. As discussed above with reference to step S7, fluid may be withdrawn from the catheter before the flushing step.

As in step S28, (parallel to step S8), the operator may then push static fiber optic cable 40 through catheter connector 70 and into catheter 1 until stopper 20 is adjacent to fiber insertion port 71 of catheter connector 70. Additionally, precautions may need to be taken to avoid unnecessary UV radiation exposure outside of UV light-based sterilization system 100 once UV light source 62 is turned on. For example, in some embodiments, all portions of static fiber optic cable 40 proximal to stopper 20 and not covered by fiber jacket should be covered with a UV-opaque layer (which preferably is transparent to visible light). Alternatively, exposed portions of static fiber optic cable 40 may simply be covered during UV light transmission. Further, if catheter 1 (and/or catheter connector 70) is not UV opaque, the entirety of the exposed portion of catheter 1 (and/or catheter connector 70) should also be UV shielded.

As in step S29 (parallel to step S9), the operator may then direct UV light base unit 60 to provide UV light to static fiber optic cable 40 from UV light source 62.

As in step S30 (parallel to step S10), the operator may then confirm that UV light source 62 is appropriately providing UV light. It may be noted that static sterilization steps S21-30 correspond directly to dynamic sterilization steps S1-10, respectively.

As in step S31, the operator may leave static fiber optic cable 40 in place for an appropriate amount of time. Assuming the same UV dose, UV light power, and catheter dimensions, the appropriate amount of time for static fiber optic cable 40 to be left in place in static UV light-based sterilization should be similar to the amount of time required for withdrawal of dynamic fiber optic cable 30 at the appropriate steady rate in dynamic UV light-based sterilization (as discussed above with respect to step S11):

$$\text{Time(s)} = \text{Dose(mJ/cm}^2) * \text{Length(cm)} * \text{Diameter(cm)} * \pi / \text{Power(mW)}$$

Further, assuming even UV power distribution along static fiber optic cable 40, each portion of catheter 1 may be radiated with substantially the same desired dose. But if this assumption does not hold, the UV radiation dose may be higher in some segments of catheter 1 and lower in others, consistent with the following formula:

$$\text{Power per unit length(mW/cm)} = \text{Dose(mJ/cm}^2) * \text{Diameter(cm)} * \pi / \text{Time(s)}$$

The provision of non-uniform doses along the length of catheter 1 may be acceptable or even desired in some embodiments because catheters may, in some circumstances, have a tendency to have greater biofilm infection toward their proximal ends as shown in Ramanathan, V. et al. (2012), Characteristics of Biofilm on Tunneled Cuffed Hemodialysis Catheters in the Presence and Absence of Clinical Infection. *American Journal of Kidney Disease* 60:6, 976-82.

Further, it may be noted that, where UV light source 62 provides power at very high levels, thereby reducing the appropriate amount of time to effectuate a particular UV dose, static sterilization techniques may be preferred over dynamic sterilization techniques. This is because whereas static fiber optic cable 40 continuously diffuses the UV light along the entirety of catheter 1, dynamic fiber optic cable 30 focuses the UV light on particular regions as it is withdrawn. At high power levels, the intensity of the focused UV light (or resulting heat) may damage catheter 1 or the surrounding tissue.

As in step S32 (parallel to step S12), the operator may then direct UV light base unit 60 to turn off UV light source 62.

As in step S33, the operator may then withdraw static fiber optic cable 40 from catheter 1. For static sterilization techniques, it is particularly important to turn off UV light source 62 before beginning to withdraw static fiber optic cable 40 from catheter 1 to avoid unnecessary UV radiation exposure due to static fiber optic cable 40's radial scattering of UV light.

As in step S34 (parallel to step S13), the operator may then lock catheter 1 by engaging tubing clamp 6.

As in step S35 (parallel to step S14), the operator may then disengage catheter hub 5 from hub adaptor 72.

As in step S36 (parallel to step S15), the operator may then disengage fluid source 74 from fluid port 73.

As in step S37, (parallel to step S16), the operator may then disengage fiber optic connector 13 from fiber optic port 63. It should be noted that static catheter sterilization may proceed effectively even if the order of steps S35 through S37 is altered.

As in step S38, (parallel to step S17), the operator may then dispose of static fiber optic cable 40 and catheter connector 70. It may be noted that static sterilization steps S32 and S34-38 correspond directly to dynamic sterilization steps S12-17, respectively.

FIGS. 6A-K illustrate different embodiments of static fiber optic cables 40.

Figure 6A:
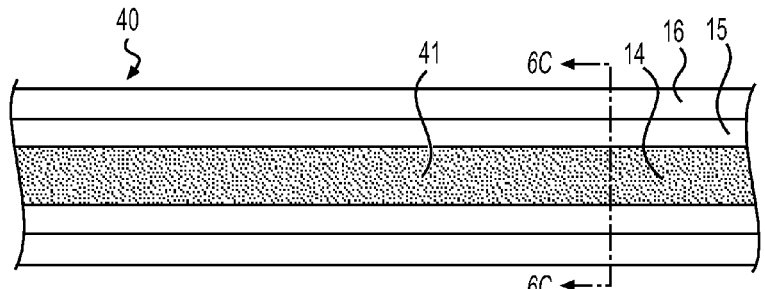
FIGS. 6A-K are illustrations, including cross-sectional views, of static fiber optic cables, according to at least one aspect of the disclosure.
Figure 6C:
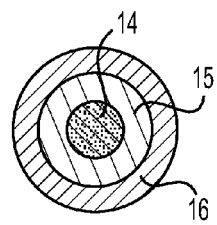
Figure 6B:
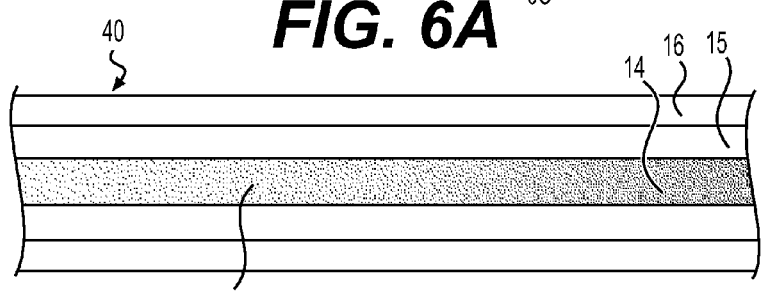
Figure 6D:
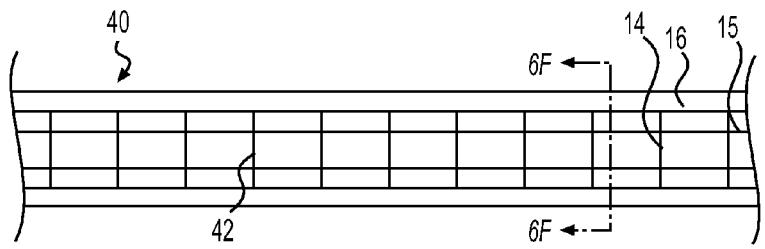
Figure 6F:
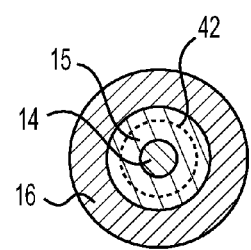
Figure 6E:
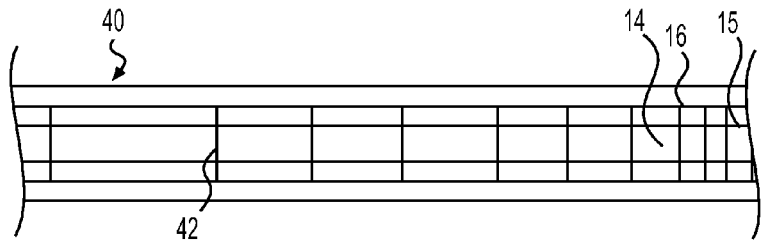

With reference to FIGS. 6D-F, embodiments of static fiber optic cable 40 may contain discontinuities 42 for causing UV radiation to scatter, causing it to radiate in an outward, radial direction, toward the luminal walls of catheter 1. In certain embodiments, such discontinuities 42 may be discrete—e.g., cuts or scoring in cladding 15 and/or core 14 of static fiber optic cable 40, for example, as depicted in FIGS. 6D-F. Such cuts may be generated by laser or mechanically. In other embodiments, non-discrete discontinuities 42 may be formed by compromising the integrity of core 14 and/or cladding 15, for example, by mechanically stressing portions of static fiber optic cable 40. Such mechanical stressing may include bending the optical fiber beyond its minimum momentary bending radius (which is typically around 100 times the cladding radius) or crushing the fiber in controlled processes.

FIG. 6D illustrates an embodiment whereby discontinuities 42 are evenly dispersed throughout core 14 of static fiber optic cable 40, and FIG. 6F illustrates a cross section of static fiber optic cable 40 in accordance with such embodiments. Because discontinuities 42 cause UV light to scatter outside of the optical fiber, the power of UV light propagated forward by the optical fiber is reduced in a non-linear fashion from the proximal end 11 to distal end 12 of static fiber optic cable 40. Because of this, an even distribution of discontinuities 42 along the length of static fiber optic cable 40 will result in higher power of radial scattering of UV light at portions closer to proximal end 11 and lower radial scattering of UV light at portions closer to distal end 12.

If a more even distribution of radially scattered UV light is desired, discontinuities 42 can be incorporated in a gradient, such that greater fraction of remaining UV light power is scattered per unit length further down the fiber (toward the distal end). For example, with reference to FIG. 6E, to maintain relatively similar radial UV power output over the length of static fiber optic cable 40, the length between each subsequent discontinuity 42 (moving in the direction toward distal end 12) should to be shorter than the length to previous discontinuity 42 by approximately the fraction of power scattered by each subsequent discontinuity.

For example, the discontinuities 42 can be distributed such that 1% of the incident power is scattered per cm of length in proximal portions of the fiber (e.g., the section of static fiber optic cable 40 intended to radially scatter UV light), 20% of the incident power is scattered per cm of length toward the distal end of the fiber, and nearly 100% of the incident power is scattered per cm of length in the distal-most portions of the fiber. Since there will be less available power in the distal portions of the fiber, the greater fractional emission will allow the fiber to radially scatter a relatively uniform amount UV light along the length of the fiber.

In certain embodiments, an appropriate distribution of discontinuities 42 may be determined in accordance with the following model where X is the discontinuity number (and X+1 is the next discontinuity 42), with the first discontinuity 42 being the proximal-most discontinuity 42. In this model, each discontinuity 42 may scatter UV light in accordance with the following equation, where $S_X$ is the power of UV light that is scattered by discontinuity X (including UV light scattered radially and backreflected); $I_X$ is the power of UV light propagated onto discontinuity X, along static fiber optic cable 40; and P is the scattering proportion (i.e., the proportion of UV power that is scattered at each discontinuity):

$$S_X = I_X * P$$

$I_0$ may be considered to be incident radiation propagated to first discontinuity 42 from light source 62. And the power of UV light propagated through each discontinuity X may be modeled in accordance with the following equation.

$$I_{X+1} = I_X - S_X$$

Under this model, in order to maintain relatively similar radial UV light scattering along the length of static fiber optic cable 40, the distance between subsequent discontinuities should be progressively shortened by a proportion equal to the scattering proportion P.

In embodiments with non-discrete discontinuities 42 (not shown), the densities of such non-discrete discontinuities 42 may be effectively increased along the fiber in the distal direction. This may be accomplished by subjecting the more distal portions of the fiber to greater mechanical stresses, as discussed below with respect to FIG. 8.

With reference to FIGS. 6A-C, embodiments of static fiber optic cable 40 may contain scattering centers 41 for reflecting UV radiation in an outward, radial direction, toward the luminal walls of catheter 1. In certain embodiments, scattering centers 41 may be particles that may comprise, for example, ZnO, $Al_2O_3$, air bubbles, or other particles that alter the local refractive index. For example, air bubbles may be incorporated into core 14 and allow the light to exceed the angle of total internal reflection, thus allowing the light to escape from the core-cladding interface. FIG. 6A illustrates an embodiment whereby scattering centers 41 are evenly dispersed throughout core 14 of static fiber optic cable 40, and FIG. 6C illustrates a cross section of static fiber optic cable 40 in accordance with such embodiments. In other embodiments (not shown), scattering centers 41 may be incorporated into cladding 15 in addition to, or instead of, core 14.

Because scattering centers 41 (similar to discontinuities 42, discussed above) cause UV light to scatter outside of the optical fiber, the power of UV light propagated by the optical fiber is reduced as in a non-linear fashion from the proximal end 11 to distal end 12 of static fiber optic cable 40. Because of this, an even distribution of scattering centers 41 along the length of static fiber optic cable 40 will result in higher radial scattering of UV light at portions closer to proximal end 11 and lower radial scattering of UV light at portions closer to distal end 12. If a more even distribution of radially scattering UV light is desired, scattering centers 41 can be incorporated in a gradient, such that a greater proportion, per unit length, of UV light power remaining in the fiber is scattered further down the fiber (toward the distal end). For example, with reference to FIG. 6B, to maintain relatively similar radial UV power output over the length of static fiber optic cable 40, the density of scattering centers 41 (moving in the direction distal end 12) should increase in a non-linear fashion. An appropriate density gradient may be determined experimentally and/or through modeling similar to that described above with respect to discontinuities 42. For example, the gradient may logarithmically increase the number of scattering centers 41 along the length of the fiber.

Figure 6G:
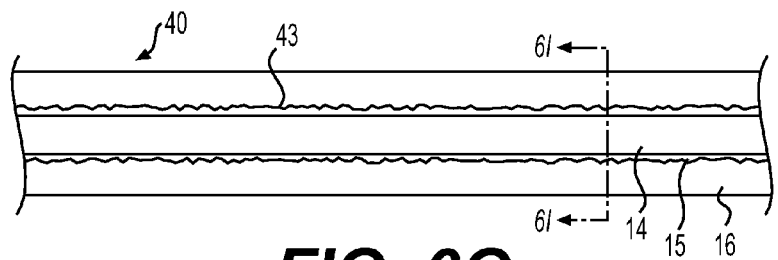
Figure 6I:
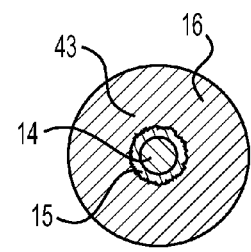
Figure 6H:
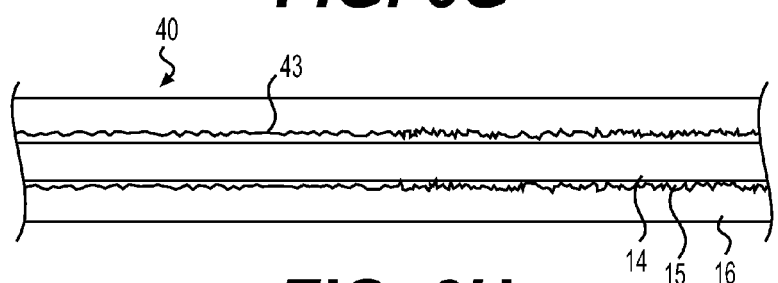

With reference to FIGS. 6G-I, in others embodiments, static fiber optical cable 40 may have roughened cladding 43 to scatter light radially, by preventing the fiber from containing all of the incident light. Cladding 15 may be roughened, for example with an abrasive or an etchant, and then enclosed in buffer 16 (or re-enclosed if buffer 16 had been previously stripped). FIG. 6G depicts static fiber optical cable 40 where the roughness of roughened cladding 43 is relatively uniform along the length of static fiber optical cable 40 intended to radially scatter UV light, and FIG. 6I illustrates a corresponding cross section.

With reference to FIG. 6H, this roughening can be applied in a gradient fashion such that the cladding at distal portions of the fiber are rougher than the cladding at proximal portions of the fiber. Similar to the discontinuity and scattering center embodiments discussed above, certain roughness gradient embodiments may result in a relatively uniform radial scattering of UV light along the portion of the fiber containing roughened cladding 43.

In certain preferred embodiments, static fiber optic cable 40 may not incorporate (or may otherwise minimize) discontinuities 42, scattering centers 41, and/or roughened cladding 43 along portions of static fiber optic cable 40 that (i) are positioned within fiber jacket 17, (ii) are proximal to any (or all or some) stopper markings 21, (iii) would necessarily be contained within catheter connector 70 during sterilization, and/or (iv) are proximal to stopper 20 (in embodiments where stopper 20 may be attached during manufacture).

Figure 6J:
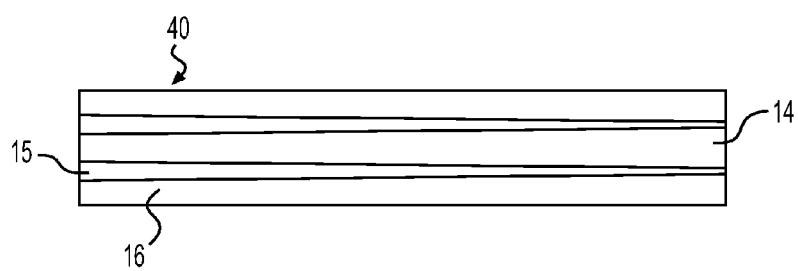

With reference to FIG. 6J, certain embodiments of static fiber optic cable 40 may include cladding 15 that is reduced in thickness along the length of the fiber (moving in the distal direction). This gradual reduction in thickness may cause UV light to escape the core and along the length of the fiber, which may scatter the UV light in a relatively uniform fashion.

Figure 6K:
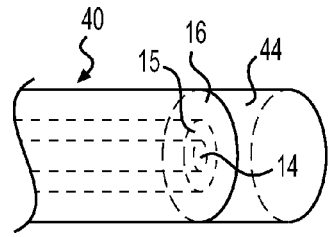

With reference to FIG. 6K, certain embodiments of static fiber optic cable 40 may comprise end cap 44 to mirror remaining forward-propagating light back through the fiber so that it may be radially scattered and/or improve backreflectance-related feedback. In certain embodiments, end cap 44 may be, for example a layer of silver or aluminum and/or a corner reflector. In other embodiments, the distal end of static fiber optic cable 40 may be terminated in an alternative fashion as to maximize the backreflectance of remaining light through the fiber.

Figure 8:
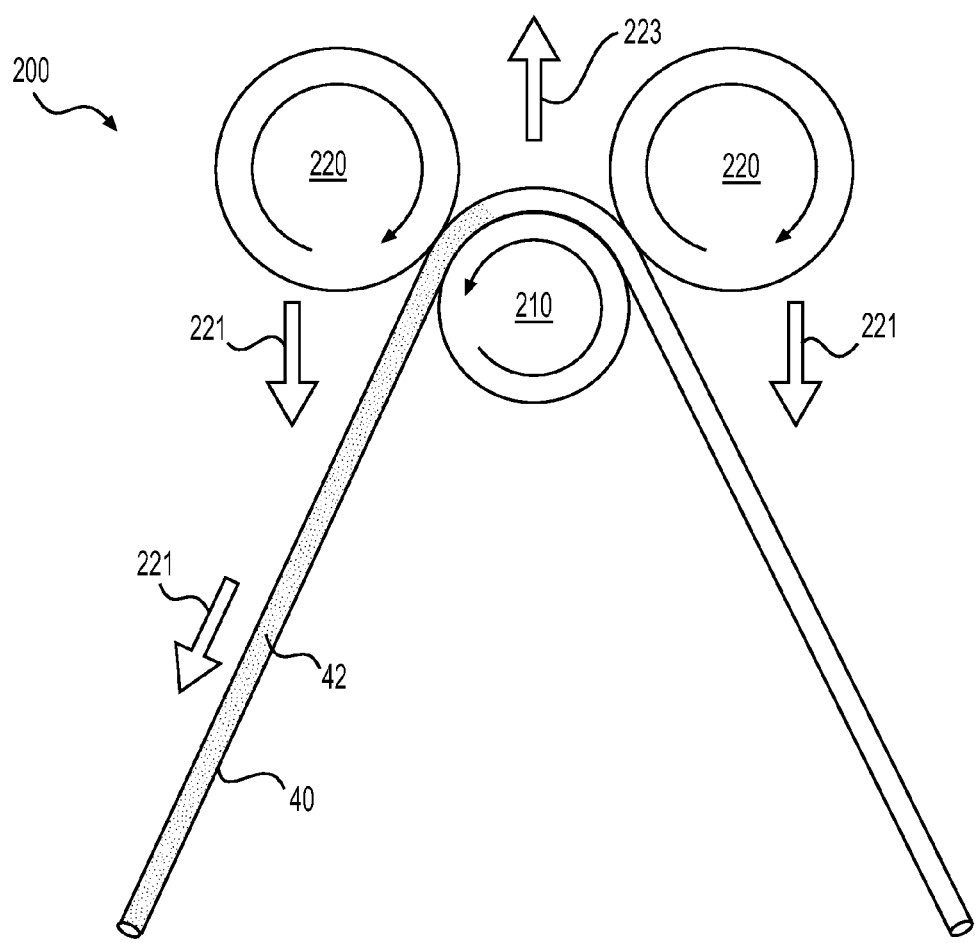
FIG. 8 is an illustration of a method of incorporating discontinuities in a fiber optic cable, according to at least one aspect of the disclosure.

FIG. 8 illustrates an exemplary apparatus for incorporating non-discrete discontinuities 42 into static fiber optic cable 40. Discontinuity manufacturing apparatus 200 may contain small roller 210, which has a radius of less that the minimum momentary bending radius of static fiber optic cable 40, and pinch rollers 220, which serve to hold static fiber optic cable 40 against small roller 210. By causing static fiber optic cable 40 to bend around small roller 210 as it is pulled in fiber direction 221, non-discrete discontinuities 42 may be induced in static fiber optic cable 40. Further, by altering the relative positions of pinch rollers 220 with respect to small roller 210, the degree of bending of static fiber optic cable 40, and therefore the density of discontinuities 42, can be controlled. Discontinuity manufacturing apparatus 200 may also incorporate discontinuities 42 in a gradient by increasing the degree of bending of static fiber optic cable 40 as it is pulled in fiber direction 221. For example, both or one of pinch rollers 220 may be moved in pinch roller relative direction 221 and/or small roller 210 may be moved in small roller relative direction 223 as fiber optic cable 40 is pulled in fiber direction 221.

In other embodiments (not shown), discontinuity manufacturing apparatus 200 may induce discontinuities 42, in a controlled crushing process. For example, static fiber optic cable 40 may be positioned between—and crushed by—pinch rollers 220 as it moves in direction 221. Discontinuities may be incorporated in a gradient by bringing pinch rollers 220 closer together (or further apart) as static fiber optic cable 40 moves in direction 221.

Fiber Optic Cable Position Feedback

Because the distal tip of fiber optic cable 10 may potentially damage internal bodily tissues, preferred embodiments of UV light-based sterilization system 100 include mechanisms or techniques to avoid extending fiber optic cable 10 beyond (or much beyond) distal catheter end 3 (and/or the distal end of a lumen of catheter 1). As noted above, stopper 20 may be such a mechanism. Other mechanisms and techniques may rely on providing feedback of the fiber optic cable 10's position to an operator (or a device operated by the operator). Further, such position feedback mechanisms and techniques may advantageously improve control of fiber optic cable 10 or provide additional medical data, regardless of whether stopper 20 is additionally used.

In certain embodiments, the distal end 12 of the fiber optic cable 10 can be coated or affixed with radiopaque material, such as tungsten, silver, gold, platinum, copper, iron, barium, tantalum, and/or alloys thereof. For example, end cap 44 or light diffusor 44 may have radiopaque properties. And in other embodiments, all or part of fiber buffer 16 may be coated with, impregnated with, or marked with a radiopaque material such as the substances recited above or a radiopaque ink. For example, one or more readable marks, discussed above with respect to dynamic fiber optic cable 30, may be radiopaque. Thus, in conjunction with a machine that produces x-rays, for example a fluoroscopy machine, an operator can track the location of fiber optic cable 10 and/or its tip. Alternatively, the catheter tip can be made to be of echogenic material, such that the tip can be detected via sonographic methods, such as with an echocardiogram.

In other embodiments, backreflectance may be used to determine fiber position and/or whether the tip has exited catheter lumen 4 and entered the bloodstream. For example, backreflectance will be altered based on whether or not the tip of fiber optic cable 10 is enclosed by catheter 1 due to the additional backreflectance of light by intraluminal walls. By comparing the backreflectance measured by detector 80 to predetermined values, controller 90 may determine whether or not the tip has reached, almost reached, and/or extended beyond distal catheter end 3.

In yet other embodiments, light source 62 may emit light of bio-safe wavelength(s) instead of (or in addition to) light in the UVC band for measuring backreflectance (and/or to indicate to an operator that light source 62 is on). Exemplary biosafe wavelengths may range from 400-1000 nm, and may be, in preferred embodiments, around 600 nm, or in the infrared band. Advantageously, as a safety measure light source 62, may emit visible light while UV source is on to inform the operator that there is a risk of UV light exposure. For example, in one embodiment, UV light source 62 comprising a laser-diode pumped solid state UV laser may effectively emit green visible light (for example, around 532 nm), which is half the frequency of UVC band light and which results from a portion of the light that is not frequency doubled within the laser. As a safety measure, it may be preferable to refrain from using UV light during fiber insertion and until sterilization begins. Thus, light source 62 may emit infrared or visible light during fiber optic cable 10 insertion.

In yet other embodiments, light source 62 may transmit coherent light along fiber optic cable 10. When the coherent light reaches the end of the fiber, mobile particles from blood may scatter light back through fiber optical cable 10 to detector 80. By measuring the Doppler shift of the light, the presence of flowing blood can be determined. The technique is not limited to coherent sources, but also can be used with low-coherence sources. Whether with coherent or low-coherent light, optical interferometry can be utilized to obtain the Doppler signal. Advantageously, embodiments of UV light-based sterilization system 100 that can support Doppler signal detection may also be able to provide a measurement of blood flow at distal catheter end 3.

Biofilm Removal

Although treatment with UVC light may effectively sterilize catheter 1 and any biofilm therein, biofilm deposits within catheter 1 may remain after sterilization. Although not in and of itself virulent, such sterilized biofilm may provide fertile ground for microbial re-colonization of catheter 1. Thus, removal of some or all biofilm before, during, or after UV-light based sterilization may advantageously aid in preventing, delaying, or reducing severity of catheter 1 re-infection. Biofilm may be removed or loosened using fluid and/or mechanical means.

In some embodiments, catheter 1 may be treated with cleaning solution before UV light treatment. With reference to FIG. 1, a cleaning solution source, such as a syringe filled with cleaning solution, can be attached to fluid port 73; catheter 1 may be filled with cleaning solution; an appropriate time to allow cleaning solution to deteriorate (and, in some embodiments sterilize) biofilm in catheter 1 may be allowed to pass; and then the cleaning solution may be removed via fluid port 73. Or, if the cleaning solution would not be harmful to the patient, it may be flushed into the patient's bloodstream rather than removed through fluid port 73. With reference to FIGS. 3 and 5, this process may occur after steps S6 and S26, respectively. Alternatively, a fluid-based biofilm cleaning process may proceed after catheter 1 is radiated with UV light.

Figure 9:
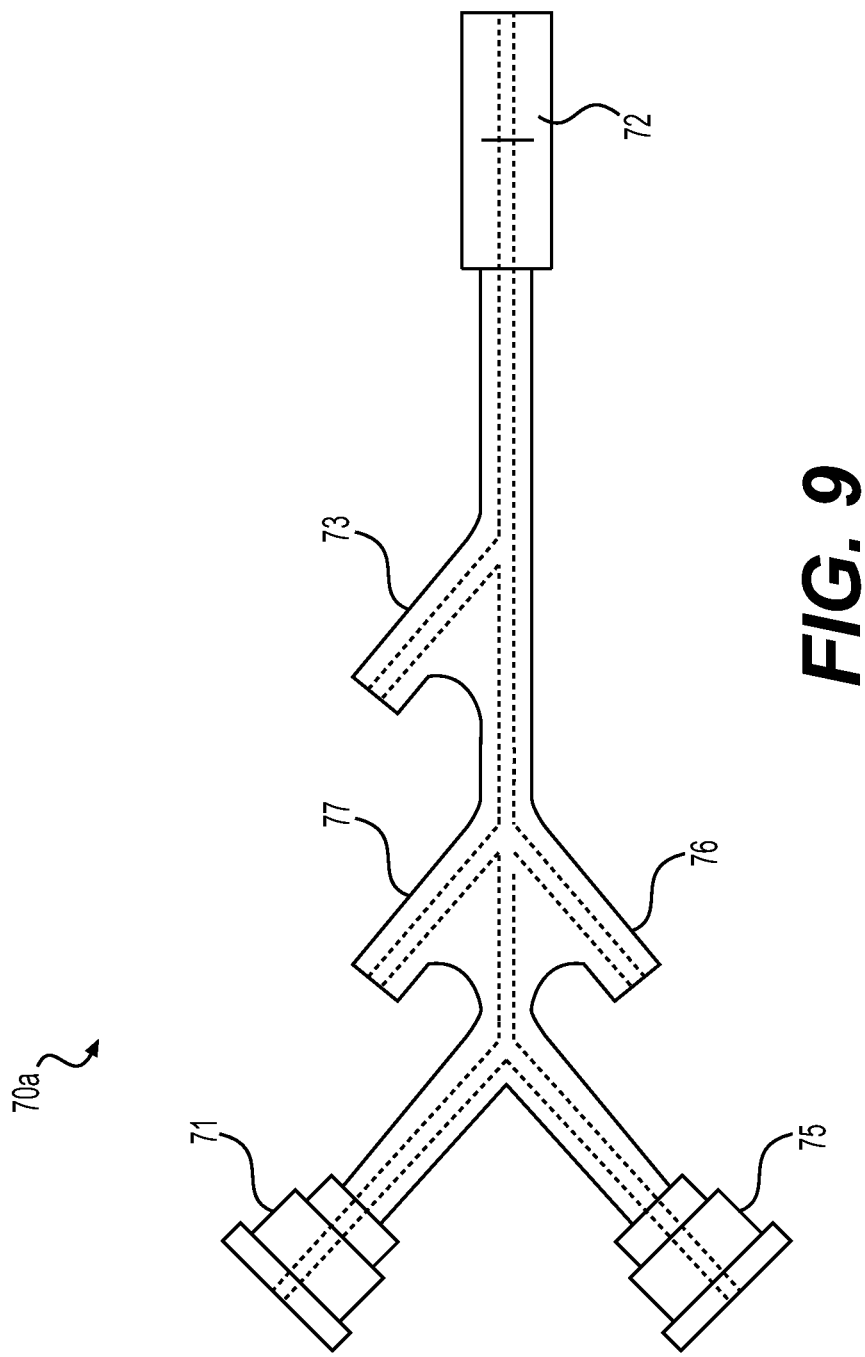
FIG. 9 is an illustration of a catheter connector with additional ports, according to at least one aspect of the disclosure.

With reference to FIG. 9, in certain embodiments, catheter connector with addition ports 70a, or an iteration thereof, may be used in UV light-based sterilization system 100. Embodiments using catheter connection with additional ports 70a may include cleaning solution port 77 to attach the cleaning solution source and/or suction port 76, to which a suction device may be attached in order to remove the cleaning solution or other fluids. In such embodiments, fluid source 74 may be attached to fluid port 73 and may contain saline. Cleaning solution port 77 and/or suction port 76 may include one-way valves.

In some embodiments, the cleaning solution may comprise certain calcium chelators (EDTA) and/or solutions with sodium bicarbonate. The cleaning solution may also comprise a combination of sodium bicarbonate, sodium metaperiodate, and/or SDS as discussed in Gawande, P. V. et al. (2008), Antibiofilm Activity of Sodium Bicarbonate, Sodium Metaperiodate and SDS Combination Against Dental Unit Waterline-Associated Bacteria and Yeast. *Journal of Applied Microbiology*, 105, 986-992.

Figure 7A:
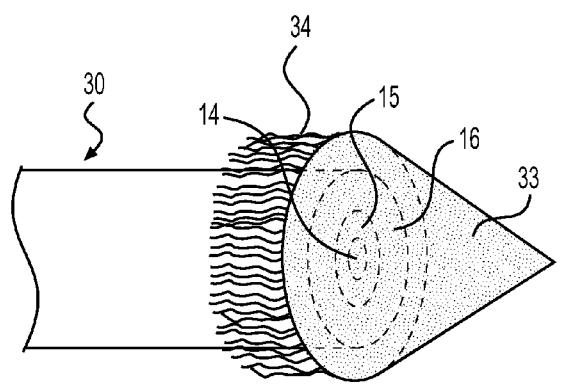
FIG. 7A is an illustration of a fiber optic cable tip for removing biofilm, according to at least one aspect of the disclosure.

In other embodiments, fiber optic cable 10 may be modified to mechanically remove biofilm as it is removed from and/or inserted into catheter 1. For example, with reference to FIG. 7A, the base of modified light diffusor 33 may be affixed onto the distal end of dynamic fiber optic cable 30. Light diffusor 33 may be cone shaped and have a base with an area that is slightly smaller than the cross-sectional area of lumen 4 and larger than the cross-section of dynamic fiber optic cable 30. Additionally, modified light diffusor 33 may incorporate bristles 34 that are attached to the exposed portion of its base. As this embodiment of dynamic fiber optic cable 30 is withdrawn from catheter 1, the base of modified light diffusor 33 and bristles 34 may scrape and remove sterilized biofilm from the intraluminal walls of catheter 1. Suction may be applied to catheter connector 70 while such an embodiment of dynamic fiber optic cable 30 is withdrawn. However, as this embodiment of dynamic fiber optic cable 30 is inserted into catheter 1, little biofilm may be pushed through the catheter and into the patient's blood stream because of the cone shape of modified light diffusor 33 and the fact that bristles 34 are effectively hidden behind the base of modified light diffusor 33. After using such a dynamic fiber optic cable 30 or the like, it may be advantageous to subsequently flush catheter 1 (with or without using suction to remove the flushing fluid) to remove biofilm debris.

Figure 7B:
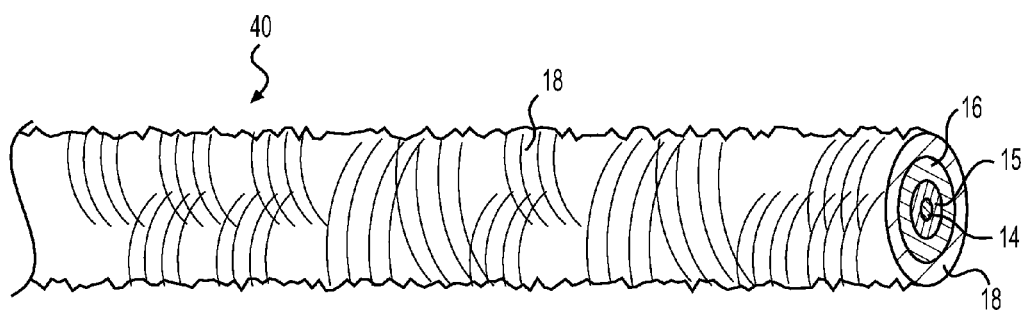
FIG. 7B is an illustration of a fiber optic cable for removing biofilm, according to at least one aspect of the disclosure.

In another embodiment, with reference to FIG. 7B, static fiber optic cable 40 may comprise additional bristled layer 18, made of a soft polymer surrounding buffer 16. Bristled layer 18 may act as an adjunct to mechanically remove or loosen any bacteria and biofilm on the inside of the catheter. In various embodiments, bristled layer 18 may comprise polyurethane, silicone, or other polymers applied by electrospinning; or Teflon fibers wrapped around buffer 16. After using such a static fiber optic cable 40 or the like, it may be advantageous to subsequently flush catheter 1 (with our without using suction to remove the flushing fluid) to remove biofilm debris.

An endoluminal brush, such as those disclosed in U.S. Published Patent Application US 2005/0171493 by Anthony C. Nicholls, may also be used to remove biofilm in certain embodiments. Because brushing is likely to result in pushing some biofilm through catheter 1 and into the patient's bloodstream, it is preferred that any intra-luminal brushing occur after UV radiation is administered, such that brushed biofilm entering the patient's bloodstream is already sterilized. For example, with reference to FIG. 1, an endoluminal brush may be introduced into catheter 1 through fiber insertion port 71 of catheter connector 70 after fiber optic cable 10 has been used to sterilize catheter 1, and subsequently been removed. Alternatively, with reference to FIG. 9, endoluminal brush may be introduced into catheter 1 through secondary instrument port 75 of catheter connector 70a. In preferred embodiments, an endoluminal brush may be fitted with stopper 20 to prevent the brush from protruding beyond (or much beyond) distal catheter end 3. Further, in some embodiments, catheter 1 may be re-flushed (with our without using suction to remove the flushing liquid) after intra-luminal brushing to remove remaining biofilm debris.

Figure 10:
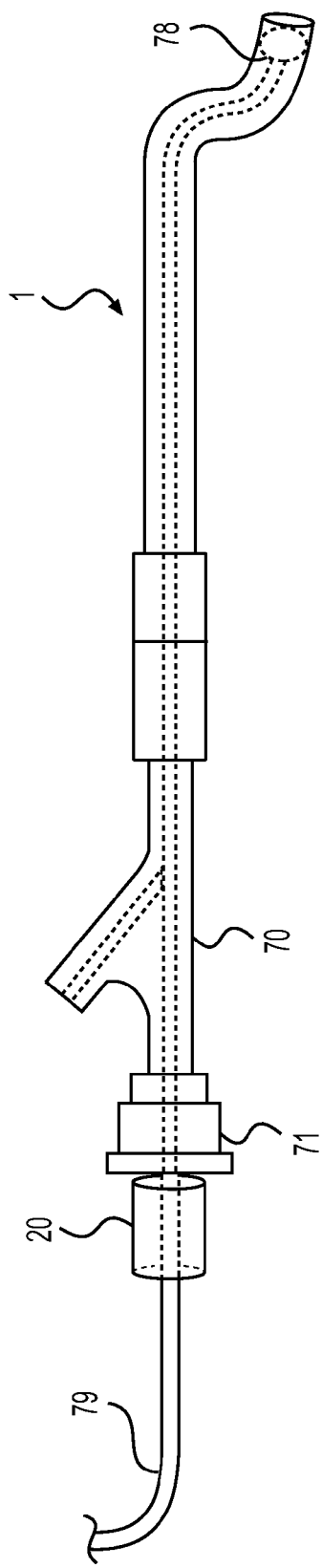
FIG. 10 is an illustration of a balloon and guidewire with a stopper, according to at least one aspect of the disclosure.

In another embodiment, with reference to FIG. 10, balloon 78 may be used as a mechanical biofilm cleaning device. For example, deflated balloon 78 and its guidewire 79 may be introduced into catheter 1 through either fiber insertion port 71 of catheter connector 70 secondary instrument port 75 of catheter connector 70a. Balloon 78 may be placed at the distal-most end of catheter 1 and inflated within lumen 4. Guidewire 79 includes preferably includes affixed stopper 20 to aid in positioning the balloon. Balloon 78 may then be withdrawn from catheter 1, scraping and removing biofilm from the intraluminal walls 1. Suction may be applied to catheter connector 70 as balloon 78 is withdrawn. Preferably, at least balloon 78's proximal side is bristled to aid in biofilm removal. Alternatively or additionally, the radial portion and/or distal side of balloon 78 may be bristled. Because little biofilm will be pushed through the catheter into the patient's bloodstream while deflated balloon 78 is inserted, using balloon 78 to remove biofilm may be accomplished before or after UV light is administered. Further, in some embodiments, catheter 1 may be re-flushed (with or without using suction to remove the flushing liquid) after balloon-based biofilm removal to remove remaining biofilm debris.

In yet another embodiment, biofilm may be removed and/or loosened via sonication, by introducing a sonication tool into the catheter via either fiber insertion port 71 of catheter connector 70 secondary instrument port 75 of catheter connector 70a. In other embodiments, the sonication tool may affix to catheter hub 5 for sonication. Frequencies between 20 and 400 kHz may be suitable for sonication, and 40 kHz may be used in certain embodiments. Preferably, sonication would occur after UV radiation is administered. Further, in some embodiments, catheter 1 may be re-flushed (with our without using suction to remove the flushing liquid) after sonication of catheter 1 to remove remaining biofilm debris.

Finally, in some embodiments, backreflectance measurements by detector 80, as discussed above, may enable the determination of biofilm levels within catheter 1. Specifically, because the reflectivity of lumen 4 of a clean catheter is different than that of a biofilm-laden lumen 4, backreflectance measurements may reveal the biofilm levels within the catheter. Thus, by comparing the backreflectance measured by detector 80 to predetermined values and/or previously taken backreflectance measurements (taken, for example, when new catheter 1 was introduced into the patient), controller 90 may determine biofilm levels and/or cleaning effectiveness. Either UV light or a biosafe wavelength may be used. The determination of biofilm levels may reveal whether removal of biofilm is necessary and/or whether attempts remove biofilm were effective.

Currently, physicians—often in response to suspected infection or thrombosis—commonly replace certain types of catheters, for example, tunneled chronic dialysis catheters, via exchange over a guide wire inserted into a lumen of a to-be-removed catheter. Although guide wire exchanges can be easier, less time consuming, and less traumatic than removing a catheter and implanting a new catheter at a different site, there is a risk that the guide wire may seed an intraluminal infection in the new catheter with microbes from the biofilm in a to-be-removed catheter. This infection seed risk can be effectively eliminated by treating the to-be-removed catheter with UV light-based sterilization system 100 before guide wire exchange occurs, thereby killing microbes and sterilizing the lumen, including any biofilm. In other embodiments, a static fiber optic cable 40 with a soft tip can, itself, serve as a guide wire after it sterilizes a lumen of a to-be-removed catheter.

Automatic Fiber Optic Cable Control System

Figure 11:
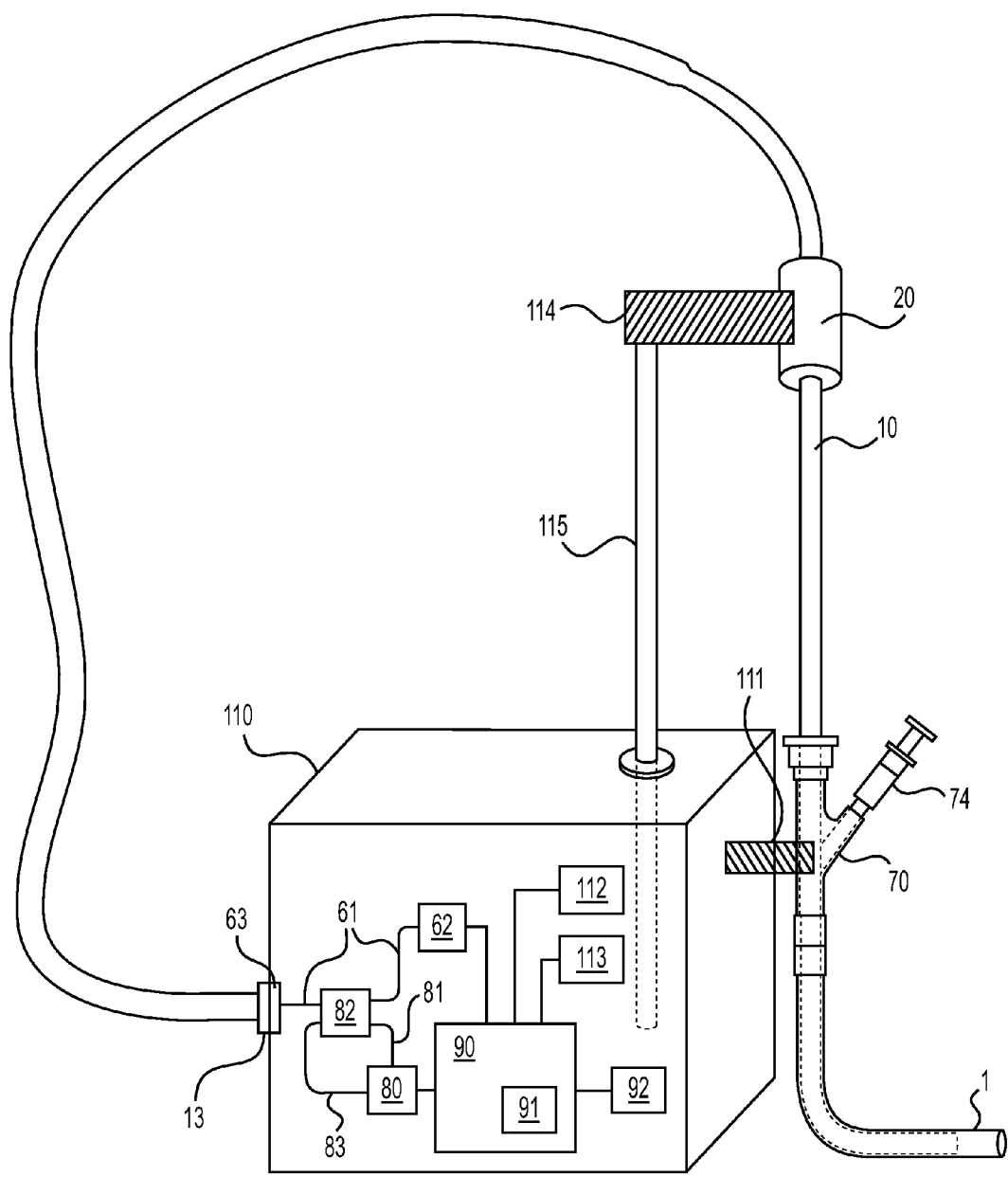
FIG. 11 is an illustration of a UV light-based sterilization system incorporating an automatic fiber optic cable control system, according to at least one aspect of the disclosure.

As depicted in FIG. 11, exemplary UV light-based sterilization system 100 may also include automatic fiber optic control system 110, which may incorporate the components and functions of UV light base 60. Automatic fiber optic control system 110 may improve dynamic UV light-based sterilization techniques by controlling the movement of fiber optic cable 10.

In addition to the components included in UV light base 60, automatic fiber optic control system 110 may include catheter connector clamp 111, which secures catheter connector 70; automatic movement mechanism 112, which controls the movement of moving post 115; cable attachment mechanism 114, which may be attached to moving post 115; and position sensor 113, which may sense the position of moving post 115 such that the position of fiber optic cable 10 may be determined. Automatic movement mechanism 112 may be, for example, an electric motor. Cable attachment mechanism 115 is configured to attach to a portion of fiber optic cable 10 at, in some embodiments, stopper 20. Cable attachment mechanism 114 may be magnetic and engage with a magnetic stopper 20; in other embodiments, cable attachment mechanism 114 may be a clamp, or may contain a mechanism to securely engage with stopper 20 or another portion of fiber optic cable 10.

In alternative embodiments (not shown), automatic fiber optic control system 110 may include a set of rollers to control the movement of fiber optic cable 10 in lieu of moving post 115 and cable attachment mechanism 115. In such embodiments, automatic movement mechanism 112 may power the rollers and position sensor 113 may track roller movement and/or position such that the position of fiber optic cable 10 may be determined.

Figure 12:
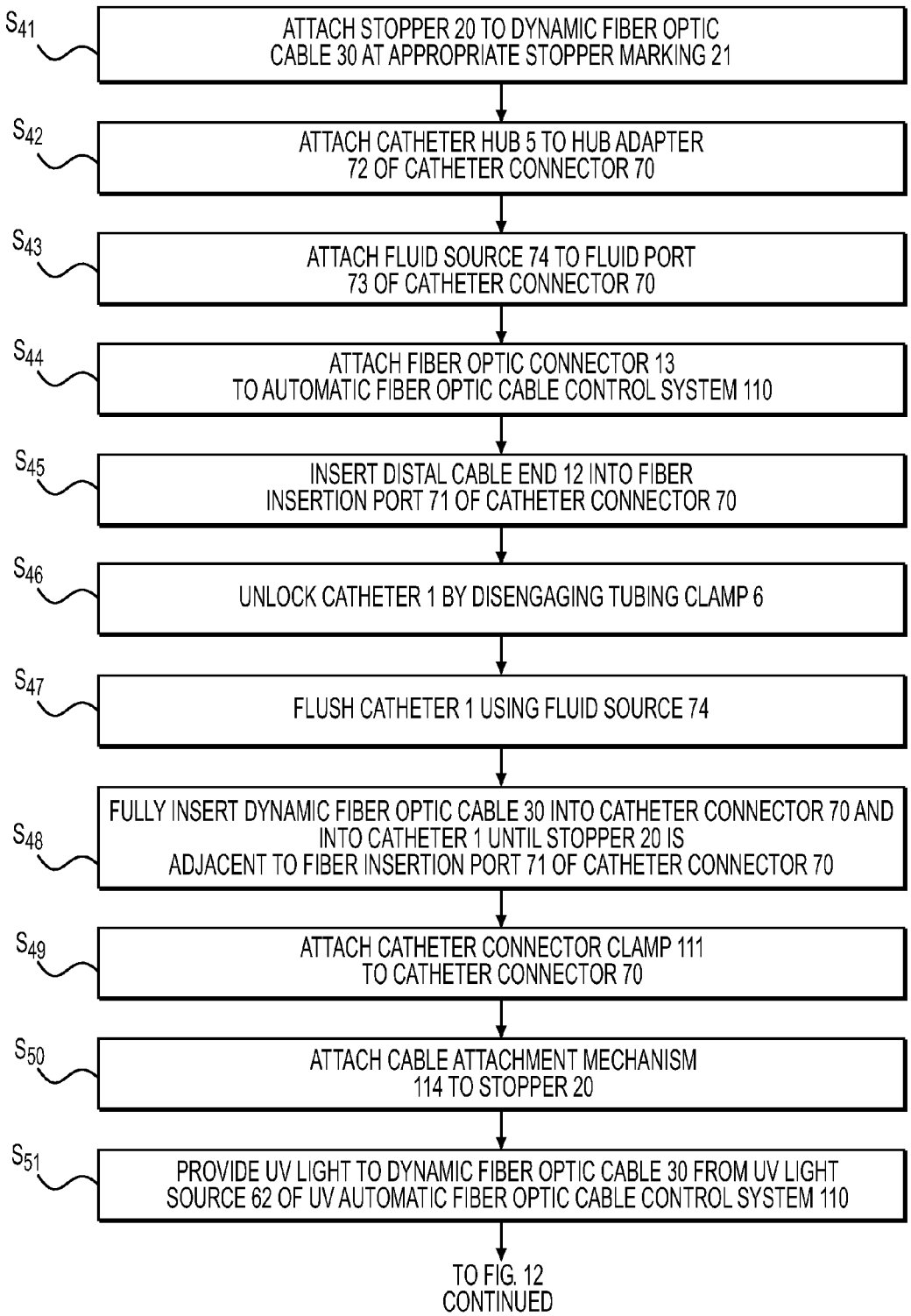
FIG. 12 is a flow chart illustrating a method of dynamic UV light-based sterilization using an automatic fiber optic cable control system, according to at least one aspect of the disclosure.
Figure 12:
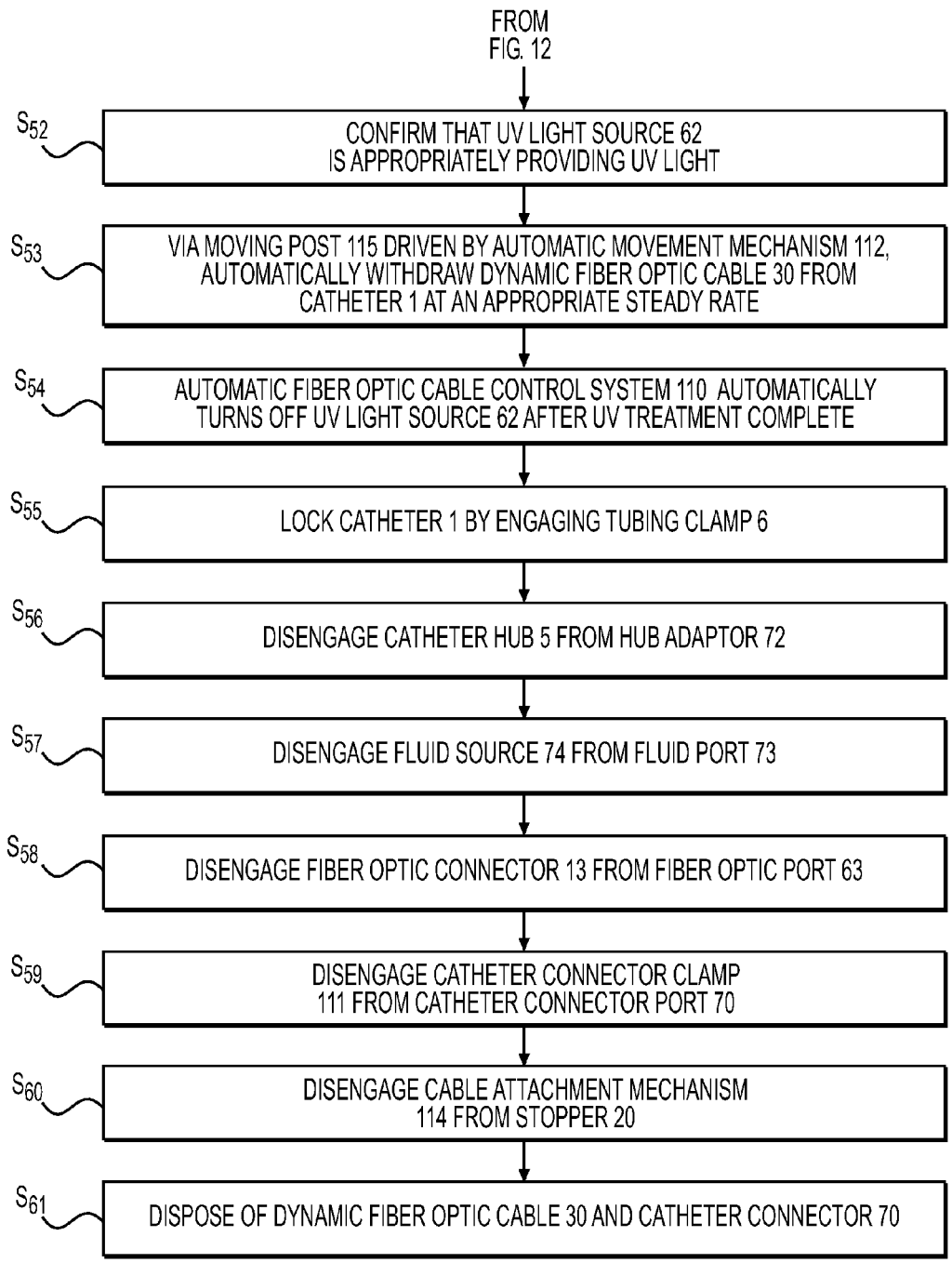

FIG. 12 is a flow chart illustrating an exemplary method of dynamic UV light-based sterilization using automatic fiber optic control system 110.

As in step S41 (parallel to step S1), the operator may attach stopper 20 to dynamic fiber optic cable 30 at appropriate stopper marking 21.

As in step S42 (parallel to step S2), the operator may attach catheter hub 5 to hub adapter 72 of catheter connector 70.

As in step S43, (parallel to step S3), the operator may attach fluid source 74 to fluid port 73 of catheter connector 70. Some embodiments of automatic fiber optic cable control system 110 (not shown) may include additional components to automatically flush catheter 1 at the appropriate time. In such embodiments, the operator may attach fluid port 73 to a fluid connection of automatic fiber optic cable control system 110.

As in step S44 (parallel to step S4), the operator may attach fiber optic connector 13 to fiber optic port 63 of automatic fiber optic cable control system 110.

As in step 45 (parallel to step S5), the operator may insert distal cable end 12 into fiber insertion port 71 of catheter connector 70. It should be noted that catheter sterilization may proceed effectively even if the order of steps S41 through S45 is altered. It should also be noted that steps S44 and S45 can take place after steps S46 and/or S74 in alternative embodiments.

As in step S46 (parallel to step S6), the operator may then unlock catheter 1 by disengaging tubing clamp 6.

As in step S47 (parallel to step S7), the operator may then flush catheter 1 with a fluid, such as saline solution, from fluid source 74. As discussed above with respect to step S43, automatic fiber optic cable control system 110 may perform this step in some embodiments. Further, some embodiments may provide for fluid withdrawal from the catheter prior to flushing, as discussed above with respect to step S7.

As in step S48, (parallel to step S8), the operator may then push dynamic fiber optic cable 30 through catheter connector 70 and into catheter 1 until stopper 20 is adjacent to fiber insertion port 71 of catheter connector 70.

As in step S49, the operator may attach catheter connector clamp 111 to catheter connector 70. It should be noted that catheter sterilization may proceed effectively if this step occurs at any time prior to step S51.

As in step S50, the operator may attach cable attachment mechanism 114 to stopper 20. When this attachment occurs, moving post 115 may be fully retracted such that cable attachment mechanism 114 is adjacent or close to the upper surface of automatic fiber optic control system 110. As noted above, this step may be omitted in embodiments where movement of dynamic fiber optic cable 30 is controlled by rollers. Similarly, in other embodiments, the operator may attach cable attachment mechanism 114 directly to dynamic fiber optic cable 30, preferably on fiber optic cable jacket 17. It should be noted that catheter sterilization may proceed effectively if this step occurs at any time prior to step S51.

As in step S51 (parallel to step S9), the operator may then direct automatic fiber optic control system 110 to provide UV light to dynamic fiber optic cable 40 from UV light source 62.

As in step S52 (parallel to step S10), the operator and/or system 110 may then confirm that UV light source 62 is appropriately providing UV light. It may be noted that steps S41-48 and S51-52 correspond directly to steps S1-10, respectively.

As in step S53 (parallel to step S11), the operator may direct automatic fiber optic control system 110 to automatically withdraw dynamic fiber optic cable 30 from catheter 1 at an appropriate steady rate by extending moving post 115 driven by automatic movement mechanism 112. Based on data from position sensor 113, automatic movement mechanism 112 automatically stops driving moving post 115 when the light-radiating tip 31 of dynamic fiber optic cable 30 enters catheter connector 70. The appropriate steady rate may be determined as discussed above with respect to step S11.

As in step S54 (parallel to step S12), automatic fiber optic control system 110 then automatically turns off UV light source 62.

As in step S55 (parallel to step S13), the operator may then lock catheter 1 by engaging tubing clamp 6.

As in step S56 (parallel to step S14), the operator may then disengage catheter hub 5 from hub adaptor 72.

As in step S57 (parallel to step S15), the operator may then disengage fluid source 74 (or, when appropriate, the fluid connection of automatic fiber optic cable control system 110) from fluid port 73.

As in step S58, (parallel to step S16), the operator may then disengage fiber optic connector 13 from fiber optic port 63.

As in step S59, the operator may then disengage catheter connector clamp 111 from catheter connector 70.

As in step S60, the operator may then disengage cable attachment mechanism 114 from stopper 20. It should be noted that catheter sterilization may proceed effectively even if the order of steps S56 through S60 are altered.

As in step S61 (parallel to step S17), the operator may then dispose of dynamic fiber optic cable 30 and catheter connector 70. It may be noted that sterilization steps S55-58 and S61 correspond directly to dynamic sterilization steps S13-17, respectively.

Embodiments of biofilm removal techniques discussed herein may also be incorporated into the above-described automatic sterilization method. For example, optional biofilm removal steps discussed above, such as using a cleaning solution, sonication tool, brush, and/or balloon, may be performed manually by the operator. However, in other embodiments, additional components may be incorporated into automatic fiber optic control system 110 to, e.g., automatically provide and remove cleaning solution, use an endoluminal brush, use balloon 78, and/or use a sonication tool at appropriate times.

Cartridge-Based Fiber Optic Cable Control System

Figure 13:
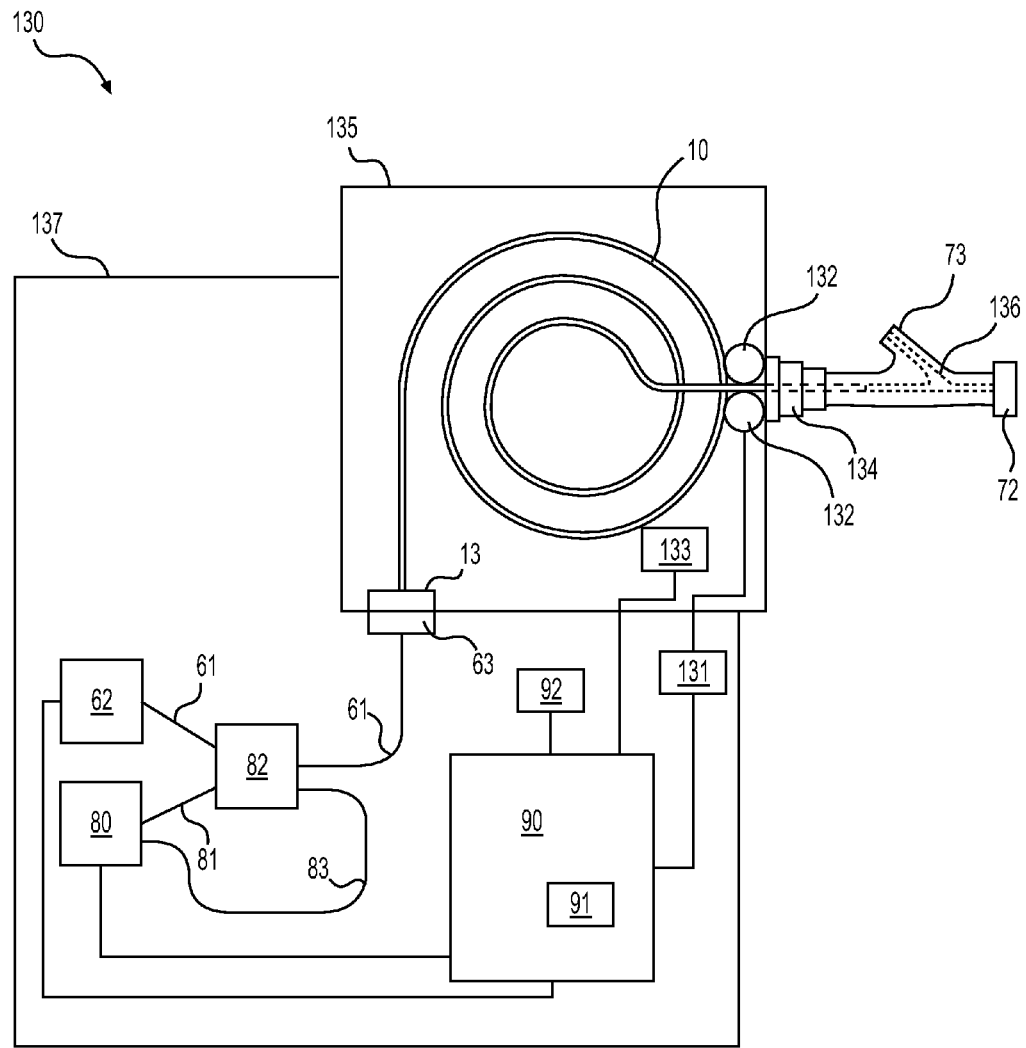
FIG. 13 is an illustration of a cartridge-based fiber optic cable control system, according to at least one aspect of the disclosure.

As depicted in FIG. 13, exemplary UV light-based sterilization system 100 may also be cartridge-based fiber optic cable control system 130, comprising cartridge control base unit 137 and disposable cartridge 135, which may maintain a sterile separation from base unit 137. Cartridge-based fiber optic cable control system 130 may support dynamic and/or static UV light-based sterilization techniques. In certain preferred embodiments, different models of cartridges 35—each corresponding to particular catheter lengths, models, and/or manufacturers—may work with the same cartridge control system base unit 137. Similarly, cartridge 135 models containing dynamic fiber optical cable 30 and/or cartridge 135 models containing static fiber optical cable 40 may both work with the same cartridge control system base unit 137.

Each disposable cartridge 135 may comprise fiber optic cable 10, fiber optic connector 13, cable rollers 132, cable position sensor 133, and catheter-cartridge connector 136. Catheter-cartridge connector 136 may be permanently attached to the housing of cartridge 135 at one-way valve 134, but may otherwise function as catheter connector 70. Cable rollers 132 may be powered by motor 131 within cartridge control system base unit 137, and may serve to push fiber optic cable 10 through catheter-cartridge connector 136 and into catheter 1 (not shown), as well as withdraw fiber optic cable 10 back into cartridge 135. Other embodiments of cartridge 135 may not include catheter-cartridge connector 136, but instead be configured to mechanically attach to catheter connector 70 or the like.

When cartridge 135 is engaged with base unit 137, fiber optic connector 13 of cartridge connects with fiber optic port 63 of base unit 137 such that light from light source 62 may propagate to fiber optic cable 10 and backreflectance may be received by detector 80. Additionally, engagement of cartridge 135 with base unit 137 may couple cable position sensor 133 with processor 90 and mechanically couple motor 131 with cable rollers 132.

In certain embodiments, cable position sensor 133 may track the position of fiber optic cable 10 indirectly, for example, by monitoring the position of one or more cable rollers 132, for example, using one or more optical encoders. Alternatively or additionally, cable position sensor 133 (in conjunction with processor 90) may track the position of fiber optic cable 10 directly, for example, by detecting and counting optically-readable marks (e.g., ink-based or laser-scored), electrically-readable marks (e.g., metallic rings, which advantageously would be radiopaque), and/or magnetic marks on the outermost surface of fiber optic cable 10. In certain embodiments, cable position sensor 133 may be positioned within base unit 137 rather than cartridge 135, and may, for example, indirectly determine fiber optic cable 10 position by tracking output of motor 131 and/or directly, for example by counting marks on fiber optic cable 10 through an appropriately positioned transparent window in cartridge 135. Cartridge-based fiber optic cable control system 130 may also provide feedback to the operator about the position of fiber optic cable 10 via user interface 92.

In certain embodiments, fiber optic cable 10 may be stored coiled within cartridge 135, preferably coiled using the over/under cable coiling technique (commonly used in the film and audio production industries), wherein each successive coil is twisted then untwisted, respectively. The over/under technique may allow fiber optic cable 10 to lie flat (and unstressed) when stored in cartridge 135 and may further prevent kinking or damage to fiber optic cable 10 as cable rollers 132 move cable 10 into catheter 1. With this technique, a fiber optic cable 10 might not be re-coiled in the over/under fashion after it is used. However, because the cartridges should not be reused, this may not be a problem.

In another embodiment (not shown), fiber optic cable 10 may be loosely wound around a cone, such that the tip of the cone points toward rollers 132. In this manner, fiber optic cable 10 may slip off of the cone as cable rollers 132 turn. Fiber optic cable 10 may, in some embodiments, be wrapped around the cone using the over/under technique. Another form that permits cable 10 to both be wrapped around it and smoothly slip off it, such as, for example, a cylinder may be used instead of a cone.

In yet other embodiments (not shown), fiber optic cable 10 may be stored on a spool. Use of standard spooling techniques may be unsuitable because, as a spool turns to release cable 10 into catheter 1, the proximal end of cable 10 would be wound up on the spool. To that end, in order to allow fiber optic connector 13 to remain connected to fiber optic port 63, the spool may function as a common garden hose reel. To avoid excessively twisting fiber optic cable, a fiber optic rotary joint that freely allows twisting without undermining light propagation should be included near the proximal end of cable 10 within cartridge 135.

Figure 14:
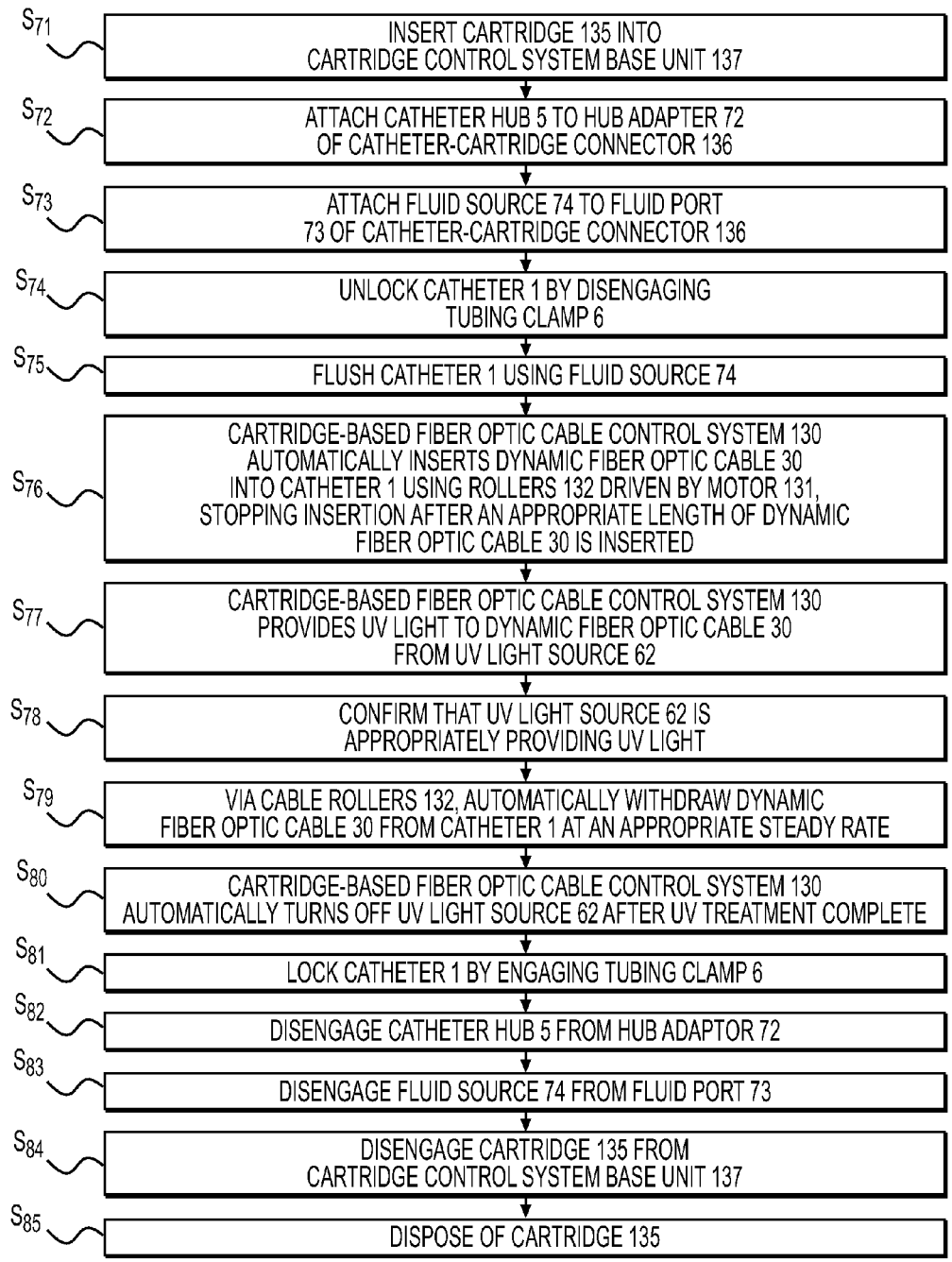
FIG. 14 is a flow chart illustrating a method of dynamic UV light-based sterilization using a cartridge-based fiber optic cable control system, according to at least one aspect of the disclosure.

FIG. 14 is a flow chart illustrating an exemplary method of dynamic UV light-based sterilization using cartridge-based fiber optic control system 130.

As in step S71, the operator may insert fiber optic cable cartridge 135 into cartridge control system base unit 137. Once engaged with cartridge 135, controller 90 of cartridge control system base unit 137 may download data from cartridge 135, including, for example, whether cartridge 135 contains a dynamic fiber optic cable 30 or a static fiber optic cable 40 (and/or multiple cables 10); fiber properties such as diameter, core size, numerical aperture, manufacturer; instructions for use; FDA labeling information; manufacturer contact information; what catheter models, lengths, and/or manufacturers cartridge 135 is intended to be used with; data relating those particular catheter models, lengths, and/or manufacturers, including, for example, recommended UV doses, catheter dimensions, appropriate steady rates, and appropriate amounts of time to wait during sterilization; a unique ID, for example, a serial number; an expiration date; whether cartridge 135 was previously used; data relating to backreflectance values, which may also be specific to particular catheter models; and/or data relating to the manufacture of cartridge 135, including for example, batch numbers, time of manufacture, and place of manufacture. This data may be stored by conventional electronic data storage means, such as flash memory or read only memory, and/or may be provided via RFID or even one or more bar codes on the exterior of cartridge 135.

As in step S72 (parallel to step S2 and S42), the operator may attach catheter hub 5 to hub adapter 72 of catheter-cartridge connector 136.

As in step S73, (parallel to steps S3 and S43), the operator may attach fluid source 74 to fluid port 73 of catheter-cartridge connector 136. Some embodiments of cartridge-based fiber optic cable control system 130 (not shown) may include additional components to automatically flush catheter 1 at the appropriate time. In such embodiments, the operator may attach fluid port 73 to a fluid connection of cartridge-based fiber optic cable control system 130. Such fluid connection may, in some embodiments, be contained within cartridge 135 such that it can later be disposed of easily along with cartridge 135

As in step S74 (parallel to steps S6 and S46), the operator may then unlock catheter 1 by disengaging tubing clamp 6.

As in step S75 (parallel to steps S7 and S47), the operator may then flush catheter 1 with a fluid, such as saline solution, from fluid source 74. As discussed above with respect to step S43, cartridge-based fiber optic cable control system 130 may perform this step in some embodiments. Further, some embodiments may provide for fluid withdrawal from the catheter prior to flushing, as discussed above with respect to step S7.

As in step S76, when so instructed by the operator, cartridge-based fiber optic cable control system 130 automatically inserts dynamic fiber optic cable 30 into catheter 1 using rollers 132 driven by motor 131, stopping insertion after an appropriate length of dynamic fiber optic cable 30 is inserted. The appropriate length may be input by the operator through user interface 92; read as data from cartridge 135; calculated by controller 90 based on data read from cartridge 135 (see, e.g., step S71); determined using backreflectance data or other feedback (e.g., from balloon 78, as discussed below), and/or some combination thereof.

As in step S77 (parallel to step S9 and S51), the operator may then direct cartridge-based fiber optic cable control system 130 to provide UV light to dynamic fiber optic cable 40 from UV light source 62.

As in step S78 (parallel to step S10 and S52), cartridge-based fiber optic cable control system 130 may then confirm that UV light source 62 is appropriately providing UV light.

As in step S79 (parallel to steps S11 and S53), cartridge-based fiber optic cable control system 130 may then automatically withdraw dynamic fiber optic cable 30 from catheter 1 at an appropriate steady rate using cable rollers 132. In some embodiments, controller 90 may calculate the appropriate steady rate based on available (or desired) power, a requested UV radiation dose input, and/or catheter specific data (e.g., lumen diameter). These factors may be input by the operator into user interface 92, suggested for the particular catheter 1 model being sterilized, and/or included in the data downloaded from cartridge 135. In other embodiments, the appropriate steady rate, itself may be input by the operator into user interface 92, suggested for the particular catheter 1 model being sterilized, and/or included in the data downloaded from cartridge 135.

As in step S80 (parallel to steps S12 and S54), cartridge-based fiber optic cable control system 130 then automatically turns off UV light source 62. Upon completion of UV treatment, cartridge-based fiber optic cable control system 130 may alter data on cartridge 135 to indicate that the cartridge as been used and/or is no longer sterile. In some embodiments, cable rollers may continue rolling after dynamic fiber optic cable 30 has fully withdrawn into cartridge 135 such that cartridge 135 is rendered unusable.

As in step S81 (parallel to steps S13 and S55), the operator may then lock catheter 1 by engaging tubing clamp 6.

As in step S82 (parallel to steps S14 and S56), the operator may then disengage catheter hub 5 from hub adaptor 72.

As in step S83 (parallel to steps S15 and S57), the operator may then disengage fluid source 74 (or, when appropriate, fluid connection of cartridge-based fiber optic cable control system 130) from fluid port 73.

As in step S84, the operator may then disengage cartridge 135 from cartridge control system base unit 137. It should be noted that catheter sterilization may proceed effectively even if the order of steps S82 through S84 are altered.

As in step S85, the operator may then dispose of cable cartridge 135, maintaining optimum sterility of cartridge control system base unit 137.

Figure 15:
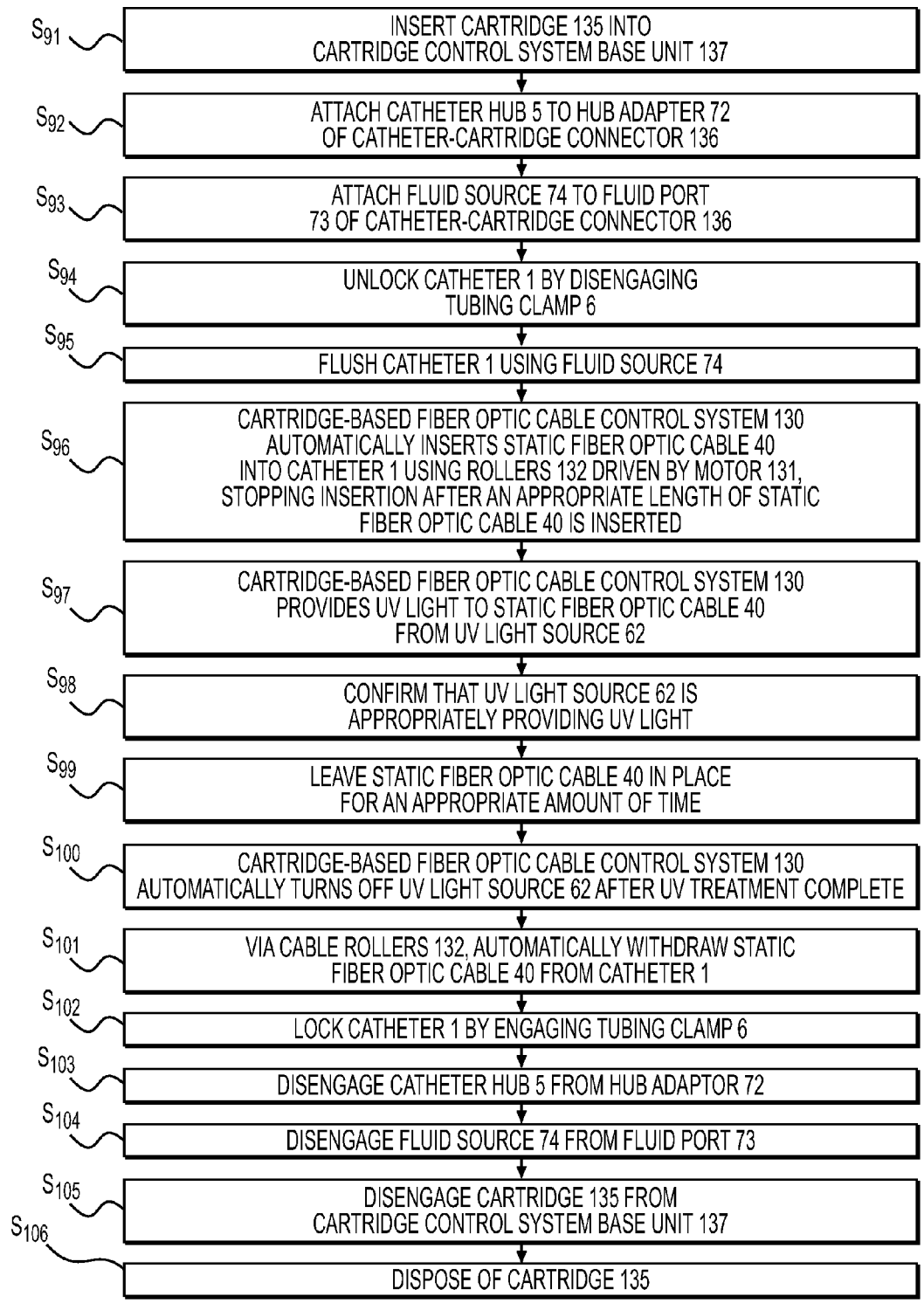
FIG. 15 is a flow chart illustrating a method of static UV light-based sterilization using a cartridge-based fiber optic cable control system, according to at least one aspect of the disclosure.

FIG. 15 is a flow chart illustrating an exemplary method of static UV light-based sterilization using cartridge-based fiber optic control system 130.

Steps S91-S98 of FIG. 15 are identical to steps S71-S78 of FIG. 14, respectively, except that cartridge 135 contains static fiber optic cable 40 instead of dynamic fiber optic cable 30.

As in step S99 (parallel to step S31), cartridge-based fiber optic cable control system 130 may then automatically leave static fiber optic cable 40 in place for an appropriate amount of time. In some embodiments, controller 90 may determine the appropriate amount of time in manners similar to those discussed with respect to step S79, above.

As in step S100 (parallel to step S80), cartridge-based fiber optic cable control system 130 then automatically turns off UV light source 62.

As in step S101, cartridge-based fiber optic cable control system 130 may automatically withdraw static fiber optic cable 40 from catheter 1 and into cartridge 135. Cartridge-based fiber optic cable control system 130 may alter data on cartridge 135 to indicate that the cartridge as been used and/or is no longer sterile. In some embodiments, cable rollers may continue rolling after static fiber optic cable 40 has fully withdrawn into cartridge 135 such that the cartridge is rendered unusable.

Steps S102-S106 of FIG. 15 are identical to steps S81-S85 of FIG. 14, respectively.

Embodiments of biofilm removal techniques discussed herein may also be incorporated into the above-described cartridge-based automatic sterilization techniques. For example, optional biofilm removal steps discussed above, such as using a cleaning solution or brushing catheter 1, may be performed manually by the operator. However, in other embodiments, additional components may be incorporated into cartridge-based fiber optic control system 130 to, e.g., automatically provide and remove (e.g., via suction) cleaning solution, use an endoluminal brush, use balloon 78, and/or use a sonication tool at appropriate times.

In some embodiments of cartridge-based fiber optic control system 130, balloon 78 with guidewire 79 may be used to determine catheter 1 length. Cartridge-based fiber optic control system 130 may contain components to position balloon 78 into catheter 1, inflate and deflate balloon 78, and measure the pressure in balloon 78. And balloon 78 and guidewire 79 may, in some embodiments, be included in cartridge 135 to maintain sterility.

In some embodiments, system 130 may use guidewire 79 to move balloon 78 through lumen 4 of catheter 1 toward distal catheter end 3, attempting to inflate balloon 78 at discrete intervals (e.g., every centimeter or 0.5 centimeter). Only after balloon 78 exits catheter 1, system 130 is able to successfully inflate balloon 78 (or otherwise detect a decrease in pressure of balloon 78). Thereby, controller 90 may determine the position of distal end 3 of catheter 1. Once the end of catheter 1 is detected, an inflated balloon 78 may be retracted back into catheter 1. Biofilm may be removed from lumen 4 as balloon 78 (which may be bristled, as discussed above) is withdrawn back though catheter 1, and balloon 78 may be further inflated to increase contact with the inner luminal walls before it is withdrawn.

In another embodiment, cartridge-based fiber optic control system 130 may partially inflate balloon 78 after positioning it in catheter 1; then the pressure in balloon 78 may be monitored as guide wire 79 is used to push balloon 78 toward the distal end 3 of catheter 1. As balloon 1 reaches the end of catheter 1 and begins to exit into the patient's bloodstream, the internal pressure of balloon 78 will drop, and controller 90 may note the current length of the guide wire 79 as the length of the catheter 1. Once the end of catheter 1 is detected, balloon 78 may then be retracted back into catheter 1. Biofilm may be removed from lumen 4 as balloon 78 (which may be bristled, as discussed above), is withdrawn back though catheter 1, particularly in embodiments where balloon 78 is further inflated to increase contact with the inner luminal walls before being withdrawn.

In addition, balloon 78 can be used to detect blockages within catheter 1. For example, the pressure within balloon 78 will increase if guidewire 79 presses balloon 78 against a blockage. To address a blockage, balloon 78 may be further inflated, thereby displacing debris within the blocked portion of lumen 4 to improve fluid flow.

Sterilization of Multi-Lumen Catheters

Many commonly used catheters contain multiple lumens. The catheter sterilization techniques and systems discussed herein in the context of single lumen catheters are applicable to, and may be adapted to, the sterilization of multi-lumen catheters.

Multi-lumen catheter may be sterilized in a sequential manner. That is, each lumen of the multi-lumen catheter may be sterilized via the disclosed embodiments in succession. Although it may be generally preferable to dispose of catheter sterilization materials (e.g., fiber optic cable 10 and catheter connector 70) after a single use, it may be medically reasonable and more economical to use the same sterilization materials to sterilize each lumen of a patient's multi-lumen catheter in quick succession. The likelihood of causing infection from such reuse can be relatively small. However, because some multi-lumen catheters have lumens of different lengths, when the same sterilization materials are used to sterilize multiple lumens sequentially, care should be taken to ensure that stopper 20 is appropriately re-placed (or fiber optic cable 10 position is otherwise accounted for) for each sterilization sequence.

A multi-lumen catheter can also be sterilized in a concurrent manner. That is, a separate fiber optic cable 10 and a separate catheter connector 70 may be provided for each lumen to be sterilized. In some embodiments, the plurality of fiber optic cables 10 may collectively be powered by a single light source 62 by means of a fiber splitter. If this technique is used, the power of UV radiation for each of the plurality of fiber optic cables 10 may be reduced. It may also complicate backreflectance measurement, which may require an additional fiber splitter 82 for each fiber optic cable 10. In other embodiments, there may be a separate provided light source 62 for each fiber optic cable 10 to be sterilized. This, however, may increase the cost and weight of UV light base unit 60.

As noted above, different lumens within a catheter can have different lengths. Mismatching the fibers and lumens can detrimentally result in protrusion of a fiber outside of the catheter and/or incomplete or ineffective catheter sterilization. When multiple lumens of different lengths are being sterilized, it may be advantageous to provide catheter connectors 70, elements thereof, stoppers 20, and/or cables 10 containing colors that may match corresponding catheter hubs 5 to avoid confusion or mistake. For example, with reference to FIG. 18, CVCs such as chronic dialysis catheters, typically have two lumens—an arterial lumen with a red catheter hub 5B and a venous lumen with a blue catheter hub 5A. Other multi-lumen catheters may have three or more lumens.

The coloring of system 100 components can provide assurance that the correct components are used to treat each respective catheter lumen. Fiber optic cable 10B for sterilizing the arterial lumen may be affixed with a red stopper 20, and/or a red catheter connector (or component thereof, e.g., hub adapter 72) may be provided to engage with arterial catheter hub 5B, which is colored red by convention. Likewise fiber optic cable 10A for sterilizing the venous lumen may be affixed with a blue stopper 20, and a blue catheter connector (or component thereof) may be provided to engage with venous catheter hub 5A, which is colored blue by convention. Alternatively or additionally, cables 10A and 10B can indicate their appropriate respective lumens through colored fiber optic connectors 13; colored stopper markings 21; colored readable marks; other coloration on fiber buffer 16 or jacket 17; and/or through the attachment of colored flags, including stickers or the like.

Some concurrent sterilizations techniques may utilize an embodiment of stopper 20 that may be simultaneously secured to multiple fiber optic cables 20 and/or a compound catheter connector, with multiple fiber insertion ports 71 and multiple hub adapters 72. Such a compound catheter connector may, in some embodiments have a single fluid port 73, or it may have a separate fluid port for each fiber insertion port.

For concurrent multi-lumen sterilization using dynamic sterilization techniques, it may be advantageous, where possible, to withdraw the multiple dynamic fiber optic cables 30 at the same appropriate steady rate. For example, this may be achieved by automatic fiber optic cable control system 110 by utilizing a cable attachment mechanisms 114 that may simultaneous affix multiple stoppers 20 (or other portions of dynamic fiber optic cables 30) and a catheter connector clamp 111 that may simultaneous affix multiple catheter connectors 70.

Cartridge-based fiber optic cable control system 130 may also be adapted to concurrently sterilize a multi-lumen catheter. For example, certain embodiments of cartridge control system base unit 137 may be adapted to engage and operate multiple cartridges 135 simultaneously. Alternatively or additionally, a single cartridge 135 may contain multiple fiber optic cables 10 and multiple-catheter cartridge connectors. For example, particular models of cartridges 35 may correspond with particular multi-lumen catheter models. Preferably, such cartridges 35 may contain downloadable data pertaining to each lumen and/or may have colored hub adapters 72 and/or catheter-cartridge connectors 136 that correspond with colored hubs 5 of each lumen.

Sterilization Kits

Figure 19:
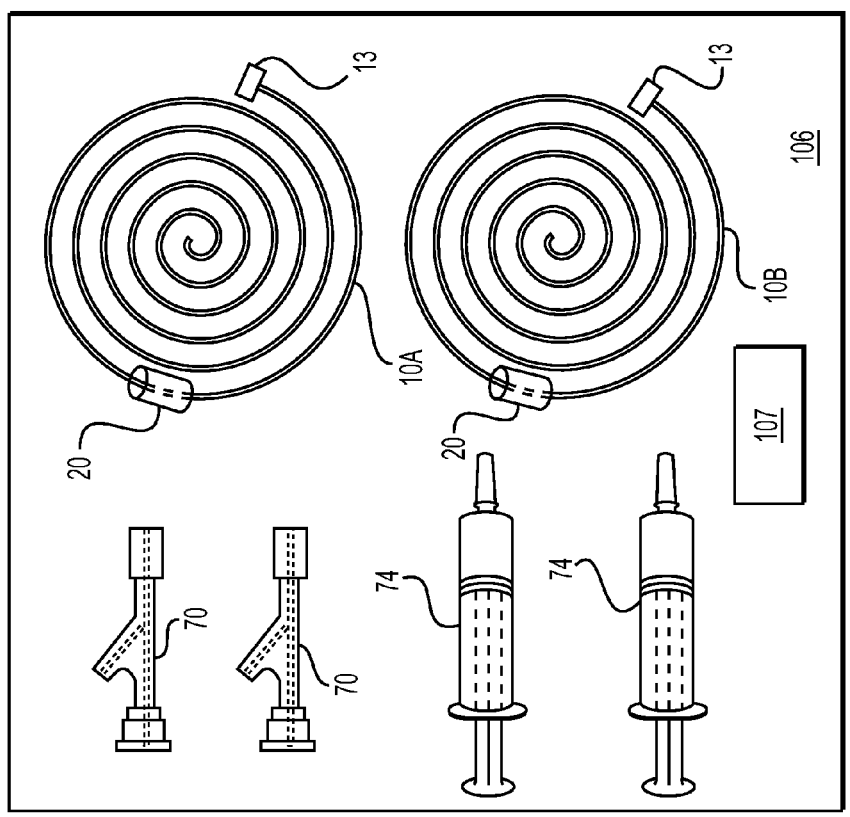
FIG. 19 is an illustration of a sterilization kit, according to at least one aspect of the disclosure.

With reference to FIG. 19, certain components of UV light-based sterilization system 100 may be packaged in a sterilization kit 105 for ease of commercial distribution, storage, and use of system 100. Kit 105 may contain some or all system 100 elements that are considered disposable and not intended to be reused after treatment of a single catheter corresponding to kit 105. For example, a corresponding catheter 1 may be sterilized using light source 60 and the contents of kit 105. FIG. 19 depicts an exemplary sterilization kit for a two-lumen catheter. As depicted, kit 105 can include, within packaging 106, a first fiber optic cable 10A, a second fiber optic cable 20B, two stoppers 20, two catheter connectors 70, two fluid sources 74, and a label 107. Other exemplary sterilization kits 105 can have more or less cables and other components depending on, for example, the number of lumens in a corresponding catheter type.

Label 107 provides information regarding the type of catheter or catheters that the kit 105 corresponds to and is configured to sterilize. This information can include, for example, the catheter brand, catheter version, catheter model, lumen lengths 9A or 9B, and/or various other length characteristics of the catheter relating to lumen length. Label 107 can be affixed to packaging 106 and/or can be including within the packaging 106. Labeling 107 can include additional instructions, warnings, lot numbers, manufacturing dates, expiration dates, and/or information regarding system 100 use or designated catheter types.

As depicted in FIG. 19, stoppers 20 can be attached to cables 10A and 10B at appropriate positions, respectively, such that respective insertable lengths 101 of cables 10A and 10B appropriately correspond to lumen lengths 9A and 9B of the catheter type(s) identified by the information on the label 107. In this manner, a desired threshold distance 102 can be achieved because lengths 103, 9 and 108 are known—in view of the characteristics of catheter type(s) designated in label 107 and the catheter connectors 70 that can be included in kit 105.

Alternatively, stoppers 20 can be unattached to cables 10A and 10B; the stoppers can be either separate from or loosely threaded onto the cables without being secured. In such embodiments, cables 10A and 10B can include one or more stopper markers 21, upon which stopper 20 may be aligned and secured. In some embodiments, a kit 105 can work with various catheters of different types and lumen lengths. Provided cables 10A and 10B can each include multiple stopper markers 21, each marker 21 corresponding with a particular lumen length 9A or 9B.

In alternative embodiments, a kit 105 corresponding to a designated multi-lumen catheter type(s) with different lumen length 9A and 9B can include two cables with identical insertable lengths 101 (or even a single cable), but catheter connectors 70 with different lengths 103. The difference in catheter connector lengths 103 permits desired threshold distances 102 to be achieved for both a longer lumen 4A and a shorter lumen 4B based on a single insertable length 101. Preferably, each catheter connector 70 is colored, contains colored components, or is otherwise marked or flagged to indicate whether is should be used with longer lumen 4A or shorter lumen 4B.

In exemplary embodiments, each fluid source 74 included in kit 105 can be a syringe pre-filled with saline or another fluid suitable for flushing the catheter. With reference to FIG. 19, a kit 105 may include multiple fluid sources 74, for example one fluid source for each lumen of a designated catheter type. However, in other embodiments, a single fluid source 74 can be included in kit 105 and reused for each lumen of a designated catheter type. In yet other embodiments, fluid source 74 can be omitted from kit 105 entirely. And, in some embodiments, sterilization kit 105 can include one or more additional empty syringes or suction devices that can be used to remove fluid from a catheter prior to flushing.

Packaging 106 is preferably sterile packaging that maintains the sterility of its included components. Packaging 106 and its included components can be sterilized by any manner—including sterilization with heat, steam, ethylene oxide, nitrogen dioxide, and/or radiation—so long as the integrity of the packaging and the components are not undermined. Packaging 106 can also provide physical protection for included components, for example, through rigid or semi-rigid inserts, preferably made of plastic. Packaging 106 can further include sub-packaging, for example, inserts to house coiled cable 10; tubing through which a cable 10 can be threaded and stored; sub-packaging that separates components for sterilizing each respective lumen of a multi-lumen catheter; and/or additional protective packaging for a fluid source(s) 74.

Additional Safety Controls

UV light-based sterilization system 100 may provide additional safety measures to prevent the inappropriate re-use of fiber optic cable 10 and/or prevent the use of an expired fiber optic cable 10. In some embodiments, fiber optic cable 10 may include a biocompatible marker 50 affixed to its tip, which may shear off and/or dissolve in the patient's bloodstream and or saline or another fluid. After engaging fiber optic connector 13 with fiber optic port 63, detector 80 may measure backreflectance of, e.g., light at one or more biosafe wavelengths provided by light source 62, such that controller 90 may determine if biocompatible marker 50 is still present. If controller 90 determines that biocompatible marker 50 is not present, it may assume that fiber optic cable 10 has been previously used and either preclude its use and/or warn the operator.

Additionally, in embodiments to prevent inappropriate re-use of fiber optic cable 10, biocompatible marker 50 may be colored such that the operator may directly observe whether or not fiber optic cable 10 had been previously used. For example, biocompatible marker 50 may be a colored or dyed substance, such as a biosafe salt, sugar, wax or fatty acid, that is distributed at the tip of and/or on top of fiber buffer 17 along the length of fiber optic cable 10. By observing the presence or absence of the dye, an operator may determine if fiber optic cable 10 had previously been used. Alternatively or additionally, the packaging of fiber optic cable 10 may be un-resealable as prevent inappropriate re-use fiber optic cable 10.

Additional measures to prevent inappropriate re-use of fiber optic cable 10 or use of an expired fiber optic cable may be incorporated into more complex UV light-based sterilization system 100, such as, for example cartridge-based fiber optic control system 130. As discussed above, cartridge 135 may store data including a unique ID; an expiration date; and information indicating whether it was previously used. Cartridge control system base unit 137 may preclude use of cartridge 135 and/or provide a warning to the operator if, for example, a cartridge 135 with that same unique ID (which would presumably be the same cartridge 135) had previously been used; the manufacturer had issued a recall for cartridge 135 with that same unique ID (or of the same manufacturing batch number); the expiration date had passed; or if the data directly indicates that cartridge 135 had already been used.

Mediport Adapter

Figure 16A:
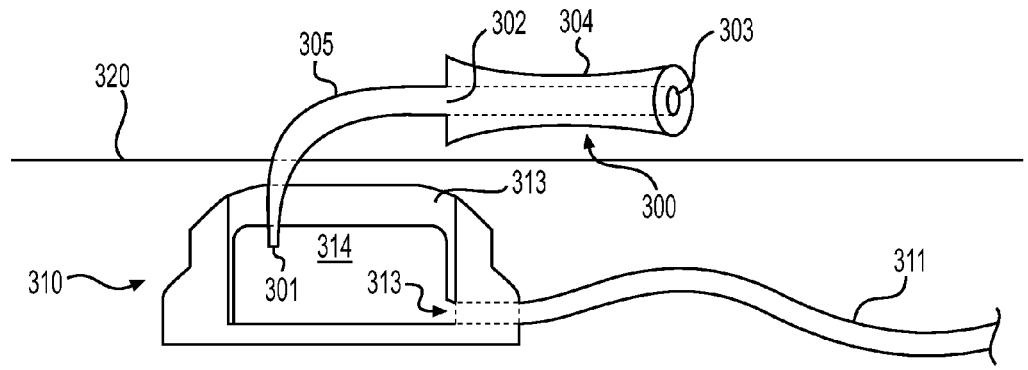
FIGS. 16A-C are illustrations of a technique for adapting UV light-based sterilization techniques to a subcutaneous port, according to at least one aspect of the disclosure.
Figure 16B:
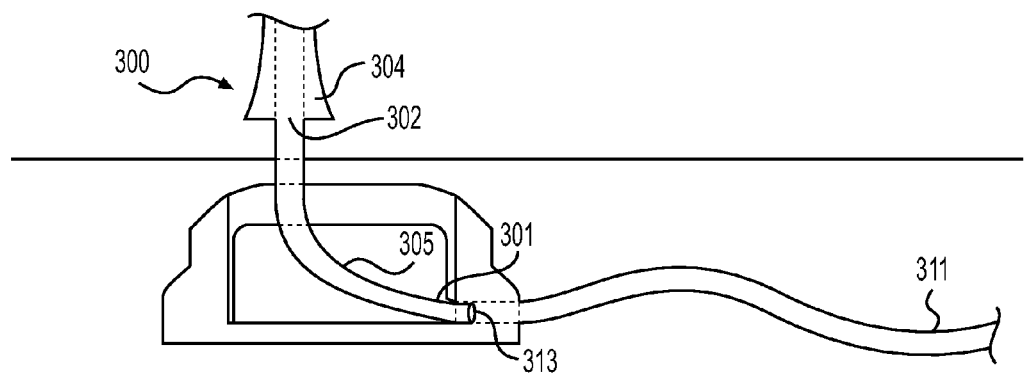
Figure 16C:
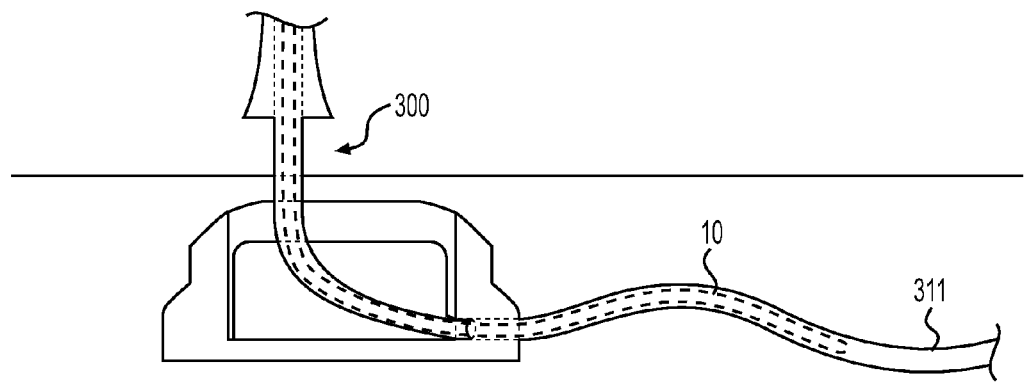

With reference to FIGS. 16A-C, patients who require long term vascular access commonly have subcutaneous ports, such mediports 310, implanted under their skin 320 to permit delivery intravenous medicines and/or other fluids into the bloodstream. Mediport 310 includes re-pierceable septum 313, hollow body 314, and mediport catheter 310 (which typically delivers fluids to a central vein), and mediport catheter lumen opening 312, wherein hollow body 314 is connected to mediport catheter 310. In common practice, an operator may deliver medication through mediport 310 by inserting a needle through septum 313 and into hollow body 314. After delivering the medication and removing the needle, the medical professional may flush the medication through mediport catheter 310 and into the patient's bloodstream by injecting saline or another fluid into mediport hollow body 314. Mediport catheters 310, like other types of catheters, are subject to infection and may be sterilized with UVC light. However, as mediports 310 are in a subcutaneous location, they do not include catheter hubs 5. Thus, additional mechanisms and techniques may be required to place fiber optic cable 10 within lumen 4 of mediport catheter 310 such that UV light-based sterilization may proceed.

As shown in FIGS. 16A-C, mediport insertion adapter 300 may permit the sterilization of mediport catheter 310 using UV light-based sterilization techniques disclosed herein. Further, the teachings disclosed herein regarding mediport insertion adapter 300 may also be applicable to adapters for subcutaneous ports that are not mediports 310. Mediport insertion adapter may include piercing and lodging tip 301, adapter conduit 302, fiber receiving opening 303, adapter handle 304, and curved needle 305. Curved needle 305 may be formed at such a curvature as to ensure that an inserted fiber optic cable 10 will maintain its minimum momentary bending radius and that the propagation of UV light through it would not be hindered. And in preferred embodiments, fiber receiving opening 303 may include a one-way valve, similar to fiber insertion port 71. Additionally, mediport insertion adapter 310 may be disposable for safety reasons and/or may be radiopaque or contain radiopaque elements, such that the operator may be guided by fluoroscopy or the like during adapter insertion and use.

Embodiments consistent with the following disclosure may be used to install mediport insertion adapter 300 in mediport 310 and position fiber optic cable 10 in mediport catheter 311 for sterilization. With reference to FIG. 16A, the operator may pierce the patient's skin 320 and septum 313 with piercing and lodging tip 301. The operator may manipulate mediport insertion adapter 300 by holding adapter handle 304, which, may be thicker than curved needle 305. In some embodiments, adapter handle 304 may include additional components that may, for example, be plate-shaped, bar-shaped, or cross-shaped, as to improve operator's ability to accurately manipulate of adapter 300. Preferably, septum 313 should be pierced in a location opposite from mediport catheter lumen opening 312, such that piercing and lodging tip 301 may later engage with mediport catheter lumen opening 312 in a relatively smooth and non-angular fashion.

With reference to FIG. 16B, the operator may push adapter 300 into mediport 310 such that piercing and lodging tip 301 engages with mediport catheter lumen opening 312. The operator may have to rely on tactile feedback to determine when this engagement occurs, and the process of properly installing adapter 300 may require both skill and dexterity. In some embodiments, the operator may then secure a properly installed adapter 300 in place, for example, by wrapping medical tape around adapter handle 304 and affixing it to skin 320.

With reference to FIG. 16C, the operator may then thread fiber optic cable 10 into fiber receiving opening 303 (not shown), through handle 304 and curved needle 305 via adapter conduit 302, and into mediport catheter 311 via the engagement between piercing and lodging tip 301 and mediport catheter lumen opening 312. Once fiber optic cable 10 is positioned within mediport catheter 311, UV light-based sterilization techniques consistent with embodiments disclosed herein may be performed. The techniques, however, may be modified to accommodate mediport 310 and mediport insertion adapter 300: For example, stopper 20 may be positioned such that when stopper 20 is adjacent to adapter handle 304, the distal end of fiber optic cable 10 may be located at the distal end of mediport catheter 311. Additionally, mediport catheter 311 may be flushed by inserting first inserting the needle of a syringe containing flushing fluid into mediport hollow body 314 rather than by using fluid port 73.

It may also be noted that if the angle between adapter 300 and mediport catheter 311 is too steep, or if piercing and lodging tip 301 and mediport catheter lumen opening 312 are otherwise not appropriately engaged 311, it may be difficult to smoothly position and move fiber optic cable 10 within mediport catheter 311. In turn, this may preclude or hinder UV-light based sterilization.

Biogel-Based Catheter Sterilization

In certain embodiments, catheter lumen 4 walls may be sterilized by UVC light propagated and scattered by a biogel that may be pushed into, and then removed from, catheter 1. The biogel may be a viscous, biocompatible gel that has a greater propensity to stick to itself than the intraluminal walls of catheter 1. For example, the biogel may comprise alginate polysaccharide, agarose, or the like. In some embodiments, the biogel may also have antimicrobial properties; it may be impregnated with antibiotics, biofilm reducing substances (such as those discussed above with respect to biofilm cleaning solutions), antiseptics, and/or other substance that may enhance sterilization effectiveness.

Figure 17:
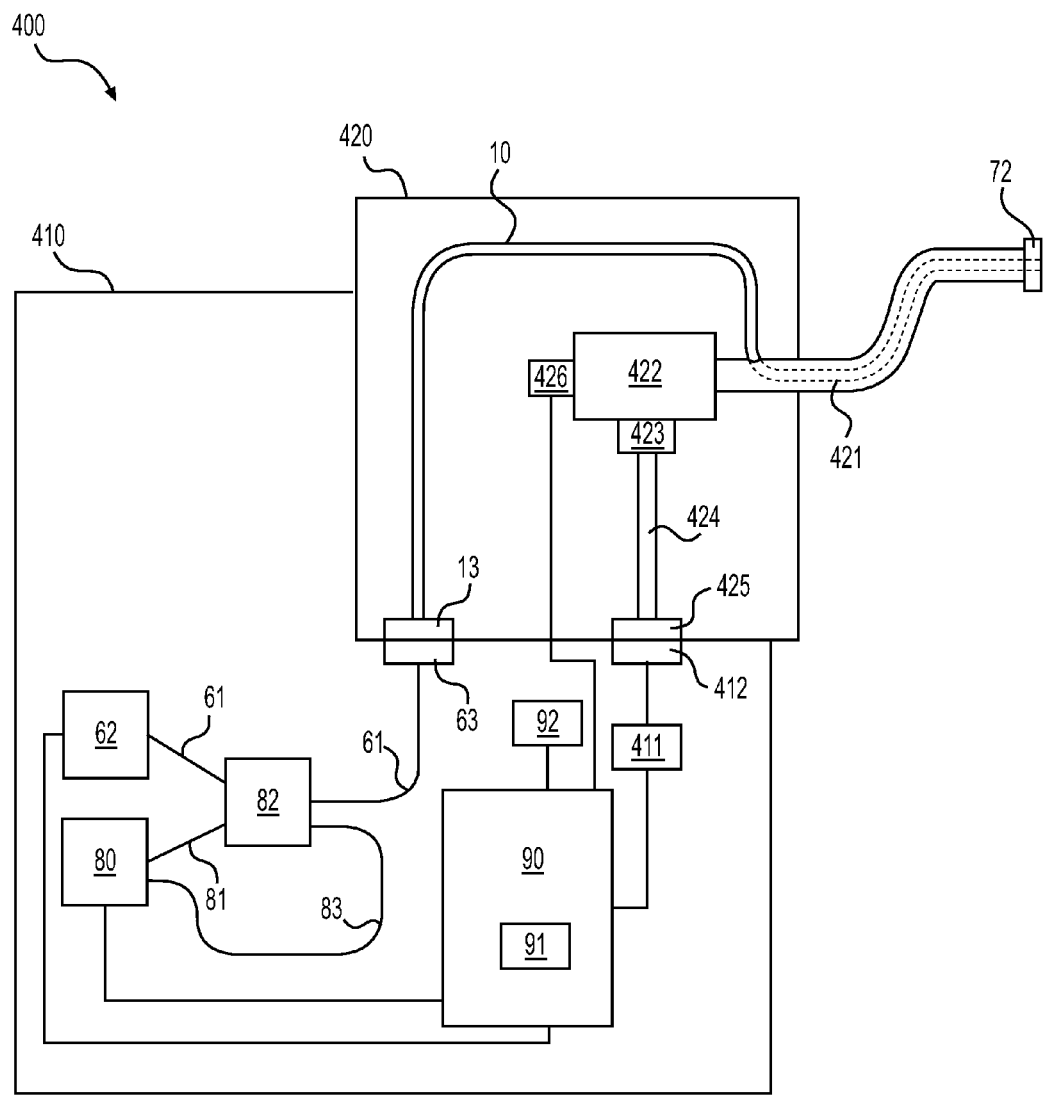
FIG. 17 is an illustration of a UV light-based sterilization system incorporating biogel-based UV light sterilization techniques, according to at least one aspect of the disclosure.

With reference to FIG. 17, embodiments of biogel-based UV light sterilization system 400 may be used to sterilize catheter 1. System 400 may comprise biogel system base 410 and a disposable biogel cartridge 420, which may maintain a sterile separation from base 410. Biogel system base 410 may include many of the same components of cartridge control base unit 137 and may perform much of the same functionality, as discussed in this disclosure. However, in lieu of motor 131, biogel system base 410 may include pressure source 411, which may be coupled to biogel cartridge 420 at base pressure couple 412. Pressure source 411 may provide forward pressure or reverse pressure (i.e., suction), to drive the movement of the biogel. Such pressure may be generated by conventional means, such as a motor.

Biogel cartridge 420 may contain biogel storage 422, which may receive pressure via pressurizing line 424, connected to cartridge pressure couple 425, which, in turn, engages with base pressure couple 412. Preferably, a valve or diaphragm 423 may maintain a sterile separation between the biogel storage 422 and pressure line 424, which flows into biogel system base 410. When sufficient pressure is administered to biogel storage 422, biogel may flow through IV tubing 421 and into catheter 1 (not shown), which may be coupled to the biogel cartridge at hub adapter 72. Biogel sensor 426 may monitor the state of biogel storage 422 such that controller 90 (coupled to sensor 426 during cartridge engagement) may determine, for example, how much biogel has moved outside of biogel cartridge 420 (and presumably into catheter 1), the pressure of biogel storage 422, and/or monitor for various operational errors or defects in system performance, such as a clog in the system.

During operation of biogel-based UV light sterilization system 400, the biogel may first be pushed through IV tubing 421 and fill catheter 1. Then, UV light may be propagated to the biogel in catheter 1 via fiber optic cable 10, which may be permanently inserted into IV tubing 421 within biogel cartridge 420, and which may have a light-emitting distal end 12 positioned near hub adapter 72 and directed into catheter 1. In some embodiments, where the biogel remains in place throughout the application of UV radiation (for an appropriate amount of time), sterilization may be considered to be static. In such embodiments, biofilm may optionally contain scattering centers 141. In other embodiments, where the biofilm is slowly withdrawn (at an appropriate steady rate) during the application of UV radiation, sterilization may be considered to be dynamic. Biogel may be withdrawn from catheter 1 and back into biogel storage via reverse pressurization of biogel storage 422 by pressure source 411. Further, biogel may advantageously remove some or all biofilm from catheter 1 as it is withdrawn. After the sterilization process has been completed, cartridge 420 should be disposed of.

In certain embodiments (not shown), catheter 1 may also be flushed with a fluid or treated with various biofilm removal techniques after biogel has been withdrawn, in order to clear any remaining biogel or biofilm debris. The flushing may be done automatically using a fluid source (not shown) within or attached to biogel cartridge 420. Alternatively, a manual flushing process may be used.

In yet other embodiments, the gel can have the property of an refractive index that is higher than the refractive index of the surrounding catheter material. This, in effect, will cause catheter 1 to behave like a fiber optic. In such embodiments, scattering centers 141 may optionally be used to scatter UV light along the walls of lumen 4.

While the foregoing written description enables one of ordinary skill to make and use what is considered presently to be the best mode thereof, those of ordinary skill will understand and appreciate the existence of variations, combinations, and equivalents of the specific embodiments disclosed herein. Other embodiments of the disclosure will be apparent to those skilled in the art from consideration of the specification and practice of the aspects disclosed herein. The invention should therefore not be limited by the above described embodiments and examples, but by all embodiments and methods within the scope and spirit of the invention.

The invention claimed is:

1. A method for sterilizing a catheter with at least a first lumen, comprising:
    attaching a hub of the first lumen to a hub adapter of a catheter connector and attaching a fluid source to a fluid port of the catheter connector, prior to flushing the first lumen;
    unlocking the first lumen by disengaging a tubing clamp configured to block fluid flow through the first lumen, prior to flushing the first lumen;
    inserting a distal end of a fiber optic cable into a fiber insertion port of the catheter connector attached to the hub of the first lumen;
    flushing the first lumen with fluid from the fluid source;
    inserting the fiber optic cable into the first lumen until a stopper of the fiber optic cable is adjacent to the fiber insertion port after flushing the first lumen;
    providing light to the fiber optic cable from a light source after the fiber optic cable is inserted into the first lumen;
    withdrawing the fiber optic cable from the first lumen while the light is provided;
    ceasing to provide light to the fiber optic cable after the fiber optic cable is withdrawn from the first lumen;
    locking the first lumen by engaging the tubing clamp, after withdrawing the fiber optic cable from the catheter; and
    disengaging the hub from the hub adapter, after locking the first lumen.

2. The method of claim 1, wherein the step of inserting the fiber optic cable into a fiber insertion port occurs prior to the step of flushing the first lumen.

3. The method of claim 1, wherein, when the stopper is adjacent to the fiber insertion port, the distal end of the fiber optic cable is within 6 cm from a distal end of the first lumen and does not extend beyond a distal end of the first lumen.

4. The method of claim 3, wherein, during the step of inserting the fiber optic cable into the first lumen, when the stopper is adjacent to fiber insertion port, the distal end of the fiber optic cable is within 3 cm from the distal end of the first lumen.

5. The method of claim 1, wherein:
    the step of withdrawing the fiber optic cable from the catheter ends when the distal end of a fiber optic cable is positioned within the catheter connector, and
    the step of ceasing to provide light to the fiber optic cable occurs while the distal end of a fiber optic cable is positioned within the catheter connector.

6. The method of claim 1, wherein the stopper is at least one of at torque device, a hinged device, a clamping apparatus, and a bead comprising at least one of silica, plastic, resin, or epoxy.

7. The method of claim 1, further comprising:
    providing, as the catheter connector and fiber insertion port, respectively, a hemostasis valve with a one-way valve.

8. The method of claim 1, further comprising:
    aligning the stopper on a first stopper marker of the fiber optic cable; and
    securing the stopper to the fiber optic cable.

9. The method of claim 8, further comprising:
    selecting the first stopper marker from a plurality of stopper markings, such that first stopper marker corresponds to a combined length of the first lumen and the catheter connector.

10. The method of claim 1, further comprising:
    treating a second lumen of the catheter with light from the light source.

11. The method of claim 1, further comprising:
    confirming a match in color between at least one of the hub and at least a portion of the catheter connector, and at least one of a fiber optic connector, the stopper, and a marking on the fiber optic cable.

12. The method of claim 1, further comprising:
    providing, as the light source, a laser that provides light in the UVC band.

13. The method of claim 1, wherein the step of withdrawing the fiber optic cable is performed by hand using a time-keeping device to maintain a steady withdrawal rate.

14. The method of claim 1, further comprising:
    withdrawing fluid from the first lumen through the catheter connector using suction,
    wherein the step of withdrawing fluid from the first lumen occurs prior to the step of flushing the first lumen.

15. The method of claim 1, further comprising:
    providing, as the fluid source, a syringe containing a saline solution.

16. The method of claim 1, further comprising:
    providing, as the light source, a laser that provides light at a power of between 1 mW and 50 mW.

17. The method of claim 1, further comprising:
    providing, as the light source, a laser that provides light with a peak wavelength of approximately 266 nm.

18. The method of claim 1, further comprising:
    providing, as the light source, a laser that provides pulsed light.

19. The method of claim 1, further comprising:
    providing, as the fiber optic cable, a sheathed fiber comprising a cable sheath; and
    at least partially withdrawing the cable sheath from the first lumen to expose a tip of the sheathed fiber, prior to providing light to the fiber optic.

20. The method of claim 1, wherein:
    the step of withdrawing the fiber optic cable from the first lumen occurs at a rate approximately equal to the light source power divided by the product of a desired light dose times the diameter of the first lumen times $\pi$.

21. A method for sterilizing a catheter with at least a first lumen, comprising:
    inserting a distal end of a fiber optic cable into a fiber insertion port of a catheter connector attached to a hub of the first lumen;
    flushing the first lumen with fluid from a fluid source;
    inserting the fiber optic cable into the first lumen until a stopper of the fiber optic cable is adjacent to the fiber insertion port;
    providing light to the fiber optic cable from a light source after the fiber optic cable is inserted into the first lumen;
    ceasing to provide light to the fiber optic cable;
    withdrawing the fiber optic cable from the first lumen; and
    locking the first lumen by engaging the tubing clamp, after withdrawing the fiber optic cable from the catheter.

22. The method of claim 21, wherein:
    the step of proceeds for a predetermined duration of time approximately equal to a desired light dose times the length of the first lumen the diameter of the first lumen times $\pi$ divided by the light source power.

23. The method of claim 21, further comprising:
    withdrawing fluid from the first lumen through the catheter connector using suction,
    wherein the step of withdrawing fluid from the first lumen occurs prior to the step of flushing the first lumen.

24. The method of claim 21, further comprising:
providing, as the fluid source, a syringe containing a saline solution.

25. The method of claim 21, further comprising:
providing, as the light source, a laser that provides light at a power of between 1 mW and 50 mW and a peak wavelength of approximately 266 nm.

26. The method of claim 21, further comprising:
providing, as the light source, a laser that provides pulsed light.

27. A method for sterilizing a catheter with at least a first lumen, comprising:
confirming a match in color between at least one of a hub of the first lumen and at least a portion of a catheter connector, and at least one of a fiber optic connector, the stopper, and a marking on the fiber optic cable;
inserting a distal end of a fiber optic cable into a fiber insertion port of the catheter connector attached to the hub of the first lumen;
flushing the first lumen with fluid from a fluid source;
inserting the fiber optic cable into the first lumen until a stopper of the fiber optic cable is adjacent to the fiber insertion port;
providing light to the fiber optic cable from a light source after the fiber optic cable is inserted into the first lumen;
ceasing to provide light to the fiber optic cable;
withdrawing the fiber optic cable from the first lumen.

28. The method of claim 27, wherein:
the step of proceeds for a predetermined duration of time approximately equal to a desired light dose times the length of the first lumen the diameter of the first lumen times $\pi$ divided by the light source power.

29. The method of claim 27, further comprising:
withdrawing fluid from the first lumen through the catheter connector using suction,
wherein the step of withdrawing fluid from the first lumen occurs prior to the step of flushing the first lumen.

30. The method of claim 27, further comprising:
providing, as the light source, a laser that provides light at a power of between 1 mW and 50 mW and a peak wavelength of approximately 266 nm.

* * * * *